US011433177B2

(12) United States Patent
Oruklu et al.

(10) Patent No.: US 11,433,177 B2
(45) Date of Patent: *Sep. 6, 2022

(54) INFUSION SYSTEM WHICH UTILIZES ONE OR MORE SENSORS AND ADDITIONAL INFORMATION TO MAKE AN AIR DETERMINATION REGARDING THE INFUSION SYSTEM

(71) Applicant: ICU Medical, Inc., San Clemente, CA (US)

(72) Inventors: Meriyan Oruklu, Chicago, IL (US); Timothy L. Ruchti, Gurnee, IL (US); Paul T. Kotnik, Commerce Township, MI (US); Anatoly S. Belkin, Glenview, IL (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/233,740

(22) Filed: Dec. 27, 2018

(65) Prior Publication Data
US 2019/0269846 A1 Sep. 5, 2019

Related U.S. Application Data

(63) Continuation of application No. 14/289,848, filed on May 29, 2014, now Pat. No. 10,166,328.
(Continued)

(51) Int. Cl.
*A61M 5/168* (2006.01)
*A61M 5/142* (2006.01)
*A61M 5/36* (2006.01)

(52) U.S. Cl.
CPC .......... *A61M 5/142* (2013.01); *A61M 5/1684* (2013.01); *A61M 5/365* (2013.01);
(Continued)

(58) Field of Classification Search
None
See application file for complete search history.

(56) References Cited

U.S. PATENT DOCUMENTS 3,401,337 A 9/1968 Beusman et al.
3,484,681 A 12/1969 Grady, Jr. et al.
(Continued)

FOREIGN PATENT DOCUMENTS

AU 2013216679 9/2013
BR PI0704229-9 11/2009
(Continued)

OTHER PUBLICATIONS

Alaedeen et al., "Total Parenteral Nutrition-Associated Hyperglycemia Correlates with Prolonged Mechanical Ventilation and Hospital Stay in Septic Infants", Journal of Pediatric Surgery, Jan. 2006, vol. 41, No. 1, pp. 239-244.
(Continued)

*Primary Examiner* — Jenna Zhang
(74) *Attorney, Agent, or Firm* — Knobbe Martens Olson & Bear, LLP

(57) ABSTRACT

In one step of a method for infusing an infusion fluid, the infusion fluid is pumped through a fluid delivery line of an infusion system. In another step, measurements are taken with at least one sensor connected to the infusion system. In an additional step, an air determination is determined with at least one processor. The air determination is related to air in the fluid delivery line. The air determination is based on the measurements taken by the at least one sensor. The air determination is further based on: (1) medication information regarding the infusion fluid or infusion information regarding the infusion of the infusion fluid; or (2) multichannel filtering of the measurements from the at least one sensor or non-linear mapping of the measurements from the at least one sensor; and statistical process control charts
(Continued)

applied to the multi-channel filtered measurements or applied to the non-linear mapped measurements.

13 Claims, 12 Drawing Sheets

Related U.S. Application Data

(60) Provisional application No. 61/828,522, filed on May 29, 2013.

(52) U.S. Cl.
CPC ... *A61M 2205/18* (2013.01); *A61M 2205/332* (2013.01); *A61M 2205/3331* (2013.01); *A61M 2205/3334* (2013.01); *A61M 2205/3368* (2013.01)

(56) References Cited

U.S. PATENT DOCUMENTS

| | | |
|---|---|---|
| 3,699,320 A | 10/1972 | Zimmerman et al. |
| 3,727,074 A | 4/1973 | Keller et al. |
| 3,731,679 A | 5/1973 | Wilhelmson et al. |
| 3,768,084 A | 10/1973 | Haynes |
| 3,770,354 A | 11/1973 | Tsuruta et al. |
| 3,778,702 A | 12/1973 | Finger |
| 3,806,821 A | 4/1974 | Niemeyer et al. |
| 3,838,565 A | 10/1974 | Carlyle |
| 3,854,038 A | 12/1974 | McKinley |
| 3,886,459 A | 5/1975 | Hufford et al. |
| 3,890,554 A | 6/1975 | Yoshitake et al. |
| 3,898,637 A | 8/1975 | Wolstenholme |
| 3,901,231 A | 8/1975 | Olson |
| 3,909,693 A | 9/1975 | Yoshitake et al. |
| 3,910,701 A | 10/1975 | Henderson |
| 3,911,343 A | 10/1975 | Oster |
| 3,919,608 A | 11/1975 | Usami et al. |
| 3,921,622 A | 11/1975 | Cole |
| 3,930,404 A | 1/1976 | Ryden, Jr. |
| 3,933,431 A | 1/1976 | Trujillo et al. |
| 3,935,876 A | 2/1976 | Massie et al. |
| 3,944,963 A | 3/1976 | Hively |
| 3,966,358 A | 6/1976 | Heimes et al. |
| 3,971,980 A | 7/1976 | Jungfer et al. |
| 3,974,681 A | 8/1976 | Namery |
| 3,974,683 A | 8/1976 | Martin |
| 3,985,467 A | 10/1976 | Lefferson |
| 3,990,444 A | 11/1976 | Vial |
| 3,997,888 A | 12/1976 | Kremer |
| 4,005,724 A | 2/1977 | Courtot |
| 4,014,206 A | 3/1977 | Taylor |
| 4,038,982 A | 8/1977 | Burke |
| 4,039,269 A | 8/1977 | Pickering |
| 4,048,474 A | 9/1977 | Olesen |
| 4,049,954 A | 9/1977 | Da Costa Vieira et al. |
| 4,055,175 A | 10/1977 | Clemens et al. |
| 4,068,521 A | 1/1978 | Cosentino et al. |
| 4,078,562 A | 3/1978 | Friedman |
| 4,089,227 A | 5/1978 | Falgari et al. |
| 4,094,318 A | 6/1978 | Burke |
| 4,105,028 A | 8/1978 | Sadlier et al. |
| 4,114,144 A | 9/1978 | Hyman |
| 4,151,845 A | 5/1979 | Clemens |
| 4,155,362 A | 5/1979 | Jess |
| 4,173,224 A | 11/1979 | Marx |
| 4,181,610 A | 1/1980 | Shintani et al. |
| 4,183,244 A | 1/1980 | Kohno et al. |
| 4,195,515 A | 4/1980 | Smoll |
| 4,210,138 A | 7/1980 | Jess et al. |
| 4,213,454 A | 7/1980 | Shim |
| 4,217,993 A | 8/1980 | Jess et al. |
| 4,240,294 A | 12/1980 | Grande |
| 4,240,438 A | 12/1980 | Updike et al. |
| 4,244,365 A | 1/1981 | McGill |
| 4,256,437 A | 3/1981 | Brown |
| 4,261,356 A | 4/1981 | Turner et al. |
| 4,264,861 A | 4/1981 | Radu et al. |
| 4,265,240 A | 5/1981 | Jenkins |
| 4,270,532 A | 6/1981 | Franetzki et al. |
| 4,277,226 A | 7/1981 | Archibald et al. |
| 4,278,085 A | 7/1981 | Shim |
| 4,280,495 A | 7/1981 | Lampert |
| 4,282,872 A | 8/1981 | Franetzki et al. |
| 4,286,202 A | 8/1981 | Clancy et al. |
| 4,290,346 A | 9/1981 | Bujan |
| 4,291,692 A | 9/1981 | Bowman et al. |
| 4,292,405 A | 9/1981 | Mascoli |
| 4,298,357 A | 11/1981 | Permic |
| 4,308,866 A | 1/1982 | Jeliffe |
| 4,312,341 A | 1/1982 | Zissimopoulos |
| 4,319,568 A | 3/1982 | Tregoning |
| 4,322,201 A | 3/1982 | Archibald |
| 4,323,849 A | 4/1982 | Smith |
| 4,324,662 A | 4/1982 | Schnell |
| 4,328,800 A | 5/1982 | Marx |
| 4,328,801 A | 5/1982 | Marx |
| 4,333,045 A | 6/1982 | Oltendorf |
| 4,343,316 A | 8/1982 | Jespersen |
| 4,344,429 A | 8/1982 | Gupton et al. |
| 4,346,707 A | 8/1982 | Whitney et al. |
| 4,360,019 A | 11/1982 | Portner et al. |
| 4,366,384 A | 12/1982 | Jensen |
| 4,367,736 A | 1/1983 | Gupton |
| 4,370,983 A | 2/1983 | Lichtenstein et al. |
| 4,373,527 A | 2/1983 | Fischell |
| 4,379,452 A | 4/1983 | DeVries |
| 4,381,005 A | 4/1983 | Bujan |
| 4,384,578 A | 5/1983 | Winkler |
| 4,385,247 A | 5/1983 | Satomi |
| 4,391,598 A | 7/1983 | Thompson |
| 4,392,849 A | 7/1983 | Petre et al. |
| 4,394,862 A | 7/1983 | Shim |
| 4,395,259 A | 7/1983 | Prestele et al. |
| 4,397,194 A | 8/1983 | Soltz |
| 4,399,362 A | 8/1983 | Cormier et al. |
| 4,407,659 A | 10/1983 | Adam |
| 4,411,651 A | 10/1983 | Schulman |
| 4,418,565 A | 12/1983 | St. John |
| 4,432,699 A | 2/1984 | Beckman et al. |
| 4,432,761 A | 2/1984 | Dawe |
| 4,432,762 A | 2/1984 | Dawe |
| 4,443,218 A | 4/1984 | Decant, Jr. et al. |
| 4,444,546 A | 4/1984 | Pazemenas |
| 4,447,191 A | 5/1984 | Bilstad et al. |
| 4,447,224 A | 5/1984 | Decant, Jr. et al. |
| 4,453,931 A | 6/1984 | Pastrone |
| 4,457,751 A | 7/1984 | Rodler |
| 4,463,301 A | 7/1984 | Moriguchi et al. |
| 4,464,170 A | 8/1984 | Clemens |
| 4,467,654 A | 8/1984 | Murakami et al. |
| 4,468,222 A | 8/1984 | Lundquist |
| 4,468,601 A | 8/1984 | Chamran et al. |
| 4,469,481 A | 9/1984 | Kobayashi |
| 4,475,666 A | 10/1984 | Bilbrey et al. |
| 4,475,901 A | 10/1984 | Kraegen et al. |
| 4,477,756 A | 10/1984 | Moriguchi |
| 4,479,760 A | 10/1984 | Bilstad et al. |
| 4,480,218 A | 10/1984 | Hair |
| 4,480,483 A | 11/1984 | McShane |
| 4,483,202 A | 11/1984 | Ogua et al. |
| 4,487,601 A | 12/1984 | Lindemann |
| 4,492,909 A | 1/1985 | Hartwig |
| 4,496,346 A | 1/1985 | Mosteller |
| 4,498,843 A | 2/1985 | Schneider et al. |
| 4,501,531 A | 2/1985 | Bilstad et al. |
| 4,504,263 A | 3/1985 | Steuer |
| 4,507,112 A | 3/1985 | Hillel |
| 4,510,266 A | 4/1985 | Eertink |
| 4,515,584 A | 5/1985 | Abe et al. |
| 4,519,792 A | 5/1985 | Dawe |
| 4,521,212 A | 6/1985 | Ruschke |
| 4,525,163 A | 6/1985 | Slavik et al. |
| 4,526,568 A | 7/1985 | Clemens et al. |

(56) References Cited

U.S. PATENT DOCUMENTS

| | | |
|---|---|---|
| 4,526,574 A | 7/1985 | Pekkarinen |
| 4,529,401 A | 7/1985 | Leslie et al. |
| 4,533,350 A | 8/1985 | Danby et al. |
| 4,543,955 A | 10/1985 | Schroeppel |
| 4,551,134 A | 11/1985 | Slavik et al. |
| 4,553,958 A | 11/1985 | LeCocq |
| 4,559,036 A | 12/1985 | Wunsch |
| 4,559,037 A | 12/1985 | Franetzki et al. |
| 4,559,044 A | 12/1985 | Robinson |
| 4,559,454 A | 12/1985 | Kramer |
| 4,565,500 A | 1/1986 | Jeensalaute et al. |
| 4,583,981 A | 4/1986 | Urquhart et al. |
| 4,587,473 A | 5/1986 | Turvey |
| 4,607,520 A | 8/1986 | Dam |
| 4,617,014 A | 10/1986 | Cannon et al. |
| 4,624,661 A | 11/1986 | Arimond |
| 4,627,835 A | 12/1986 | Fenton, Jr. |
| 4,633,878 A | 1/1987 | Bombardieri |
| 4,634,426 A | 1/1987 | Kamen |
| 4,634,427 A | 1/1987 | Hannula et al. |
| 4,636,144 A | 1/1987 | Abe et al. |
| 4,637,813 A | 1/1987 | DeVries |
| 4,645,489 A | 2/1987 | Krumme |
| 4,648,869 A | 3/1987 | Bobo, Jr. |
| 4,652,260 A | 3/1987 | Fenton, Jr. et al. |
| 4,658,244 A | 4/1987 | Meijer |
| 4,668,216 A | 5/1987 | Martin |
| 4,668,945 A | 5/1987 | Aldrovandi et al. |
| 4,673,334 A | 6/1987 | Allington et al. |
| 4,673,389 A | 6/1987 | Archibald et al. |
| 4,676,776 A | 6/1987 | Howson et al. |
| 4,677,359 A | 6/1987 | Enami et al. |
| 4,678,979 A | 7/1987 | Hori |
| 4,678,998 A | 7/1987 | Muramatsu |
| 4,679,562 A | 7/1987 | Luksha |
| 4,683,428 A | 7/1987 | Gete |
| 4,685,903 A | 8/1987 | Cable et al. |
| 4,690,673 A | 9/1987 | Bloomquist |
| 4,691,153 A | 9/1987 | Nishimura |
| 4,692,145 A | 9/1987 | Weyant |
| 4,696,671 A | 9/1987 | Epstein et al. |
| 4,697,129 A | 9/1987 | Enami et al. |
| 4,702,675 A | 10/1987 | Aldrovandi et al. |
| 4,705,506 A | 11/1987 | Archibald et al. |
| 4,710,106 A | 12/1987 | Iwata et al. |
| 4,714,462 A | 12/1987 | DiDomenico |
| 4,714,463 A | 12/1987 | Archibald et al. |
| 4,718,576 A | 1/1988 | Tamura et al. |
| 4,720,636 A | 1/1988 | Benner |
| 4,722,224 A | 2/1988 | Scheller et al. |
| 4,722,734 A | 2/1988 | Kolin |
| 4,731,051 A | 3/1988 | Fischell |
| 4,731,057 A | 3/1988 | Tanaka et al. |
| 4,737,711 A | 4/1988 | O'Hare |
| 4,739,346 A | 4/1988 | Buckley |
| 4,741,732 A | 5/1988 | Crankshaw et al. |
| 4,741,736 A | 5/1988 | Brown |
| 4,748,857 A | 6/1988 | Nakagawa |
| 4,751,445 A | 6/1988 | Sakai |
| 4,756,706 A | 7/1988 | Kerns et al. |
| 4,758,228 A | 7/1988 | Williams |
| 4,763,525 A | 8/1988 | Cobb |
| 4,764,166 A | 8/1988 | Spani et al. |
| 4,764,697 A | 8/1988 | Christiaens |
| 4,776,842 A | 10/1988 | Franetzki et al. |
| 4,781,687 A | 11/1988 | Wall |
| 4,784,576 A | 11/1988 | Bloom et al. |
| 4,785,184 A | 11/1988 | Bien et al. |
| 4,785,799 A | 11/1988 | Schoon et al. |
| 4,785,969 A | 11/1988 | McLaughlin |
| 4,786,800 A | 11/1988 | Kamen |
| 4,789,014 A | 12/1988 | DiGianfilippo |
| 4,797,655 A | 1/1989 | Orndal et al. |
| 4,803,389 A | 2/1989 | Ogawa et al. |
| 4,803,625 A | 2/1989 | Fu et al. |
| 4,818,186 A | 4/1989 | Pastrone et al. |
| 4,820,281 A | 4/1989 | Lawler |
| 4,821,558 A | 4/1989 | Pastrone et al. |
| 4,828,545 A | 5/1989 | Epstein et al. |
| 4,828,693 A | 5/1989 | Lindsay |
| 4,829,448 A | 5/1989 | Balding et al. |
| 4,838,856 A | 6/1989 | Mulreany et al. |
| 4,838,857 A | 6/1989 | Strowe et al. |
| 4,840,542 A | 6/1989 | Abbott |
| 4,842,584 A | 6/1989 | Pastrone et al. |
| 4,845,487 A | 7/1989 | Frantz et al. |
| 4,846,792 A | 7/1989 | Bobo et al. |
| 4,850,805 A | 7/1989 | Madsen et al. |
| 4,851,755 A | 7/1989 | Fincher |
| 4,854,324 A | 8/1989 | Hirschman et al. |
| 4,856,339 A | 8/1989 | Williams |
| 4,857,048 A | 8/1989 | Simons et al. |
| 4,857,050 A | 8/1989 | Lentz et al. |
| 4,858,154 A | 8/1989 | Anderson et al. |
| 4,863,425 A | 9/1989 | Slate et al. |
| 4,865,584 A | 9/1989 | Epstein et al. |
| 4,869,722 A | 9/1989 | Heyman |
| 4,874,359 A | 10/1989 | White et al. |
| 4,881,413 A | 11/1989 | Georgi et al. |
| 4,882,575 A | 11/1989 | Kawahara |
| 4,884,013 A | 11/1989 | Jackson et al. |
| 4,884,065 A | 11/1989 | Crouse et al. |
| 4,886,422 A | 12/1989 | Takeuchi et al. |
| 4,898,576 A | 2/1990 | Philip |
| 4,898,578 A | 2/1990 | Rubalcaba, Jr. |
| 4,906,103 A | 3/1990 | Kao |
| 4,908,017 A | 3/1990 | Howson et al. |
| 4,910,475 A | 3/1990 | Lin |
| 4,919,595 A | 4/1990 | Likuski et al. |
| 4,919,596 A | 4/1990 | Slate et al. |
| 4,925,444 A | 5/1990 | Orkin et al. |
| 4,927,411 A | 5/1990 | Pastrone et al. |
| 4,930,358 A | 6/1990 | Motegi et al. |
| 4,936,820 A | 6/1990 | Dennehey |
| 4,936,828 A | 6/1990 | Chiang |
| 4,938,079 A | 7/1990 | Goldberg |
| 4,943,279 A | 7/1990 | Samiotes et al. |
| 4,946,439 A | 8/1990 | Eggers |
| 4,947,856 A | 8/1990 | Beard |
| 4,950,235 A | 8/1990 | Slate et al. |
| 4,950,244 A | 8/1990 | Fellingham |
| 4,959,050 A | 9/1990 | Bobo, Jr. |
| 4,966,579 A | 10/1990 | Polaschegg |
| 4,968,941 A | 11/1990 | Rogers |
| 4,972,842 A | 11/1990 | Korten et al. |
| 4,976,687 A | 12/1990 | Martin |
| 4,978,335 A | 12/1990 | Arthur, III |
| 4,979,940 A | 12/1990 | Lapp et al. |
| 4,981,467 A | 1/1991 | Bobo et al. |
| 5,000,663 A | 3/1991 | Gorton |
| 5,000,739 A | 3/1991 | Kulisz et al. |
| 5,006,050 A | 4/1991 | Cooke et al. |
| 5,010,473 A | 4/1991 | Jacobs |
| 5,014,714 A | 5/1991 | Millay et al. |
| 5,018,945 A | 5/1991 | D'Silva |
| 5,026,348 A | 6/1991 | Venegas |
| 5,028,857 A | 7/1991 | Taghezout |
| 5,032,112 A | 7/1991 | Fairchild et al. |
| 5,034,004 A | 7/1991 | Crankshaw |
| 5,035,143 A | 7/1991 | Latimer et al. |
| 5,041,086 A | 8/1991 | Koenig et al. |
| 5,043,706 A | 8/1991 | Oliver |
| 5,045,069 A | 9/1991 | Imparato |
| 5,049,047 A | 9/1991 | Polaschegg et al. |
| 5,052,230 A | 10/1991 | Lang |
| 5,053,747 A | 10/1991 | Slate et al. |
| 5,055,761 A | 10/1991 | Mills |
| 5,056,992 A | 10/1991 | Simons |
| 5,058,161 A | 10/1991 | Weiss |
| 5,059,171 A | 10/1991 | Bridge |
| 5,063,603 A | 11/1991 | Burt |
| 5,064,412 A | 11/1991 | Henke et al. |
| 5,078,683 A | 1/1992 | Sancoff et al. |
| 5,084,663 A | 1/1992 | Olsson |

(56) References Cited

U.S. PATENT DOCUMENTS

| | | |
|---|---|---|
| 5,084,828 A | 1/1992 | Kaufman et al. |
| 5,088,981 A | 2/1992 | Howson et al. |
| 5,096,385 A | 3/1992 | Georgi et al. |
| 5,097,505 A | 3/1992 | Weiss |
| 5,100,380 A | 3/1992 | Epstein et al. |
| 5,102,392 A | 4/1992 | Sakai et al. |
| 5,103,211 A | 4/1992 | Daoud et al. |
| 5,104,374 A | 4/1992 | Bishko et al. |
| 5,108,367 A | 4/1992 | Epstein et al. |
| 5,109,850 A | 5/1992 | Blanco et al. |
| 5,116,203 A | 5/1992 | Nartwick et al. |
| 5,116,312 A | 5/1992 | Blakenship et al. |
| 5,116,316 A | 5/1992 | Sertic |
| 5,123,275 A | 6/1992 | Daoud et al. |
| 5,124,627 A | 6/1992 | Okada |
| 5,125,499 A | 6/1992 | Saathoff et al. |
| 5,131,816 A | 7/1992 | Brown |
| 5,132,603 A | 7/1992 | Yoshimoto |
| 5,153,827 A | 10/1992 | Coutre et al. |
| 5,158,441 A | 10/1992 | Aid |
| 5,161,222 A | 11/1992 | Montejo et al. |
| 5,174,472 A | 12/1992 | Raque et al. |
| 5,176,631 A | 1/1993 | Koenig |
| 5,176,646 A | 1/1993 | Kuroda |
| 5,179,340 A | 1/1993 | Rogers |
| 5,180,287 A | 1/1993 | Natwick et al. |
| 5,181,910 A | 1/1993 | Scanlon |
| 5,186,057 A | 2/1993 | Everhart |
| 5,188,603 A | 2/1993 | Vaillancourt |
| 5,190,522 A | 3/1993 | Wocicki et al. |
| 5,191,795 A | 3/1993 | Fellingham et al. |
| 5,192,340 A | 3/1993 | Grant et al. |
| 5,194,796 A | 3/1993 | Domeki et al. |
| 5,198,776 A | 3/1993 | Carr |
| 5,200,090 A | 4/1993 | Ford |
| 5,205,819 A | 4/1993 | Ross et al. |
| 5,206,522 A | 4/1993 | Danby et al. |
| 5,207,642 A | 5/1993 | Orkin et al. |
| 5,211,626 A | 5/1993 | Frank et al. |
| 5,213,573 A | 5/1993 | Sorich et al. |
| 5,215,450 A | 6/1993 | Tamari |
| 5,216,597 A | 6/1993 | Beckers |
| 5,219,099 A | 6/1993 | Spence et al. |
| 5,219,327 A | 6/1993 | Okada |
| 5,221,268 A | 6/1993 | Barton et al. |
| 5,229,713 A | 7/1993 | Bullock et al. |
| 5,232,476 A | 8/1993 | Grant |
| 5,233,571 A | 8/1993 | Wirtschafter |
| 5,237,309 A | 8/1993 | Frantz et al. |
| 5,242,406 A | 9/1993 | Gross et al. |
| 5,242,408 A | 9/1993 | Jhuboo et al. |
| 5,243,982 A | 9/1993 | Möstl et al. |
| 5,244,463 A | 9/1993 | Cordner, Jr. et al. |
| 5,244,568 A | 9/1993 | Lindsay et al. |
| 5,254,096 A | 10/1993 | Rondelet et al. |
| 5,256,155 A | 10/1993 | Yerlikaya et al. |
| 5,256,156 A | 10/1993 | Kern et al. |
| 5,256,157 A | 10/1993 | Samiotes et al. |
| 5,257,206 A * | 10/1993 | Hanson ............... F25J 3/04848 700/32 |
| 5,260,665 A | 11/1993 | Goldberg |
| 5,267,980 A | 12/1993 | Dirr et al. |
| 5,274,316 A | 12/1993 | Evans et al. |
| 5,276,610 A | 1/1994 | Maeda et al. |
| 5,280,728 A | 1/1994 | Sato et al. |
| 5,283,510 A | 2/1994 | Tamaki et al. |
| 5,287,851 A | 2/1994 | Beran et al. |
| 5,292,306 A | 3/1994 | Wynkoop et al. |
| 5,295,967 A | 3/1994 | Rondelet et al. |
| 5,298,021 A | 3/1994 | Sherer |
| 5,303,585 A | 4/1994 | Lichte |
| 5,304,126 A | 4/1994 | Epstein et al. |
| 5,308,333 A | 5/1994 | Skakoon |
| 5,317,506 A | 5/1994 | Coutre et al. |
| 5,319,363 A | 6/1994 | Welch et al. |
| 5,319,979 A | 6/1994 | Abrahamson |
| 5,321,392 A | 6/1994 | Skakoon et al. |
| 5,325,170 A | 6/1994 | Bornhop |
| 5,325,728 A | 7/1994 | Zimmerman et al. |
| 5,328,460 A | 7/1994 | Lord et al. |
| 5,330,634 A | 7/1994 | Wong et al. |
| 5,333,497 A | 8/1994 | Braend et al. |
| 5,336,051 A | 8/1994 | Tamari |
| 5,338,157 A | 8/1994 | Blomquist |
| 5,342,298 A | 8/1994 | Michaels |
| 5,343,734 A | 9/1994 | Maeda et al. |
| 5,343,885 A | 9/1994 | Grant |
| 5,346,466 A | 9/1994 | Yerlikaya et al. |
| 5,356,378 A | 10/1994 | Doan et al. |
| 5,359,271 A | 10/1994 | Husher |
| D352,778 S | 11/1994 | Irvin et al. |
| 5,364,346 A | 11/1994 | Schrezenmeir |
| 5,366,346 A | 11/1994 | Danby |
| 5,368,562 A | 11/1994 | Blomquist et al. |
| 5,374,865 A | 12/1994 | Yoshimura et al. |
| 5,376,070 A | 12/1994 | Purvis et al. |
| 5,378,231 A | 1/1995 | Johnson et al. |
| 5,382,232 A | 1/1995 | Hague et al. |
| 5,383,369 A | 1/1995 | Khuri-Yakub et al. |
| 5,389,071 A | 2/1995 | Kawahara et al. |
| 5,389,078 A | 2/1995 | Zalesky et al. |
| 5,392,638 A | 2/1995 | Kawahara |
| 5,394,732 A | 3/1995 | Johnson et al. |
| 5,395,320 A | 3/1995 | Padda et al. |
| 5,399,171 A | 3/1995 | Bowman et al. |
| 5,406,954 A | 4/1995 | Tomita |
| 5,408,326 A | 4/1995 | Priestley |
| 5,415,528 A | 5/1995 | Ogden et al. |
| 5,417,119 A | 5/1995 | Smoll |
| 5,417,222 A | 5/1995 | Dempsey et al. |
| 5,417,395 A | 5/1995 | Fowler et al. |
| 5,418,443 A | 5/1995 | Kikuchi |
| 5,421,208 A | 6/1995 | Packard et al. |
| 5,423,748 A | 6/1995 | Uhala |
| 5,423,759 A | 6/1995 | Campbell |
| 5,428,284 A | 6/1995 | Kaneda et al. |
| 5,429,485 A | 7/1995 | Dodge |
| 5,429,601 A | 7/1995 | Conley |
| 5,429,602 A | 7/1995 | Hauser |
| 5,431,627 A | 7/1995 | Pastrone et al. |
| 5,434,508 A | 7/1995 | Ishida |
| 5,437,624 A | 8/1995 | Langley et al. |
| 5,444,316 A | 8/1995 | Ohya et al. |
| 5,444,378 A | 8/1995 | Rogers |
| 5,445,621 A | 8/1995 | Poli et al. |
| 5,450,758 A | 9/1995 | Smoll |
| 5,451,881 A | 9/1995 | Finger |
| 5,455,423 A | 10/1995 | Mount et al. |
| 5,455,851 A | 10/1995 | Chaco et al. |
| 5,463,906 A | 11/1995 | Spani et al. |
| 5,464,392 A | 11/1995 | Epstein et al. |
| 5,465,082 A | 11/1995 | Chaco |
| 5,469,851 A | 11/1995 | Lipschutz |
| 5,473,948 A | 12/1995 | Moss et al. |
| 5,480,294 A | 1/1996 | Di Perna et al. |
| 5,482,438 A | 1/1996 | Anderson et al. |
| 5,485,408 A | 1/1996 | Blomquist |
| 5,486,286 A | 1/1996 | Peterson et al. |
| 5,489,265 A | 2/1996 | Montalvo et al. |
| 5,495,566 A | 2/1996 | Kwatinetz |
| 5,496,273 A | 3/1996 | Pastrone et al. |
| 5,505,696 A | 4/1996 | Miki |
| 5,505,828 A | 4/1996 | Wong et al. |
| 5,507,288 A | 4/1996 | Bocker et al. |
| 5,507,412 A | 4/1996 | Ebert et al. |
| 5,520,637 A | 5/1996 | Pager et al. |
| 5,522,798 A | 6/1996 | Johnson et al. |
| 5,522,799 A | 6/1996 | Furukawa |
| 5,527,630 A | 6/1996 | Nagata |
| 5,533,389 A | 7/1996 | Kamen et al. |
| 5,537,853 A | 7/1996 | Finburgh et al. |
| 5,542,040 A | 7/1996 | Chang et al. |
| 5,545,140 A | 8/1996 | Conero et al. |
| 5,547,470 A | 8/1996 | Johnson et al. |

(56) References Cited

U.S. PATENT DOCUMENTS

| | | | |
|---|---|---|---|
| 5,551,850 A | 9/1996 | Williamson et al. |
| 5,554,013 A | 9/1996 | Owens et al. |
| 5,554,115 A | 9/1996 | Thomas et al. |
| 5,558,638 A | 9/1996 | Evers et al. |
| 5,562,615 A | 10/1996 | Nassif |
| 5,563,486 A | 10/1996 | Yamamoto et al. |
| 5,572,105 A | 11/1996 | Nojima et al. |
| 5,573,502 A | 11/1996 | LeCocq et al. |
| 5,583,280 A | 12/1996 | Mo et al. |
| 5,584,667 A | 12/1996 | Davis |
| 5,584,806 A | 12/1996 | Amano |
| 5,586,868 A | 12/1996 | Lawless et al. |
| 5,590,653 A | 1/1997 | Aida et al. |
| 5,594,786 A | 1/1997 | Chaco et al. |
| 5,600,073 A | 2/1997 | Hill |
| 5,601,420 A | 2/1997 | Warner et al. |
| 5,609,575 A | 3/1997 | Larson et al. |
| 5,609,576 A | 3/1997 | Voss |
| 5,611,784 A | 3/1997 | Barresi et al. |
| 5,616,124 A | 4/1997 | Hague et al. |
| 5,620,312 A | 4/1997 | Hyman et al. |
| 5,620,608 A | 4/1997 | Rosa et al. |
| 5,626,140 A * | 5/1997 | Feldman .............. G06K 9/6293 600/483 |
| 5,626,151 A | 5/1997 | Linden |
| 5,626,563 A | 5/1997 | Dodge et al. |
| 5,627,443 A | 5/1997 | Kimura et al. |
| 5,628,309 A | 5/1997 | Brown |
| 5,628,731 A | 5/1997 | Dodge et al. |
| 5,630,710 A | 5/1997 | Tune et al. |
| 5,634,896 A | 6/1997 | Bryant et al. |
| 5,637,095 A | 6/1997 | Nason et al. |
| 5,640,075 A | 6/1997 | Brasseur et al. |
| 5,640,150 A | 6/1997 | Atwater |
| 5,643,212 A | 7/1997 | Coutre et al. |
| 5,648,710 A | 7/1997 | Ikeda |
| 5,649,536 A | 7/1997 | Ogura et al. |
| 5,651,775 A | 7/1997 | Walker et al. |
| 5,657,000 A | 8/1997 | Ellingboe |
| 5,658,133 A | 8/1997 | Anderson et al. |
| 5,658,250 A | 8/1997 | Blomquist et al. |
| 5,659,234 A | 8/1997 | Cresens |
| 5,661,245 A | 8/1997 | Svoboda et al. |
| 5,662,612 A | 9/1997 | Niehoff |
| 5,665,065 A | 9/1997 | Colman et al. |
| 5,669,877 A | 9/1997 | Blomquist |
| 5,672,154 A | 9/1997 | Sillén et al. |
| 5,672,832 A | 9/1997 | Cucci et al. |
| 5,681,285 A | 10/1997 | Ford et al. |
| 5,681,286 A | 10/1997 | Niehoff |
| 5,685,844 A | 11/1997 | Marttila |
| 5,687,717 A | 11/1997 | Halpern et al. |
| 5,689,229 A | 11/1997 | Chaco et al. |
| 5,691,613 A | 11/1997 | Gutwillinger |
| 5,695,464 A | 12/1997 | Viallet |
| 5,695,473 A | 12/1997 | Olsen |
| 5,697,899 A | 12/1997 | Hillman et al. |
| 5,697,916 A | 12/1997 | Schraga |
| 5,712,795 A | 1/1998 | Layman et al. |
| 5,713,856 A | 2/1998 | Eggers et al. |
| 5,714,691 A | 2/1998 | Hill |
| 5,718,562 A | 2/1998 | Lawless et al. |
| 5,718,569 A | 2/1998 | Holst |
| 5,720,721 A | 2/1998 | Dumas et al. |
| 5,722,417 A | 3/1998 | Rudolph |
| 5,728,074 A | 3/1998 | Castellano et al. |
| 5,728,948 A | 3/1998 | Bignell et al. |
| 5,733,257 A | 3/1998 | Stemby |
| 5,733,259 A | 3/1998 | Valcke et al. |
| 5,738,659 A | 4/1998 | Neer et al. |
| 5,743,856 A | 4/1998 | Oka et al. |
| 5,744,027 A | 4/1998 | Connell et al. |
| 5,744,929 A | 4/1998 | Miyazaki |
| 5,745,378 A | 4/1998 | Barker et al. |
| 5,752,813 A | 5/1998 | Tyner et al. |
| 5,752,918 A | 5/1998 | Fowler et al. |
| 5,752,919 A | 5/1998 | Schrimpf |
| 5,755,691 A | 5/1998 | Hilborne |
| 5,758,643 A | 6/1998 | Wong et al. |
| 5,761,072 A | 6/1998 | Bardsley, Jr. et al. |
| 5,764,034 A | 6/1998 | Bowman et al. |
| 5,766,155 A | 6/1998 | Hyman et al. |
| 5,772,635 A | 6/1998 | Dastur et al. |
| 5,778,256 A | 7/1998 | Darbee |
| 5,781,442 A | 7/1998 | Engleson et al. |
| 5,782,805 A | 7/1998 | Meinzer et al. |
| 5,788,669 A | 8/1998 | Peterson |
| 5,788,674 A | 8/1998 | McWilliams |
| 5,789,923 A | 8/1998 | Shimoyama et al. |
| 5,792,069 A | 8/1998 | Greenwald et al. |
| 5,793,211 A | 8/1998 | Shimoyama et al. |
| 5,795,327 A | 8/1998 | Wilson et al. |
| 5,798,934 A | 8/1998 | Saigo et al. |
| 5,800,387 A | 9/1998 | Duffy et al. |
| 5,803,712 A | 9/1998 | Davis et al. |
| 5,803,917 A | 9/1998 | Butterfield |
| 5,805,455 A | 9/1998 | Lipps |
| 5,807,322 A | 9/1998 | Lindsey et al. |
| 5,810,770 A | 9/1998 | Chin et al. |
| 5,813,972 A | 9/1998 | Nazarian et al. |
| 5,814,004 A | 9/1998 | Tamari |
| 5,814,015 A | 9/1998 | Gargano et al. |
| 5,816,779 A | 10/1998 | Lawless et al. |
| 5,822,715 A | 10/1998 | Worthington et al. |
| 5,827,179 A | 10/1998 | Lichter et al. |
| 5,827,223 A | 10/1998 | Butterfield |
| 5,832,448 A | 11/1998 | Brown |
| 5,836,910 A | 11/1998 | Duffy et al. |
| 5,841,261 A | 11/1998 | Nojima et al. |
| 5,841,284 A | 11/1998 | Takahashi |
| 5,843,035 A | 12/1998 | Bowman |
| 5,848,971 A | 12/1998 | Fowler et al. |
| 5,850,344 A | 12/1998 | Conkright |
| 5,857,843 A | 1/1999 | Leason et al. |
| 5,864,330 A | 1/1999 | Haynes |
| 5,865,805 A | 2/1999 | Ziemba |
| 5,867,821 A | 2/1999 | Ballantyne et al. |
| 5,871,465 A | 2/1999 | Vasko |
| 5,872,453 A | 2/1999 | Shimoyama et al. |
| 5,875,195 A | 2/1999 | Dixon |
| 5,882,300 A | 3/1999 | Malinouskas et al. |
| 5,882,339 A | 3/1999 | Beiser et al. |
| 5,885,245 A | 3/1999 | Lynch et al. |
| 5,889,379 A | 3/1999 | Yanagi et al. |
| 5,891,051 A | 4/1999 | Han et al. |
| 5,894,209 A | 4/1999 | Takagi et al. |
| 5,897,493 A | 4/1999 | Brown |
| 5,897,498 A | 4/1999 | Canfield, II et al. |
| 5,898,292 A | 4/1999 | Takemoto et al. |
| 5,899,665 A | 5/1999 | Makino et al. |
| 5,901,150 A | 5/1999 | Jhuboo et al. |
| 5,904,666 A | 5/1999 | DeDecker et al. |
| 5,904,668 A | 5/1999 | Hyman et al. |
| 5,905,207 A | 5/1999 | Schalk |
| 5,906,598 A | 5/1999 | Giesier |
| 5,910,252 A | 6/1999 | Truitt et al. |
| 5,915,240 A | 6/1999 | Karpf |
| 5,920,263 A | 7/1999 | Huttenhoff et al. |
| 5,923,159 A | 7/1999 | Ezell |
| 5,924,074 A | 7/1999 | Evans |
| 5,927,349 A | 7/1999 | Martucci |
| 5,932,119 A | 8/1999 | Kaplan et al. |
| 5,932,987 A | 8/1999 | McLoughlin |
| 5,935,099 A | 8/1999 | Peterson et al. |
| 5,935,106 A | 8/1999 | Olsen |
| 5,938,634 A | 8/1999 | Packard |
| 5,938,636 A | 8/1999 | Kramer et al. |
| 5,941,846 A | 8/1999 | Duffy et al. |
| 5,944,660 A | 8/1999 | Kimball et al. |
| 5,947,911 A | 9/1999 | Wong et al. |
| 5,954,527 A | 9/1999 | Jhuboo et al. |
| 5,954,696 A | 9/1999 | Ryan et al. |
| 5,956,023 A | 9/1999 | Lyle et al. |
| 5,956,501 A | 9/1999 | Brown |

(56) References Cited

U.S. PATENT DOCUMENTS

| | | | |
|---|---|---|---|
| 5,957,885 | A | 9/1999 | Bollish et al. |
| 5,957,890 | A | 9/1999 | Mann et al. |
| 5,971,594 | A | 10/1999 | Sahai et al. |
| 5,973,497 | A | 10/1999 | Bergk et al. |
| 5,975,081 | A | 11/1999 | Hood et al. |
| 5,989,222 | A | 11/1999 | Cole et al. |
| 5,990,838 | A | 11/1999 | Burns et al. |
| 5,991,525 | A | 11/1999 | Shah et al. |
| 5,993,393 | A | 11/1999 | Ryan et al. |
| 5,994,876 | A | 11/1999 | Canny et al. |
| 5,997,476 | A | 12/1999 | Brown |
| 6,000,828 | A | 12/1999 | Leet |
| 6,003,006 | A | 12/1999 | Colella et al. |
| 6,003,388 | A | 12/1999 | Oeftering |
| 6,012,034 | A | 1/2000 | Hamparian et al. |
| 6,017,318 | A | 1/2000 | Gauthier et al. |
| 6,017,493 | A | 1/2000 | Cambron |
| 6,021,392 | A | 2/2000 | Lester et al. |
| 6,023,977 | A | 2/2000 | Langdon et al. |
| 6,024,539 | A | 2/2000 | Blomquist |
| 6,027,441 | A | 2/2000 | Cantu |
| 6,032,676 | A | 3/2000 | Moore |
| 6,033,561 | A | 3/2000 | Schoendorfer |
| 6,036,017 | A | 3/2000 | Bayliss, IV |
| 6,068,612 | A | 5/2000 | Bowman |
| 6,068,615 | A | 5/2000 | Brown et al. |
| 6,073,106 | A | 6/2000 | Rozen et al. |
| 6,077,246 | A | 6/2000 | Kullas et al. |
| 6,083,206 | A | 7/2000 | Molko |
| 6,089,104 | A | 7/2000 | Chang |
| 6,104,295 | A | 8/2000 | Gaisser et al. |
| 6,110,152 | A | 8/2000 | Kovelman |
| 6,110,153 | A | 8/2000 | Davis |
| RE36,871 | E | 9/2000 | Epstein et al. |
| 6,120,459 | A | 9/2000 | Nitzan et al. |
| 6,122,536 | A | 9/2000 | Sun et al. |
| 6,142,008 | A | 11/2000 | Cole et al. |
| 6,150,942 | A | 11/2000 | O'Brien |
| 6,157,914 | A | 12/2000 | Seto et al. |
| 6,158,288 | A | 12/2000 | Smith |
| 6,158,965 | A | 12/2000 | Butterfield et al. |
| 6,159,147 | A | 12/2000 | Lichter et al. |
| 6,159,186 | A | 12/2000 | Wickham et al. |
| 6,164,921 | A | 12/2000 | Moubayed et al. |
| 6,168,561 | B1 | 1/2001 | Cantu |
| 6,178,827 | B1 | 1/2001 | Feller |
| 6,182,667 | B1 | 2/2001 | Hanks et al. |
| 6,186,141 | B1 | 2/2001 | Pike et al. |
| 6,189,105 | B1 | 2/2001 | Lopes |
| 6,192,752 | B1 | 2/2001 | Blaine |
| 6,195,589 | B1 | 2/2001 | Ketcham |
| 6,202,711 | B1 | 3/2001 | Maducci |
| 6,203,528 | B1 | 3/2001 | Deckert |
| 6,208,107 | B1 | 3/2001 | Maske et al. |
| 6,212,936 | B1 | 4/2001 | Meisberger |
| 6,213,972 | B1 | 4/2001 | Butterfield |
| 6,231,320 | B1 | 5/2001 | Lawless et al. |
| 6,234,176 | B1 | 5/2001 | Domae et al. |
| 6,236,326 | B1 | 5/2001 | Murphy et al. |
| 6,237,398 | B1 | 5/2001 | Porat et al. |
| 6,241,704 | B1 | 6/2001 | Peterson et al. |
| 6,248,067 | B1 | 6/2001 | Causey, III et al. |
| 6,250,132 | B1 | 6/2001 | Drzewiecki |
| 6,259,355 | B1 | 7/2001 | Chaco et al. |
| 6,259,587 | B1 | 7/2001 | Sheldon et al. |
| 6,261,065 | B1 | 7/2001 | Nayak |
| 6,262,946 | B1 | 7/2001 | Khuri-Yakub et al. |
| 6,267,559 | B1 | 7/2001 | Mossman et al. |
| 6,267,725 | B1 | 7/2001 | Dubberstein et al. |
| 6,269,340 | B1 | 7/2001 | Ford et al. |
| 6,270,455 | B1 | 8/2001 | Brown |
| 6,271,813 | B1 | 8/2001 | Palalau |
| 6,277,072 | B1 | 8/2001 | Bardy |
| 6,277,099 | B1 | 8/2001 | Strowe et al. |
| 6,280,380 | B1 | 8/2001 | Bardy |
| 6,280,391 | B1 | 8/2001 | Olson et al. |
| 6,280,408 | B1 | 8/2001 | Sipin |
| 6,283,761 | B1 | 9/2001 | Joao |
| 6,285,155 | B1 | 9/2001 | Maske et al. |
| 6,312,378 | B1 | 11/2001 | Bardy |
| 6,322,516 | B1 | 11/2001 | Masuda et al. |
| 6,330,351 | B1 | 12/2001 | Yasunaga |
| 6,337,675 | B1 | 1/2002 | Toffolo et al. |
| 6,345,539 | B1 | 2/2002 | Rawes et al. |
| 6,347,553 | B1 | 2/2002 | Morris et al. |
| 6,349,740 | B1 | 2/2002 | Cho et al. |
| 6,358,225 | B1 | 3/2002 | Butterfield |
| 6,358,387 | B1 | 3/2002 | Kopf-Sill et al. |
| 6,362,591 | B1 | 3/2002 | Moberg |
| 6,385,505 | B1 | 5/2002 | Lipps |
| 6,386,050 | B1 | 5/2002 | Yin et al. |
| 6,394,958 | B1 | 5/2002 | Bratteli et al. |
| 6,396,583 | B1 | 5/2002 | Clare |
| 6,398,760 | B1 | 6/2002 | Danby |
| 6,405,076 | B1 | 6/2002 | Taylor et al. |
| 6,408,679 | B1 | 6/2002 | Kline-Schoder et al. |
| 6,413,238 | B1 | 7/2002 | Maget |
| 6,416,291 | B1 | 7/2002 | Butterfield et al. |
| 6,418,334 | B1 | 7/2002 | Unger et al. |
| 6,418,535 | B1 | 7/2002 | Kulakowski et al. |
| 6,445,053 | B1 | 9/2002 | Cho |
| 6,456,245 | B1 | 9/2002 | Crawford |
| 6,457,346 | B1 | 10/2002 | Kline-Schoder et al. |
| 6,463,785 | B1 | 10/2002 | Kline-Schoder et al. |
| 6,467,331 | B1 | 10/2002 | Kline-Schoder et al. |
| 6,468,242 | B1 | 10/2002 | Wilson et al. |
| 6,475,178 | B1 | 11/2002 | Krajewski |
| 6,481,980 | B1 | 11/2002 | Vandlik |
| 6,482,158 | B2 | 11/2002 | Mault |
| 6,482,185 | B1 | 11/2002 | Hartmann |
| 6,485,263 | B1 | 11/2002 | Bryant et al. |
| 6,485,418 | B2 | 11/2002 | Yasushi et al. |
| 6,485,465 | B2 | 11/2002 | Moberg et al. |
| 6,487,916 | B1 | 12/2002 | Gomm et al. |
| 6,489,896 | B1 | 12/2002 | Platt |
| 6,494,694 | B2 | 12/2002 | Lawless et al. |
| 6,494,831 | B1 | 12/2002 | Koritzinsky |
| 6,497,680 | B1 | 12/2002 | Holst et al. |
| 6,503,221 | B1 | 1/2003 | Briggs |
| 6,512,944 | B1 | 1/2003 | Kovtun et al. |
| 6,516,667 | B1 | 2/2003 | Broad et al. |
| 6,517,482 | B1 | 2/2003 | Eiden et al. |
| 6,519,569 | B1 | 2/2003 | White et al. |
| 6,529,751 | B1 | 3/2003 | Van Driel et al. |
| 6,531,708 | B1 | 3/2003 | Malmstrom |
| 6,539,315 | B1 | 3/2003 | Adams et al. |
| 6,540,672 | B1 | 4/2003 | Simonsen et al. |
| 6,544,212 | B2 | 4/2003 | Galley et al. |
| 6,544,228 | B1 | 4/2003 | Heitmeier |
| 6,558,125 | B1 | 5/2003 | Futterknecht |
| 6,558,351 | B1 | 5/2003 | Steil et al. |
| 6,562,012 | B1 | 5/2003 | Brown et al. |
| 6,564,825 | B2 | 5/2003 | Lowery et al. |
| 6,565,509 | B1 | 5/2003 | Say et al. |
| 6,568,416 | B2 | 5/2003 | Tucker et al. |
| 6,572,542 | B1 | 6/2003 | Houben et al. |
| 6,572,545 | B2 | 6/2003 | Knobbe et al. |
| 6,572,576 | B2 | 6/2003 | Brugger et al. |
| 6,578,422 | B2 | 6/2003 | Lam et al. |
| 6,578,435 | B2 | 6/2003 | Gould et al. |
| 6,581,117 | B1 | 6/2003 | Klein et al. |
| RE38,189 | E | 7/2003 | Walker et al. |
| 6,585,675 | B1 | 7/2003 | O'Mahony et al. |
| 6,589,229 | B1 | 7/2003 | Connelly et al. |
| 6,589,792 | B1 | 7/2003 | Malachowski |
| 6,599,281 | B1 | 7/2003 | Struys et al. |
| 6,599,282 | B2 | 7/2003 | Burko |
| 6,602,191 | B2 | 8/2003 | Quy |
| 6,605,072 | B2 | 8/2003 | Struys et al. |
| 6,609,047 | B1 | 8/2003 | Lipps |
| 6,615,674 | B2 | 9/2003 | Ohnishi |
| 6,616,633 | B1 | 9/2003 | Butterfield et al. |
| 6,617,564 | B2 | 9/2003 | Ockerse et al. |
| 6,618,916 | B1 | 9/2003 | Eberle et al. |

(56) References Cited

U.S. PATENT DOCUMENTS

| | | |
|---|---|---|
| 6,622,542 B2 | 9/2003 | Derek |
| 6,622,561 B2 | 9/2003 | Lam et al. |
| D481,121 S | 10/2003 | Evans |
| 6,629,449 B1 | 10/2003 | Kline-Schoder et al. |
| 6,634,233 B2 | 10/2003 | He |
| 6,640,246 B1 | 10/2003 | Gardy, Jr. et al. |
| 6,641,533 B2 | 11/2003 | Causey, III et al. |
| 6,641,541 B1 | 11/2003 | Lovett et al. |
| 6,648,861 B2 | 11/2003 | Platt et al. |
| 6,652,455 B1 | 11/2003 | Kocher |
| 6,653,937 B2 | 11/2003 | Nelson et al. |
| 6,659,980 B2 | 12/2003 | Moberg et al. |
| D485,356 S | 1/2004 | Evans |
| 6,685,668 B1 | 2/2004 | Cho et al. |
| 6,685,678 B2 | 2/2004 | Evans et al. |
| 6,689,069 B2 | 2/2004 | Bratteli et al. |
| 6,689,091 B2 | 2/2004 | Bui et al. |
| 6,692,241 B2 | 2/2004 | Watanabe et al. |
| 6,716,004 B2 | 4/2004 | Vandlik |
| 6,719,535 B2 | 4/2004 | Rakestraw et al. |
| 6,721,582 B2 | 4/2004 | Trepagnier et al. |
| 6,722,211 B1 | 4/2004 | Ciobanu et al. |
| 6,725,200 B1 | 4/2004 | Rost |
| 6,725,721 B2 | 4/2004 | Venczel |
| 6,731,989 B2 | 5/2004 | Engleson et al. |
| 6,732,595 B2 | 5/2004 | Lynnworth |
| 6,738,052 B1 | 5/2004 | Manke et al. |
| 6,740,072 B2 | 5/2004 | Starkweather et al. |
| 6,741,212 B2 | 5/2004 | Kralovec et al. |
| 6,748,808 B2 | 6/2004 | Lam et al. |
| 6,749,403 B2 | 6/2004 | Bryant et al. |
| 6,752,787 B1 | 6/2004 | Causey, III et al. |
| 6,753,842 B1 | 6/2004 | Williams et al. |
| 6,759,007 B1 | 7/2004 | Westberg |
| 6,760,643 B2 | 7/2004 | Lipps |
| 6,768,920 B2 | 7/2004 | Lange |
| 6,773,412 B2 | 8/2004 | O'Mahony |
| 6,780,156 B2 | 8/2004 | Haueter et al. |
| 6,783,328 B2 | 8/2004 | Lucke et al. |
| 6,785,573 B2 | 8/2004 | Kovtun et al. |
| 6,786,885 B2 | 9/2004 | Hochman et al. |
| 6,789,426 B2 | 9/2004 | Yaralioglu et al. |
| 6,790,198 B1 | 9/2004 | White et al. |
| 6,793,625 B2 | 9/2004 | Cavallaro et al. |
| 6,801,227 B2 | 10/2004 | Bocionek et al. |
| 6,805,671 B2 | 10/2004 | Stergiopoulos et al. |
| 6,807,965 B1 | 10/2004 | Hickle |
| 6,809,653 B1 | 10/2004 | Mann et al. |
| 6,813,964 B1 | 11/2004 | Clark et al. |
| 6,814,547 B2 | 11/2004 | Childers |
| 6,824,528 B1 | 11/2004 | Faries |
| 6,830,558 B2 | 12/2004 | Flaherty et al. |
| 6,840,113 B2 | 1/2005 | Fukumura et al. |
| 6,846,161 B2 | 1/2005 | Kline |
| 6,852,094 B2 | 2/2005 | Beck |
| 6,852,104 B2 | 2/2005 | Blomquist |
| 6,854,338 B2 | 2/2005 | Khuri-Yakub et al. |
| 6,857,318 B1 | 2/2005 | Silber et al. |
| 6,869,425 B2 | 3/2005 | Briggs et al. |
| 6,873,268 B2 | 3/2005 | Lebel et al. |
| 6,883,376 B2 | 4/2005 | He |
| 6,885,881 B2 | 4/2005 | Leonhardt |
| 6,887,216 B2 | 5/2005 | Hochman et al. |
| 6,898,301 B2 | 5/2005 | Iwanaga |
| 6,907,361 B2 | 6/2005 | Molenaar |
| 6,907,792 B2 | 6/2005 | Ohnishi |
| 6,915,170 B2 | 7/2005 | Engleson et al. |
| 6,920,795 B2 | 7/2005 | Bischoff et al. |
| 6,923,763 B1 | 8/2005 | Kovatchev et al. |
| 6,928,338 B1 | 8/2005 | Buchser et al. |
| 6,929,619 B2 | 8/2005 | Fago et al. |
| 6,929,751 B2 | 8/2005 | Bowman |
| 6,932,114 B2 | 8/2005 | Sparks |
| 6,932,796 B2 | 8/2005 | Sage et al. |
| 6,935,192 B2 | 8/2005 | Sobek et al. |
| 6,936,029 B2 | 8/2005 | Mann et al. |
| 6,941,005 B2 | 9/2005 | Lary et al. |
| 6,942,636 B2 | 9/2005 | Holst et al. |
| 6,945,954 B2 | 9/2005 | Hochman et al. |
| 6,958,705 B2 | 10/2005 | Lebel et al. |
| 6,964,204 B2 | 11/2005 | Clark et al. |
| 6,973,374 B2 | 12/2005 | Ader |
| 6,974,437 B2 | 12/2005 | Lebel et al. |
| 6,975,922 B2 | 12/2005 | Duncan et al. |
| 6,978,779 B2 | 12/2005 | Haveri et al. |
| 6,979,326 B2 | 12/2005 | Mann et al. |
| 6,981,960 B2 | 1/2006 | Cho et al. |
| 6,984,218 B2 | 1/2006 | Nayak et al. |
| 6,985,768 B2 | 1/2006 | Hemming et al. |
| 6,985,870 B2 | 1/2006 | Martucci et al. |
| 6,986,347 B2 | 1/2006 | Hickle |
| 6,986,753 B2 | 1/2006 | Bui |
| 6,997,905 B2 | 2/2006 | Gillespie, Jr. et al. |
| 6,997,920 B2 | 2/2006 | Mann et al. |
| 7,006,005 B2 | 2/2006 | Nazarian et al. |
| 7,017,623 B2 | 3/2006 | Tribble et al. |
| 7,021,148 B2 | 4/2006 | Kuhn |
| 7,025,743 B2 | 4/2006 | Mann et al. |
| 7,029,455 B2 | 4/2006 | Flaherty |
| 7,029,456 B2 | 4/2006 | Ware et al. |
| 7,059,184 B2 | 6/2006 | Kanouola et al. |
| 7,060,059 B2 | 6/2006 | Keith et al. |
| 7,069,793 B2 | 7/2006 | Ishikawa et al. |
| 7,072,725 B2 | 7/2006 | Bristol et al. |
| 7,074,209 B2 | 7/2006 | Evans et al. |
| 7,080,557 B2 | 7/2006 | Adnan |
| 7,082,843 B2 | 8/2006 | Clark et al. |
| 7,087,444 B2 | 8/2006 | Wong et al. |
| 7,092,796 B2 | 8/2006 | Vanderveen |
| 7,092,797 B2 | 8/2006 | Gaines et al. |
| 7,093,502 B2 | 8/2006 | Kupnik et al. |
| 7,096,729 B2 | 8/2006 | Repko et al. |
| 7,103,419 B2 | 9/2006 | Engleson et al. |
| 7,104,763 B2 | 9/2006 | Bouton et al. |
| 7,104,769 B2 | 9/2006 | Davis |
| 7,108,680 B2 | 9/2006 | Rohr et al. |
| 7,109,878 B2 | 9/2006 | Mann et al. |
| 7,115,113 B2 | 10/2006 | Evans et al. |
| 7,117,041 B2 | 10/2006 | Engleson et al. |
| 7,137,964 B2 | 11/2006 | Flaherty |
| 7,141,037 B2 | 11/2006 | Butterfield et al. |
| 7,152,490 B1 | 12/2006 | Freund, Jr. et al. |
| 7,154,397 B2 | 12/2006 | Zerhusen et al. |
| 7,161,488 B2 | 1/2007 | Frasch |
| 7,162,290 B1 | 1/2007 | Levin |
| 7,162,927 B1 | 1/2007 | Selvan et al. |
| 7,171,277 B2 | 1/2007 | Engleson et al. |
| 7,174,789 B2 | 2/2007 | Orr et al. |
| 7,185,288 B2 | 2/2007 | McKeever |
| 7,197,943 B2 | 4/2007 | Lee et al. |
| 7,201,734 B2 | 4/2007 | Hickle |
| 7,204,823 B2 | 4/2007 | Estes et al. |
| 7,206,715 B2 | 4/2007 | Vanderveen et al. |
| 7,213,009 B2 | 5/2007 | Pestotnik |
| 7,220,240 B2 | 5/2007 | Struys et al. |
| 7,229,430 B2 | 6/2007 | Hickle et al. |
| 7,230,529 B2 | 6/2007 | Ketcherside |
| 7,232,430 B2 | 6/2007 | Carlisle |
| 7,238,164 B2 | 7/2007 | Childers et al. |
| 7,247,154 B2 | 7/2007 | Hickle |
| 7,253,779 B2 | 8/2007 | Greer et al. |
| 7,254,425 B2 | 8/2007 | Lowery et al. |
| 7,258,534 B2 | 8/2007 | Fathallah et al. |
| 7,267,664 B2 | 9/2007 | Rizzo |
| 7,267,665 B2 | 9/2007 | Steil et al. |
| 7,272,529 B2 | 9/2007 | Hogan et al. |
| 7,278,983 B2 | 10/2007 | Ireland et al. |
| 7,291,123 B2 | 11/2007 | Baraldi et al. |
| 7,293,461 B1 | 11/2007 | Girndt |
| 7,294,109 B2 | 11/2007 | Lovett et al. |
| 7,296,482 B2 | 11/2007 | Schaffer et al. |
| 7,300,418 B2 | 11/2007 | Zaleski |
| 7,305,883 B2 | 12/2007 | Khuri-Yakub et al. |
| 7,327,273 B2 | 2/2008 | Hung et al. |

(56) References Cited

U.S. PATENT DOCUMENTS

| | | |
|---|---|---|
| 7,338,470 B2 | 3/2008 | Katz |
| 7,347,836 B2 | 3/2008 | Peterson et al. |
| 7,354,420 B2 | 4/2008 | Steil et al. |
| 7,356,382 B2 | 4/2008 | Vanderveen |
| 7,360,999 B2 | 4/2008 | Nelson et al. |
| 7,364,562 B2 | 4/2008 | Braig et al. |
| 7,367,942 B2 | 5/2008 | Grage et al. |
| 7,369,948 B1 | 5/2008 | Ferenczi et al. |
| 7,384,410 B2 | 6/2008 | Eggers et al. |
| 7,397,166 B1 | 7/2008 | Morgan et al. |
| 7,398,183 B2 | 7/2008 | Holland et al. |
| 7,399,277 B2 | 7/2008 | Saidara et al. |
| 7,402,153 B2 | 7/2008 | Steil et al. |
| 7,402,154 B2 | 7/2008 | Mendez |
| 7,407,489 B2 | 8/2008 | Mendez |
| 7,414,534 B1 | 8/2008 | Kroll et al. |
| 7,415,895 B2 | 8/2008 | Kurisaki et al. |
| 7,426,443 B2 | 9/2008 | Simon |
| 7,430,675 B2 | 9/2008 | Lee et al. |
| 7,447,566 B2 | 11/2008 | Knauper et al. |
| 7,447,643 B1 | 11/2008 | Olson |
| 7,452,190 B2 | 11/2008 | Bouton et al. |
| 7,454,314 B2 | 11/2008 | Holland et al. |
| 7,471,994 B2 | 12/2008 | Ford et al. |
| 7,482,818 B2 | 1/2009 | Greenwald et al. |
| 7,483,756 B2 | 1/2009 | Engleson et al. |
| 7,490,021 B2 | 2/2009 | Holland et al. |
| 7,491,187 B2 | 2/2009 | Van Den Berghe et al. |
| 7,503,903 B2 | 3/2009 | Carlisle et al. |
| 7,517,332 B2 | 4/2009 | Tonelli et al. |
| 7,523,401 B1 | 4/2009 | Aldridge |
| 7,545,075 B2 | 6/2009 | Huang et al. |
| 7,556,616 B2 | 7/2009 | Fathallah et al. |
| 7,561,986 B2 | 7/2009 | Vanderveen et al. |
| 7,571,024 B2 | 8/2009 | Duncan et al. |
| 7,645,258 B2 | 1/2010 | White et al. |
| 7,654,127 B2 | 2/2010 | Krulevitch et al. |
| 7,657,443 B2 | 2/2010 | Crass |
| 7,668,731 B2 | 2/2010 | Martucci et al. |
| 7,678,048 B1 | 3/2010 | Urbano et al. |
| 7,693,697 B2 | 4/2010 | Westenkow et al. |
| 7,699,806 B2 | 4/2010 | Ware et al. |
| 7,705,727 B2 | 4/2010 | Pestotnik |
| 7,766,873 B2 | 8/2010 | Moberg et al. |
| 7,775,126 B2 | 8/2010 | Eckhardt |
| 7,775,127 B2 | 8/2010 | Wade |
| 7,785,284 B2 | 8/2010 | Baralsi et al. |
| 7,785,313 B2 | 8/2010 | Mastrototaro |
| 7,786,909 B2 | 8/2010 | Udupa et al. |
| 7,806,886 B2 | 10/2010 | Kanderian, Jr. et al. |
| 7,826,981 B2 | 11/2010 | Goode, Jr. et al. |
| 7,847,276 B2 | 12/2010 | Carlisle |
| 7,860,583 B2 | 12/2010 | Condurso et al. |
| 7,871,394 B2 | 1/2011 | Halbert et al. |
| 7,876,443 B2 | 1/2011 | Bernacki |
| 7,895,053 B2 | 2/2011 | Holland et al. |
| 7,895,882 B2 | 3/2011 | Carlisle |
| 7,896,834 B2 | 3/2011 | Smisson, III |
| 7,896,842 B2 | 3/2011 | Palmroos et al. |
| 7,905,710 B2 | 3/2011 | Wang et al. |
| 7,933,780 B2 | 4/2011 | de la Huerga |
| 7,945,452 B2 | 5/2011 | Fathallah et al. |
| 7,981,073 B2 | 7/2011 | Mollstam |
| 7,981,082 B2 | 7/2011 | Wang et al. |
| 8,034,020 B2 | 10/2011 | Dewey |
| 8,038,593 B2 | 10/2011 | Friedman et al. |
| 8,065,161 B2 | 11/2011 | Howard et al. |
| 8,067,760 B2 | 11/2011 | Carlisle |
| 8,075,546 B2 | 12/2011 | Carlisle et al. |
| 8,078,983 B2 | 12/2011 | Davis et al. |
| 8,121,857 B2 | 2/2012 | Galasso et al. |
| 8,149,131 B2 | 4/2012 | Blornquist |
| 8,175,668 B1 | 5/2012 | Nabutovsky et al. |
| 8,177,739 B2 | 5/2012 | Cartledge et al. |
| 8,185,322 B2 | 5/2012 | Schroeder et al. |
| 8,219,413 B2 | 7/2012 | Martinez et al. |
| 8,226,597 B2 | 7/2012 | Jacobson et al. |
| 8,231,578 B2 | 7/2012 | Fathallah et al. |
| 8,234,128 B2 | 7/2012 | Martucci et al. |
| 8,271,106 B2 | 9/2012 | Wehba et al. |
| 8,287,514 B2 | 10/2012 | Miller et al. |
| 8,291,337 B2 | 10/2012 | Gannin et al. |
| 8,313,308 B2 | 11/2012 | Lawless et al. |
| 8,317,698 B2 | 11/2012 | Lowery |
| 8,317,750 B2 | 11/2012 | Ware et al. |
| 8,317,752 B2 | 11/2012 | Cozmi et al. |
| 8,318,094 B1 | 11/2012 | Bayandorian et al. |
| 8,340,792 B2 | 12/2012 | Condurso et al. |
| 8,347,731 B2 | 1/2013 | Genosar |
| 8,359,338 B2 | 1/2013 | Butterfield et al. |
| 8,361,021 B2 | 1/2013 | Wang et al. |
| 8,378,837 B2 | 2/2013 | Wang et al. |
| 8,388,598 B2 | 3/2013 | Steinkogler |
| 8,398,616 B2 | 3/2013 | Budiman |
| 8,403,908 B2 | 3/2013 | Jacobson et al. |
| 8,449,524 B2 | 5/2013 | Braig et al. |
| 8,477,307 B1 | 7/2013 | Yufa et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,539,812 B2 | 9/2013 | Stringham et al. |
| 8,543,416 B2 | 9/2013 | Palmroos et al. |
| 8,577,692 B2 | 11/2013 | Silkaitis et al. |
| 8,622,990 B2 | 1/2014 | Estes et al. |
| 8,630,722 B2 | 1/2014 | Condurso et al. |
| 8,665,214 B2 | 3/2014 | Forutanpour et al. |
| 8,666,769 B2 | 3/2014 | Butler et al. |
| 8,700,421 B2 | 4/2014 | Feng et al. |
| 8,706,233 B2 | 4/2014 | Su et al. |
| 8,721,584 B2 | 5/2014 | Braithwaite et al. |
| 8,761,906 B2 | 6/2014 | Condurso et al. |
| 8,768,719 B2 | 7/2014 | Wehba et al. |
| 8,771,251 B2 | 7/2014 | Ruchti et al. |
| 8,792,981 B2 | 7/2014 | Yudovsky et al. |
| 8,821,432 B2 | 9/2014 | Unverdorben |
| 8,823,382 B2 | 9/2014 | Rondoni et al. |
| 8,857,269 B2 | 10/2014 | Johnson et al. |
| 8,858,185 B2 | 10/2014 | Johnson et al. |
| 8,964,185 B1 | 2/2015 | Luo et al. |
| 9,005,150 B2 | 4/2015 | Ware et al. |
| 9,026,370 B2 | 5/2015 | Rubalcaba et al. |
| 9,084,855 B2 | 7/2015 | Ware et al. |
| 9,114,217 B2 | 8/2015 | Sur et al. |
| 9,134,735 B2 | 9/2015 | Lowery et al. |
| 9,134,736 B2 | 9/2015 | Lowery et al. |
| 9,138,526 B2 | 9/2015 | Ware et al. |
| 9,190,010 B2 | 11/2015 | Vik et al. |
| 9,240,002 B2 | 1/2016 | Hume et al. |
| 9,272,089 B2 | 3/2016 | Jacobson et al. |
| 9,333,291 B2 | 5/2016 | Jacobson et al. |
| 9,381,296 B2 | 7/2016 | Arrizza et al. |
| 9,393,362 B2 | 7/2016 | Cozmi et al. |
| 9,468,718 B2 | 10/2016 | Hung et al. |
| 9,498,583 B2 | 11/2016 | Sur et al. |
| 9,707,341 B2 | 7/2017 | Dumas, III et al. |
| 9,943,269 B2 | 4/2018 | Muhsin et al. |
| 9,995,611 B2 | 6/2018 | Ruchti et al. |
| 10,022,498 B2 | 7/2018 | Ruchti et al. |
| 10,046,112 B2 | 8/2018 | Oruklu et al. |
| 10,089,055 B1 | 10/2018 | Fryman |
| 10,166,328 B2 | 1/2019 | Oruklu et al. |
| 2001/0007636 A1 | 7/2001 | Butterfield |
| 2001/0014769 A1 | 8/2001 | Bufe et al. |
| 2001/0015099 A1 | 8/2001 | Blaine |
| 2001/0016056 A1 | 8/2001 | Westphal et al. |
| 2001/0032099 A1 | 10/2001 | Joao |
| 2001/0037060 A1 | 11/2001 | Thompson et al. |
| 2001/0041869 A1 | 11/2001 | Causey et al. |
| 2001/0044731 A1 | 11/2001 | Coffman et al. |
| 2002/0003892 A1 | 1/2002 | Iwanaga |
| 2002/0007116 A1 | 1/2002 | Zatezalo et al. |
| 2002/0013545 A1 | 1/2002 | Soltanpour et al. |
| 2002/0013551 A1 | 1/2002 | Zaitsu et al. |

(56) References Cited

U.S. PATENT DOCUMENTS

| | | |
|---|---|---|
| 2002/0015018 A1 | 2/2002 | Shimazu et al. |
| 2002/0018720 A1 | 2/2002 | Carlisle et al. |
| 2002/0029776 A1 | 3/2002 | Blomquist |
| 2002/0031838 A1 | 3/2002 | Meinhart et al. |
| 2002/0032583 A1 | 3/2002 | Joao |
| 2002/0040208 A1 | 4/2002 | Flaherty et al. |
| 2002/0044059 A1 | 4/2002 | Reeder et al. |
| 2002/0045806 A1* | 4/2002 | Baker, Jr. ........... A61B 5/14552 600/323 |
| 2002/0077852 A1 | 6/2002 | Ford et al. |
| 2002/0082728 A1 | 6/2002 | Mueller et al. |
| 2002/0083771 A1 | 7/2002 | Khuri-Yakub et al. |
| 2002/0085952 A1 | 7/2002 | Ellingboe et al. |
| 2002/0087115 A1 | 7/2002 | Hartlaub |
| 2002/0095486 A1 | 7/2002 | Bahl |
| 2002/0099282 A1 | 7/2002 | Knobbe et al. |
| 2002/0099334 A1 | 7/2002 | Hanson et al. |
| 2002/0143580 A1 | 10/2002 | Bristol et al. |
| 2002/0147389 A1 | 10/2002 | Cavallaro et al. |
| 2002/0152239 A1 | 10/2002 | Bautista-Lloyd et al. |
| 2002/0168278 A1 | 11/2002 | Jeon et al. |
| 2002/0173703 A1 | 11/2002 | Lebel et al. |
| 2002/0183693 A1 | 12/2002 | Peterson et al. |
| 2003/0009244 A1 | 1/2003 | Engleson |
| 2003/0013959 A1 | 1/2003 | Grunwald et al. |
| 2003/0018308 A1 | 1/2003 | Tsai |
| 2003/0025602 A1 | 2/2003 | Medema et al. |
| 2003/0028082 A1 | 2/2003 | Thompson |
| 2003/0030001 A1 | 2/2003 | Cooper et al. |
| 2003/0045840 A1 | 3/2003 | Burko |
| 2003/0050621 A1 | 3/2003 | Lebel et al. |
| 2003/0060688 A1 | 3/2003 | Ciarniello et al. |
| 2003/0060765 A1 | 3/2003 | Campbell et al. |
| 2003/0065537 A1 | 4/2003 | Evans |
| 2003/0065589 A1 | 4/2003 | Giacchetti |
| 2003/0073954 A1 | 4/2003 | Moberg et al. |
| 2003/0079746 A1 | 5/2003 | Hickle |
| 2003/0083583 A1 | 5/2003 | Kovtun et al. |
| 2003/0091442 A1 | 5/2003 | Bush et al. |
| 2003/0104982 A1 | 6/2003 | Wittmann et al. |
| 2003/0106553 A1 | 6/2003 | Vanderveen |
| 2003/0125662 A1 | 7/2003 | Bui |
| 2003/0130616 A1 | 7/2003 | Steil |
| 2003/0135087 A1 | 7/2003 | Hickle et al. |
| 2003/0136193 A1 | 7/2003 | Fujimoto |
| 2003/0139701 A1 | 7/2003 | White et al. |
| 2003/0140928 A1 | 7/2003 | Bui et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158508 A1 | 8/2003 | DiGianfilippo |
| 2003/0160683 A1 | 8/2003 | Blomquist |
| 2003/0163789 A1 | 8/2003 | Blomquist |
| 2003/0173408 A1 | 9/2003 | Mosher, Jr. et al. |
| 2003/0187338 A1 | 10/2003 | Say et al. |
| 2003/0194328 A1 | 10/2003 | Bryant et al. |
| 2003/0200116 A1 | 10/2003 | Forrester |
| 2003/0204274 A1 | 10/2003 | Ullestad et al. |
| 2003/0204416 A1 | 10/2003 | Acharya |
| 2003/0212364 A1 | 11/2003 | Mann et al. |
| 2003/0212379 A1 | 11/2003 | Bylund et al. |
| 2003/0217962 A1 | 11/2003 | Childers et al. |
| 2003/0233071 A1 | 12/2003 | Gillespie, Jr. et al. |
| 2004/0030277 A1 | 2/2004 | O'Mahony et al. |
| 2004/0047736 A1 | 3/2004 | Nose et al. |
| 2004/0057226 A1 | 3/2004 | Berthou et al. |
| 2004/0064342 A1 | 4/2004 | Browne et al. |
| 2004/0073125 A1 | 4/2004 | Lovett et al. |
| 2004/0073161 A1 | 4/2004 | Tachibana |
| 2004/0077996 A1 | 4/2004 | Jasperson et al. |
| 2004/0082908 A1 | 4/2004 | Whitehurst |
| 2004/0082918 A1 | 4/2004 | Evans et al. |
| 2004/0104271 A1 | 6/2004 | Martucci et al. |
| 2004/0119753 A1 | 6/2004 | Zencke |
| 2004/0120825 A1 | 6/2004 | Bouton et al. |
| 2004/0145114 A1 | 6/2004 | Ippolito et al. |
| 2004/0128162 A1 | 7/2004 | Schlotterbeck et al. |
| 2004/0133166 A1 | 7/2004 | Moberg et al. |
| 2004/0147034 A1 | 7/2004 | Gore et al. |
| 2004/0149823 A1 | 8/2004 | Aptekar |
| 2004/0152970 A1 | 8/2004 | Hunter et al. |
| 2004/0158193 A1 | 8/2004 | Bui et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172289 A1 | 9/2004 | Kozic et al. |
| 2004/0172302 A1 | 9/2004 | Martucci et al. |
| 2004/0176984 A1 | 9/2004 | White et al. |
| 2004/0181314 A1 | 9/2004 | Zaleski |
| 2004/0193025 A1 | 9/2004 | Steil et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204638 A1 | 10/2004 | Diab et al. |
| 2004/0204673 A1 | 10/2004 | Flaherty et al. |
| 2004/0220517 A1 | 11/2004 | Starkweather et al. |
| 2004/0225252 A1 | 11/2004 | Gillespie et al. |
| 2004/0225409 A1 | 11/2004 | Duncan et al. |
| 2004/0232219 A1 | 11/2004 | Fowler |
| 2004/0247445 A1 | 12/2004 | Nelson et al. |
| 2004/0253123 A1 | 12/2004 | Xie et al. |
| 2004/0254434 A1 | 12/2004 | Goodnow et al. |
| 2004/0254513 A1 | 12/2004 | Shang et al. |
| 2005/0021006 A1 | 1/2005 | Tonnies |
| 2005/0021297 A1 | 1/2005 | Hartlaub |
| 2005/0022274 A1 | 1/2005 | Campbell et al. |
| 2005/0038680 A1 | 2/2005 | McMahon |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0075544 A1 | 4/2005 | Shapiro et al. |
| 2005/0096593 A1 | 5/2005 | Pope et al. |
| 2005/0099624 A1 | 5/2005 | Staehr |
| 2005/0107923 A1 | 5/2005 | Vanderveen |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0143864 A1 | 6/2005 | Blomquist |
| 2005/0145010 A1 | 7/2005 | Vanderveen et al. |
| 2005/0171503 A1 | 8/2005 | Van Den Berghe et al. |
| 2005/0171815 A1 | 8/2005 | Vanderveen |
| 2005/0177045 A1 | 8/2005 | Degertekin et al. |
| 2005/0177096 A1 | 8/2005 | Bollish et al. |
| 2005/0182306 A1 | 8/2005 | Sloan |
| 2005/0182355 A1 | 8/2005 | Bui |
| 2005/0182366 A1 | 8/2005 | Vogt et al. |
| 2005/0187515 A1 | 8/2005 | Varrichio et al. |
| 2005/0192529 A1 | 9/2005 | Butterfield et al. |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0209563 A1 | 9/2005 | Hopping et al. |
| 2005/0209793 A1 | 9/2005 | Yamada |
| 2005/0224083 A1 | 10/2005 | Crass |
| 2005/0235732 A1 | 10/2005 | Rush |
| 2005/0238506 A1 | 10/2005 | Mescher et al. |
| 2005/0240305 A1 | 10/2005 | Bogash et al. |
| 2005/0273059 A1 | 12/2005 | Mernoe et al. |
| 2005/0277890 A1 | 12/2005 | Stewart et al. |
| 2005/0279419 A1 | 12/2005 | Tribble et al. |
| 2006/0002799 A1 | 1/2006 | Schann et al. |
| 2006/0009727 A1 | 1/2006 | O'Mahony et al. |
| 2006/0009734 A1 | 1/2006 | Martin |
| 2006/0042633 A1 | 3/2006 | Bishop et al. |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0064053 A1 | 3/2006 | Bollish et al. |
| 2006/0079768 A1 | 4/2006 | Small et al. |
| 2006/0079831 A1 | 4/2006 | Gilbert |
| 2006/0100746 A1 | 5/2006 | Leibner-Druska |
| 2006/0100907 A1 | 5/2006 | Holland et al. |

(56) References Cited

U.S. PATENT DOCUMENTS

| | | |
|---|---|---|
| 2006/0106649 A1 | 5/2006 | Eggers et al. |
| 2006/0116639 A1 | 6/2006 | Russell |
| 2006/0117856 A1 | 6/2006 | Orr et al. |
| 2006/0117867 A1 | 6/2006 | Froehlich et al. |
| 2006/0122867 A1 | 6/2006 | Eggers et al. |
| 2006/0135939 A1 | 6/2006 | Brown |
| 2006/0135940 A1 | 6/2006 | Joshi |
| 2006/0136271 A1 | 6/2006 | Eggers et al. |
| 2006/0140798 A1 | 6/2006 | Kutsuzawa |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0180916 A1 | 8/2006 | Wyland |
| 2006/0181695 A1 | 8/2006 | Sage, Jr. |
| 2006/0187069 A1 | 8/2006 | Duan |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0224181 A1 | 10/2006 | McEwen et al. |
| 2006/0226088 A1 | 10/2006 | Robinson et al. |
| 2006/0226089 A1 | 10/2006 | Robinson et al. |
| 2006/0226090 A1 | 10/2006 | Robinson et al. |
| 2006/0229557 A1 | 10/2006 | Fathallah et al. |
| 2006/0229918 A1 | 10/2006 | Fotsch et al. |
| 2006/0235353 A1 | 10/2006 | Gelfand et al. |
| 2006/0258985 A1 | 11/2006 | Russell |
| 2006/0260416 A1 | 11/2006 | Sage et al. |
| 2006/0264895 A1 | 11/2006 | Flanders |
| 2006/0265246 A1 | 11/2006 | Hoag |
| 2006/0266128 A1 | 11/2006 | Clark et al. |
| 2006/0270971 A1 | 11/2006 | Gelfand et al. |
| 2006/0271286 A1 | 11/2006 | Rosenberg |
| 2006/0272421 A1 | 12/2006 | Frinak et al. |
| 2006/0275142 A1 | 12/2006 | Bouton et al. |
| 2007/0015972 A1 | 1/2007 | Wang et al. |
| 2007/0036511 A1 | 2/2007 | Lundquist et al. |
| 2007/0060796 A1 | 3/2007 | Kim |
| 2007/0060871 A1 | 3/2007 | Istoc |
| 2007/0060872 A1 | 3/2007 | Hall et al. |
| 2007/0060874 A1 | 3/2007 | Nesbitt et al. |
| 2007/0062250 A1 | 3/2007 | Krulevitch et al. |
| 2007/0065363 A1 | 3/2007 | Dalal et al. |
| 2007/0078314 A1 | 4/2007 | Grounsell |
| 2007/0083152 A1 | 4/2007 | Williams, Jr. et al. |
| 2007/0084288 A1 | 4/2007 | Thomas et al. |
| 2007/0088271 A1 | 4/2007 | Richards |
| 2007/0088333 A1 | 4/2007 | Levin et al. |
| 2007/0093753 A1 | 4/2007 | Krulevitcvh et al. |
| 2007/0100222 A1 | 5/2007 | Mastrototaro et al. |
| 2007/0100665 A1 | 5/2007 | Brown |
| 2007/0112298 A1 | 5/2007 | Mueller et al. |
| 2007/0118405 A1 | 5/2007 | Campbell et al. |
| 2007/0129618 A1 | 6/2007 | Goldberger et al. |
| 2007/0142822 A1 | 6/2007 | Remde |
| 2007/0156452 A1 | 7/2007 | Batch |
| 2007/0179436 A1 | 8/2007 | Braig et al. |
| 2007/0191817 A1 | 8/2007 | Martin |
| 2007/0214003 A1 | 9/2007 | Holland et al. |
| 2007/0215545 A1 | 9/2007 | Bissler et al. |
| 2007/0233035 A1 | 10/2007 | Wehba et al. |
| 2007/0233049 A1 | 10/2007 | Wehba et al. |
| 2007/0240497 A1 | 10/2007 | Robinson et al. |
| 2007/0255250 A1 | 11/2007 | Moberg et al. |
| 2007/0257788 A1 | 11/2007 | Carlson |
| 2007/0267945 A1 | 11/2007 | Sudol |
| 2007/0270747 A1 | 11/2007 | Remde |
| 2007/0274843 A1 | 11/2007 | Vanderveen et al. |
| 2007/0289384 A1 | 12/2007 | Sakai et al. |
| 2007/0299389 A1* | 12/2007 | Halbert ............ A61B 5/0205 604/131 |
| 2008/0009684 A1 | 1/2008 | Corsetti et al. |
| 2008/0028868 A1 | 2/2008 | Konzelmann et al. |
| 2008/0033361 A1 | 2/2008 | Evans et al. |
| 2008/0039777 A1 | 2/2008 | Katz et al. |
| 2008/0048211 A1 | 2/2008 | Khuri-Yakub et al. |
| 2008/0058773 A1 | 3/2008 | John |
| 2008/0060448 A1 | 3/2008 | Wiest et al. |
| 2008/0065420 A1 | 3/2008 | Tirinato et al. |
| 2008/0071210 A1 | 3/2008 | Moubayed et al. |
| 2008/0071496 A1 | 3/2008 | Glascock |
| 2008/0071580 A1 | 3/2008 | Marcus et al. |
| 2008/0091466 A1 | 4/2008 | Butler et al. |
| 2008/0097288 A1 | 4/2008 | Levin et al. |
| 2008/0097289 A1 | 4/2008 | Steil et al. |
| 2008/0097317 A1 | 4/2008 | Alholm et al. |
| 2008/0098798 A1 | 5/2008 | Riley et al. |
| 2008/0119822 A1 | 5/2008 | Knauper |
| 2008/0125701 A1 | 5/2008 | Moberg et al. |
| 2008/0139907 A1 | 6/2008 | Rao et al. |
| 2008/0145249 A1 | 6/2008 | Smisson |
| 2008/0172030 A1 | 7/2008 | Blomquist et al. |
| 2008/0177254 A1 | 7/2008 | Shelton et al. |
| 2008/0184784 A1 | 8/2008 | Dam |
| 2008/0188789 A1 | 8/2008 | Galavotti et al. |
| 2008/0188796 A1 | 8/2008 | Steil et al. |
| 2008/0200870 A1 | 8/2008 | Palmroos et al. |
| 2008/0208484 A1 | 8/2008 | Butterfield et al. |
| 2008/0214919 A1 | 9/2008 | Harmon et al. |
| 2008/0221521 A1 | 9/2008 | Getz et al. |
| 2008/0221522 A1 | 9/2008 | Moberg et al. |
| 2008/0243055 A1 | 10/2008 | Fathallah et al. |
| 2008/0262469 A1 | 10/2008 | Bristol et al. |
| 2008/0269663 A1 | 10/2008 | Arnold et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2009/0001908 A1 | 1/2009 | Shubinsky et al. |
| 2009/0005703 A1 | 1/2009 | Fasciano |
| 2009/0006061 A1 | 1/2009 | Thukral et al. |
| 2009/0006129 A1 | 1/2009 | Thukral |
| 2009/0006133 A1 | 1/2009 | Weinert |
| 2009/0015824 A1 | 1/2009 | Shubinsky et al. |
| 2009/0043171 A1 | 2/2009 | Rule |
| 2009/0053071 A1* | 2/2009 | Wang ............... A61M 5/16831 73/19.01 |
| 2009/0054743 A1 | 2/2009 | Stewart |
| 2009/0054754 A1 | 2/2009 | McMahon et al. |
| 2009/0069743 A1 | 3/2009 | Krishnamoorthy et al. |
| 2009/0077248 A1 | 3/2009 | Castellucci et al. |
| 2009/0082676 A1 | 3/2009 | Bennison |
| 2009/0088731 A1 | 4/2009 | Campbell et al. |
| 2009/0097029 A1 | 4/2009 | Tokhtuev et al. |
| 2009/0112155 A1 | 4/2009 | Zhao |
| 2009/0124963 A1 | 5/2009 | Hogard et al. |
| 2009/0124964 A1 | 5/2009 | Leach et al. |
| 2009/0131861 A1 | 5/2009 | Braig et al. |
| 2009/0135196 A1 | 5/2009 | Holland et al. |
| 2009/0143726 A1 | 6/2009 | Bouton et al. |
| 2009/0144025 A1 | 6/2009 | Bouton et al. |
| 2009/0144026 A1 | 6/2009 | Bouton et al. |
| 2009/0149743 A1 | 6/2009 | Barron et al. |
| 2009/0153058 A1 | 6/2009 | Feng et al. |
| 2009/0156922 A1 | 6/2009 | Goldberger et al. |
| 2009/0156975 A1 | 6/2009 | Robinson et al. |
| 2009/0177146 A1 | 7/2009 | Nesbitt et al. |
| 2009/0177188 A1 | 7/2009 | Steinkogler |
| 2009/0177248 A1 | 7/2009 | Roberts |
| 2009/0177769 A1 | 7/2009 | Roberts |
| 2009/0177992 A1 | 7/2009 | Rubalcaba et al. |
| 2009/0178485 A1 | 7/2009 | Thomas et al. |
| 2009/0183147 A1 | 7/2009 | Davis et al. |
| 2009/0192367 A1 | 7/2009 | Braig et al. |
| 2009/0205426 A1 | 8/2009 | Balschat et al. |
| 2009/0209938 A1 | 8/2009 | Aalto-Setala |
| 2009/0209945 A1 | 8/2009 | Lobl et al. |
| 2009/0212966 A1 | 8/2009 | Panduro |
| 2009/0221890 A1 | 9/2009 | Saffer et al. |
| 2009/0223294 A1 | 9/2009 | Thomas et al. |
| 2009/0227939 A1 | 9/2009 | Memoe et al. |
| 2009/0264720 A1 | 10/2009 | Torjman et al. |

(56) References Cited

U.S. PATENT DOCUMENTS

| | | |
|---|---|---|
| 2009/0270810 A1 | 10/2009 | DeBelser |
| 2009/0270833 A1 | 10/2009 | DeBelser |
| 2010/0022988 A1 | 1/2010 | Wochner |
| 2010/0280430 A1 | 1/2010 | Caleffi et al. |
| 2010/0036310 A1 | 2/2010 | Hillman |
| 2010/0056992 A1 | 3/2010 | Hayter |
| 2010/0069892 A1 | 3/2010 | Steinbach et al. |
| 2010/0077866 A1 | 4/2010 | Graboi et al. |
| 2010/0079760 A1 | 4/2010 | Bernacki |
| 2010/0094251 A1 | 4/2010 | Estes et al. |
| 2010/0106082 A1 | 4/2010 | Zhou |
| 2010/0121170 A1 | 5/2010 | Rule |
| 2010/0121415 A1 | 5/2010 | Skelton et al. |
| 2010/0130933 A1 | 5/2010 | Holland et al. |
| 2010/0131434 A1 | 5/2010 | Magent et al. |
| 2010/0141460 A1 | 6/2010 | Tokhtuev et al. |
| 2010/0147081 A1 | 6/2010 | Thomas et al. |
| 2010/0152554 A1 | 6/2010 | Steine et al. |
| 2010/0160854 A1 | 6/2010 | Gauthier |
| 2010/0168535 A1 | 7/2010 | Robinson et al. |
| 2010/0177375 A1 | 7/2010 | Seyfried |
| 2010/0185142 A1 | 7/2010 | Kamen et al. |
| 2010/0198034 A1 | 8/2010 | Thomas et al. |
| 2010/0198182 A1 | 8/2010 | Lanigan et al. |
| 2010/0198183 A1 | 8/2010 | Lanigan et al. |
| 2010/0211002 A1 | 8/2010 | Davis |
| 2010/0212407 A1 | 8/2010 | Stringham et al. |
| 2010/0212675 A1 | 8/2010 | Walling et al. |
| 2010/0214110 A1 | 8/2010 | Wang et al. |
| 2010/0217154 A1 | 8/2010 | Deshmukh et al. |
| 2010/0217621 A1 | 8/2010 | Schoenberg |
| 2010/0256562 A1* | 10/2010 | Cartledge ............ F04B 43/1253 604/151 |
| 2010/0271218 A1 | 10/2010 | Hoag et al. |
| 2010/0271479 A1 | 10/2010 | Heydlauf |
| 2010/0273738 A1 | 10/2010 | Valcke et al. |
| 2010/0292634 A1 | 11/2010 | Kircher |
| 2010/0295686 A1 | 11/2010 | Sloan et al. |
| 2010/0298765 A1 | 11/2010 | Budiman et al. |
| 2010/0317093 A1 | 12/2010 | Turewicz et al. |
| 2010/0318025 A1 | 12/2010 | John |
| 2011/0000560 A1 | 1/2011 | Miller et al. |
| 2011/0001605 A1 | 1/2011 | Kiani et al. |
| 2011/0004186 A1 | 1/2011 | Butterfield |
| 2011/0009797 A1 | 1/2011 | Kelly et al. |
| 2011/0028885 A1 | 2/2011 | Eggers et al. |
| 2011/0040247 A1 | 2/2011 | Mandro et al. |
| 2011/0046558 A1 | 2/2011 | Gravesen et al. |
| 2011/0062703 A1 | 3/2011 | Lopez et al. |
| 2011/0064612 A1 | 3/2011 | Franzoni et al. |
| 2011/0071464 A1 | 3/2011 | Palerm |
| 2011/0071844 A1 | 3/2011 | Cannon et al. |
| 2011/0072379 A1 | 3/2011 | Gannon |
| 2011/0077480 A1 | 3/2011 | Bloom et al. |
| 2011/0078608 A1 | 3/2011 | Gannon et al. |
| 2011/0099313 A1 | 4/2011 | Bolanowski |
| 2011/0105983 A1 | 5/2011 | Kelly et al. |
| 2011/0106561 A1 | 5/2011 | Eaton, Jr. et al. |
| 2011/0137241 A1 | 6/2011 | DelCastilio et al. |
| 2011/0144595 A1 | 6/2011 | Cheng |
| 2011/0160649 A1 | 6/2011 | Pan |
| 2011/0162647 A1 | 7/2011 | Huby et al. |
| 2011/0172918 A1 | 7/2011 | Tome |
| 2011/0175728 A1 | 7/2011 | Baker, Jr. |
| 2011/0190598 A1 | 8/2011 | Shusterman |
| 2011/0190694 A1 | 8/2011 | Lanier et al. |
| 2011/0264006 A1 | 10/2011 | Ali et al. |
| 2011/0264043 A1 | 10/2011 | Kotnick et al. |
| 2011/0282321 A1 | 11/2011 | Steil et al. |
| 2011/0320049 A1 | 12/2011 | Chossat et al. |
| 2012/0025995 A1 | 2/2012 | Moberg et al. |
| 2012/0035535 A1 | 2/2012 | Johnson et al. |
| 2012/0059234 A1 | 3/2012 | Barrett et al. |
| 2012/0068001 A1 | 3/2012 | Pushkarsky et al. |
| 2012/0095433 A1 | 4/2012 | Hungerford et al. |
| 2012/0123322 A1 | 5/2012 | Scarpaci et al. |
| 2012/0143116 A1 | 6/2012 | Ware et al. |
| 2012/0180790 A1 | 7/2012 | Montgomery |
| 2012/0185267 A1 | 7/2012 | Kamen et al. |
| 2012/0191059 A1 | 7/2012 | Cummings et al. |
| 2012/0194341 A1 | 8/2012 | Peichel et al. |
| 2012/0203177 A1 | 8/2012 | Lanier |
| 2012/0226350 A1 | 9/2012 | Rudser et al. |
| 2012/0245525 A1 | 9/2012 | Pope et al. |
| 2012/0259278 A1 | 10/2012 | Hayes et al. |
| 2013/0006666 A1 | 1/2013 | Schneider |
| 2013/0009551 A1 | 1/2013 | Knapp |
| 2013/0012880 A1 | 1/2013 | Blomquist |
| 2013/0012917 A1 | 1/2013 | Miller et al. |
| 2013/0041342 A1 | 2/2013 | Bernini et al. |
| 2013/0083191 A1 | 4/2013 | Lowery et al. |
| 2013/0085443 A1 | 4/2013 | Lowery et al. |
| 2013/0085689 A1 | 4/2013 | Sur et al. |
| 2013/0110538 A1 | 5/2013 | Butterfield et al. |
| 2013/0150766 A1 | 6/2013 | Olde et al. |
| 2013/0150821 A1 | 6/2013 | Bollish et al. |
| 2013/0158504 A1 | 6/2013 | Ruchti et al. |
| 2013/0201482 A1 | 8/2013 | Munro |
| 2013/0116649 A1 | 9/2013 | Kouyoumjian et al. |
| 2013/0253430 A1 | 9/2013 | Kouyoumjian et al. |
| 2013/0261993 A1* | 10/2013 | Ruchti ..................... G01F 1/74 702/50 |
| 2013/0281965 A1 | 10/2013 | Kamen et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0318158 A1 | 11/2013 | Teng et al. |
| 2013/0345658 A1 | 12/2013 | Browne et al. |
| 2013/0345666 A1 | 12/2013 | Panduro et al. |
| 2014/0039446 A1 | 2/2014 | Day |
| 2014/0224829 A1 | 8/2014 | Capone et al. |
| 2014/0267563 A1 | 9/2014 | Baca et al. |
| 2014/0350513 A1 | 11/2014 | Oruklu et al. |
| 2015/0025453 A1 | 1/2015 | Ledford et al. |
| 2015/0033073 A1 | 1/2015 | Yang et al. |
| 2015/0168958 A1 | 6/2015 | Downie et al. |
| 2015/0246175 A1 | 9/2015 | Shubinsky et al. |
| 2015/0343141 A1 | 12/2015 | Lindo et al. |
| 2016/0042264 A1 | 2/2016 | Borges et al. |
| 2016/0103960 A1 | 4/2016 | Hume et al. |
| 2016/0110088 A1 | 4/2016 | Vik et al. |
| 2016/0151560 A1 | 6/2016 | Toro et al. |
| 2016/0151562 A1 | 6/2016 | Magers et al. |
| 2016/0175517 A1 | 6/2016 | Sileika et al. |
| 2016/0193604 A1 | 7/2016 | McFarland et al. |
| 2016/0256622 A1 | 9/2016 | Day et al. |
| 2017/0043089 A1 | 2/2017 | Handler |
| 2018/0028749 A1 | 2/2018 | Dumas, III et al. |
| 2019/0091401 A1 | 3/2019 | Ruchti et al. |

FOREIGN PATENT DOCUMENTS

| | | |
|---|---|---|
| DE | 31 12 762 | 1/1983 |
| DE | 34 35 647 | 7/1985 |
| DE | 35 30 747 | 3/1987 |
| DE | 37 20 664 | 1/1989 |
| DE | 38 27 444 | 2/1990 |
| DE | 197 34 002 | 9/1998 |
| DE | 199 01 078 | 2/2000 |
| DE | 198 40 965 | 3/2000 |
| DE | 198 44 252 | 3/2000 |
| DE | 199 32 147 | 1/2001 |
| DE | 102 49 238 | 5/2004 |
| DE | 103 52 456 | 7/2005 |
| EP | 0 282 323 | 9/1988 |
| EP | 0 291 727 | 11/1988 |
| EP | 0 319 272 | 6/1989 |
| EP | 0 319 275 | 6/1989 |
| EP | 0 335 385 | 10/1989 |
| EP | 0 337 092 | 10/1989 |
| EP | 0 341 582 | 11/1989 |
| EP | 0 370 162 | 5/1990 |
| EP | 0 387 724 | 9/1990 |
| EP | 0 429 866 | 6/1991 |

(56) References Cited

FOREIGN PATENT DOCUMENTS

| | | |
|---|---|---|
| EP | 0 441 323 | 8/1991 |
| EP | 0 453 211 | 10/1991 |
| EP | 0 462 405 | 12/1991 |
| EP | 0 501 234 | 9/1992 |
| EP | 0 516 130 | 12/1992 |
| EP | 0 519 765 | 12/1992 |
| EP | 0 643 301 | 3/1995 |
| EP | 0 683 465 | 11/1995 |
| EP | 0 431 310 | 1/1996 |
| EP | 0 589 439 | 8/1998 |
| EP | 0 880 936 | 12/1998 |
| EP | 0 954 090 | 11/1999 |
| EP | 0 960 627 | 12/1999 |
| EP | 1 174 817 | 1/2002 |
| EP | 1 177 802 | 2/2002 |
| EP | 1 197 178 | 4/2002 |
| EP | 1 500 025 | 4/2003 |
| EP | 1 813 188 | 8/2007 |
| EP | 2 062 527 | 5/2009 |
| EP | 2 228 004 | 9/2010 |
| EP | 2 243 506 | 10/2010 |
| EP | 2 381 260 | 10/2011 |
| ES | 254513 | 10/1981 |
| FR | 2 717 919 | 9/1995 |
| GB | 2 121 971 | 1/1984 |
| GB | 2 303 706 | 2/1997 |
| GB | 2 312 022 | 10/1997 |
| GB | 2 312 046 | 10/1997 |
| JP | 01-301118 | 12/1989 |
| JP | 01-308568 | 12/1989 |
| JP | 04-231966 | 8/1992 |
| JP | 07-502678 | 3/1995 |
| JP | 07-289638 | 11/1995 |
| JP | 11-128344 | 5/1999 |
| JP | 2000-111374 | 4/2000 |
| JP | 2000-510575 | 8/2000 |
| JP | 2000-515716 | 11/2000 |
| JP | 2001-356034 | 12/2001 |
| JP | 2002-506514 | 2/2002 |
| JP | 2002-131105 | 5/2002 |
| JP | 2003-038642 | 2/2003 |
| JP | 2003-050144 | 2/2003 |
| JP | 2005-021463 | 1/2005 |
| JP | 2005-524081 | 3/2005 |
| JP | 2006-517423 | 7/2006 |
| JP | 2007-071695 | 3/2007 |
| JP | 2007-520270 | 7/2007 |
| JP | 2008-249400 | 10/2008 |
| JP | 4322661 | 6/2009 |
| JP | 2010-063767 | 3/2010 |
| WO | WO 84/000690 | 3/1984 |
| WO | WO 84/000894 | 3/1984 |
| WO | WO 90/007942 | 7/1990 |
| WO | WO 91/000113 | 1/1991 |
| WO | WO 91/016087 | 10/1991 |
| WO | WO 91/016416 | 10/1991 |
| WO | WO 93/004284 | 3/1993 |
| WO | WO 95/016200 | 6/1995 |
| WO | WO 95/031233 | 11/1995 |
| WO | WO 96/008755 | 3/1996 |
| WO | WO 96/025186 | 8/1996 |
| WO | WO 96/028209 | 9/1996 |
| WO | WO 96/041156 | 12/1996 |
| WO | WO 97/010013 | 3/1997 |
| WO | WO 97/030333 | 8/1997 |
| WO | WO 98/004304 | 2/1998 |
| WO | WO 98/012670 | 3/1998 |
| WO | WO 98/014234 | 4/1998 |
| WO | WO 98/019263 | 5/1998 |
| WO | WO 98/044320 | 10/1998 |
| WO | WO 98/056441 | 12/1998 |
| WO | WO 99/015216 | 4/1999 |
| WO | WO 99/051003 | 10/1999 |
| WO | WO 99/052575 | 10/1999 |
| WO | WO 00/013580 | 3/2000 |
| WO | WO 00/013726 | 3/2000 |
| WO | WO 00/041621 | 7/2000 |
| WO | WO 01/014974 | 3/2001 |
| WO | WO 01/033484 | 5/2001 |
| WO | WO 01/033710 | 5/2001 |
| WO | WO 02/005702 | 1/2002 |
| WO | WO 02/009795 | 2/2002 |
| WO | WO 02/027276 | 4/2002 |
| WO | WO 02/066101 | 8/2002 |
| WO | WO 02/087664 | 11/2002 |
| WO | WO 03/006091 | 1/2003 |
| WO | WO 03/053498 | 7/2003 |
| WO | WO 03/093780 | 11/2003 |
| WO | WO 2004/035115 | 4/2004 |
| WO | WO 2004/060455 | 7/2004 |
| WO | WO 2004/070556 | 8/2004 |
| WO | WO 2004/112579 | 12/2004 |
| WO | WO 2005/018716 | 3/2005 |
| WO | WO 2005/030489 | 4/2005 |
| WO | WO 2005/036447 | 4/2005 |
| WO | WO 2005/050526 | 6/2005 |
| WO | WO 2005/057175 | 6/2005 |
| WO | WO 2005/065146 | 7/2005 |
| WO | WO 2005/065749 | 7/2005 |
| WO | WO 2005/082450 | 9/2005 |
| WO | WO 2005/118015 | 12/2005 |
| WO | WO 2006/016122 | 2/2006 |
| WO | WO 2006/022906 | 3/2006 |
| WO | WO 2007/000426 | 1/2007 |
| WO | WO 2007/033025 | 3/2007 |
| WO | WO 2007/035567 | 3/2007 |
| WO | WO 2007/087443 | 8/2007 |
| WO | WO 2008/004560 | 1/2008 |
| WO | WO 2008/019016 | 2/2008 |
| WO | WO 2008/053193 | 5/2008 |
| WO | WO 2008/059492 | 5/2008 |
| WO | WO 2008/063429 | 5/2008 |
| WO | WO 2008/067245 | 6/2008 |
| WO | WO 2008/088490 | 7/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/026420 | 2/2009 |
| WO | WO 2009/039203 | 3/2009 |
| WO | WO 2009/039214 | 3/2009 |
| WO | WO 2009/049252 | 4/2009 |
| WO | WO 2009/127683 | 10/2009 |
| WO | WO 2010/017279 | 2/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/135646 | 11/2010 |
| WO | WO 2010/135654 | 11/2010 |
| WO | WO 2010/135670 | 11/2010 |
| WO | WO 2010/135686 | 11/2010 |
| WO | WO 2010/148205 | 12/2010 |
| WO | WO 2011/017778 | 2/2011 |
| WO | WO 2011/080188 | 7/2011 |
| WO | WO 2011/109774 | 9/2011 |
| WO | WO 2012/042763 | 4/2012 |
| WO | WO 2012/082599 | 6/2012 |
| WO | WO 2013/028524 | 2/2013 |
| WO | WO 2013/096769 | 6/2013 |
| WO | WO 2015/134478 | 9/2015 |
| WO | WO 2017/051271 | 3/2017 |
| WO | WO 2017/197024 | 11/2017 |

OTHER PUBLICATIONS

ALARIS® Medical Systems, "Signature Edition® GOLD—Single & Dual Channel Infusion System", San Diego, CA, USA, date unknown, but believed to be at least as early as Nov. 29, 2008, pp. 70-74, 2-88 & 2-91.

(56) References Cited

OTHER PUBLICATIONS

Allegro, "3955—Full-Bridge PWM Microstepping Motor Drive", Datasheet, 1997, pp. 16.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
Baxter, "Baxter Receives 510(k) Clearance for Next-Generation SIGMA Spectrum Infusion Pump with Master Drug Library" Press Release, May 8, 2014, pp. 2. http://web.archive.org/web/20160403140025/http://www.baxter.com/news-media/newsroom/press-release/2014/05_08_14_sigma.page.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Binder et al., "Insulin Infusion with Parenteral Nutrition in Extremely Low Birth Weight Infants with Hyperglycemia", Journal of Pediatrics, Feb. 1989, vol. 114, No. 2, pp. 273-280.
Bode et al., "Intravenous Insulin Infusion Therapy: Indications, Methods, and Transition to Subcutaneous Insulin Therapy", Endocrine Practice, Mar./Apr. 2004, vol. 10, Supplement 2, pp. 71-80.
Duhrdorf et al., "Capacitive Micromachined Ultrasonic Transducers and their Application", Proceedings of the IEEE Ultrasonics Symposium, Feb. 2001, vol. 2, pp. 933-940.
Cannon, MD et al., "Automated Heparin-Delivery System to Control Activated Partial Thromboplastin Time", Circulation, Feb. 16, 1999, vol. 99, pp. 751-756.
"CareAware® Infusion Management", Cerner Store, as printed May 12, 2011, pp. 3, https://store.cerner.com/items/7.
Chen et al., "Enabling Location-Based Services on Wireless LANs", The 11th IEEE International Conference on Networks, ICON 2003, Sep. 28-Oct. 1, 2003, pp. 567-572.
Cheung et al., "Hyperglycemia is Associated with Adverse Outcomes in Patients Receiving Total Parenteral Nutrition", Diabetes Care, Oct. 2005, vol. 28, No. 10, pp. 2367-2371.
Coley et al., "Performance of Three Portable Infusion-Pump Devices Set to Deliver 2 mL/hr", American Journal of Health-System Pharmacy, Jun. 1, 1997, vol. 54, No. 11, pp. 1277-1280.
"Continually vs Continuously", https://web.archive.org/web/20090813092423/http://www.diffen.com/difference/Continually_vs_Continuously, as accessed Aug. 13, 2009 in 4 pages.
"CritiCore® Monitor: Critical Fluid Output and Core Bladder Temperature Monitor", BARD Urological Catheter Systems, Advertisement, 2005, pp. 2.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
"Differential Pressure Transmitter, Series PD-39 X", SensorsOne Ltd., Advertisement, Dec. 2005, pp. 2.
Dunster et al., "Flow Continuity of Infusion Systems at Low Flow Rates", Anaesthesia and Intensive Care, Oct. 1995, vol. 23, No. 5, pp. 5.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
"Froth", http://www.merriam-webster.com/dictionary/froth, as accessed May 13, 2015 in 1 page.
Goldberg et al., "Clinical Results of an Updated Insulin Infusion Protocol in Critically Ill Patients", Diabetes Spectrum, 2005, vol. 18, No. 3, pp. 188-191.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hospira, "Plum A+™ Infusion System" as archived Dec. 1, 2012, pp. 2. www.hospira.com/products_and_services/infusion_pumps/plum/index.
Hospira, "Plum XL™ Series Infusion System" Technical Service Manual, Feb. 2005, Lake Forest, Illinois, USA, pp. i-vii, 5-14, 8-3.
Ilfeld et al., "Delivery Rate Accuracy of Portable, Bolus-Capable Infusion Pumps Used for Patient-Controlled Continuous Regional Analgesia", Regional Anesthesia and Pain Medicine, Jan.-Feb. 2003, vol. 28, No. 1, pp. 17-23.
Ilfeld et al., "Portable Infusion Pumps Used for Continuous Regional Analgesia: Delivery Rate Accuracy and Consistency", Regional Anesthesia and Pain Medicine, Sep.-Oct. 2003, vol. 28, No. 5, pp. 424-432.
JMS Co., Ltd., "Infusion Pump: OT-701", Tokyo, Japan, 2002, pp. 4.
Kutcher et al., "The Effect of Lighting Conditions on Caries Interpretation with a Laptop Computer in a Clinical Setting", Elsevier, Oct. 2006, vol. 102, No. 4, pp. 537-543.
Lamsdale et al., "A Usability Evaluation of an Infusion Pump by Nurses Using a Patient Simulator", Proceedings of the Human Factors and Ergonomics Society 49th Annual Meeting, Sep. 2005, pp. 1024-1028.
Logan et al., "Fabricating Capacitive Micromachined Ultrasonic Transducers with a Novel Silicon-Nitride-Based Wafer Bonding Process", IEEE Transactions on Ultrasonics, Ferroelectrics, and Frequency Control, May 2009, vol. 56, No. 5, pp. 1074-1084.
Magaji et al., "Inpatient Management of Hyperglycemia and Diabetes", Clinical Diabetes, 2011, vol. 29, No. 1, pp. 3-9.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Maynard et al., "Subcutaneous Insulin Order Sets and Protocols: Effective Design and Implementation Strategies", Journal of Hospital Medicine, Sep./Oct. 2008, vol. 3, Issue 5, Supplement 5, pp. S29-S41.
Merry et al., "A New, Safety-Oriented, Integrated Drug Administration and Automated Anesthesia Record System", Anesthesia & Analgesia, Aug. 2001, vol. 93, No. 2 pp. 385-390.
Microchip Technology Inc., "MTA11200B; TrueGauge™ Intelligent Battery Management I.C.", https://www.elektronik.ropla.eu/pdf/stock/mcp/mta11200b.pdf, 1995, pp. 44.
Moghissi, Etie, MD, FACP, FACE, "Hyperglycemia in Hospitalized Patients", A Supplement to ACP Hospitalist, Jun. 15, 2008, pp. 32.
Nuckols et al., "Programmable Infusion Pumps in ICUs: An Analysis of Corresponding Adverse Drug Events", Journal of General Internal Medicine, 2007, vol. 23, Supp. 1, pp. 41-45.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
SGS-Thomson Microelectronics, "L6219—Stepper Motor Drive", Datasheet, Dec. 1996, pp. 10.
SGS-Thomson Microelectronics, "PBL3717A—Stepper Motor Drive", Datasheet, Apr. 1993, pp. 11.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Smith, Joe, "Infusion Pump Informatics", CatalyzeCare: Transforming Healthcare, as printed May 12, 2011, pp. 2.

(56) References Cited

OTHER PUBLICATIONS

Tang et al., "Linear Dimensionality Reduction Using Relevance Weighted LDA", Pattern Recognition, 2005, vol. 38. pp. 485-493, http://staff.ustc.edu.cn/~ketang/papers/Tang/SuganYaoQin_PR04.pdf.

Thomas et al., "Implementation of a Tight Glycaemic Control Protocol Using a Web-Based Insulin Dose Calculator", Anaesthesia, 2005, vol. 60, pp. 1093-1100.

Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.

Van Den Berghe, M.D., Ph.D., et al., "Intensive Insulin Therapy in the Medical ICU", The New England Journal of Medicine, Feb. 2, 2006, vol. 354, No. 5, pp. 449-461.

Westbrook et al., "Errors in the Administration of Intravenous Medications in Hospital and the Role of Correct Procedures and Nurse Experience", BMJ Quality & Safety, 2011, vol. 20, pp. 1027-1034.

Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.

International Search Report and Written Opinion received in PCT Application No. PCT/US2014/040022, dated Oct. 23, 2014 in 8 pages.

International Preliminary Report on Patentability and Written Opinion received in PCT Application No. PCT/US2014/040022, dated Dec. 10, 2015 in 7 pages.

Kim, M.D., et al., "Hyperglycemia Control of the Nil Per Os Patient in the Intensive Care Unit: Introduction of a Simple Subcutaneous Insulin Algorithm", Nov. 2012, Journal of Diabetes Science and Technology, vol. 6, No. 6, pp. 1413-1419.

\* cited by examiner

INFUSION SYSTEM WHICH UTILIZES ONE OR MORE SENSORS AND ADDITIONAL INFORMATION TO MAKE AN AIR DETERMINATION REGARDING THE INFUSION SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE DISCLOSURE

This disclosure relates to detection systems and methods for detecting an end of bag (EOB) event or air in an infusion system.

BACKGROUND

Infusion pumps often do not have an end-of-infusion detection system. Instead, an air-in-line alarm is provided in the event that the medication container becomes prematurely empty and air is present in the infusion line. However, many customers utilize the air-in-line alarm as a mechanism to detect when the medication container is empty rather than titrate an unknown quantity of drug containing fluid after the set volume to be infused (VTBI) is complete. Caregivers often struggle with delivering 100% of the prescribed medication to a patient because the diluent typically varies in volume up to approximately 10%.

Existing strategies for detecting air often involve the use of ultrasonic sensors that are physically located on opposite sides of a tubing segment. When fluid is present in the tube, propagation of the acoustic signal is efficient and produces a large electrical signal via the receiver circuit. On the other hand, the presence of air in the tube causes an acoustical open circuit which substantially attenuates the detected signal. In current practice, detection of air in the tubing segment is often performed on the basis of a simple (static) air-fluid boundary or threshold that is applied to the air sensor voltage signal. When the air sensor signal moves beyond the pre-defined air/fluid threshold, an alarm condition occurs and the IV infusion is paused.

However, when the medication container is emptied (i.e., EOB reached) during an infusion program, a transition occurs from delivery of fluid to air. A film of liquid trails the liquid front as it moves in the tube. This film can break up leading to a stationary fluid droplet formation between the ultrasound transducers that is large enough to create an acoustic short circuit, yet small enough to allow air to pass. This acoustic short circuit can produce an absolute sensor signal similar to that of a fluid, which will cause false indication of fluid in the line and fail to detect the EOB and air in the line.

Currently, there exist methods/algorithms that utilize plunger force sensor readings to detect the presence of air in a plunger chamber. Several pumps made by Hospira, Inc. involve the use of a cassette with a chamber that is compressed by an actuated plunger to pump fluid at a controlled rate from the drug container to the patient. The measured force during a pumping cycle is directly related to the type of fluid in the chamber. For instance, fluids are relatively incompressible and generate a higher and different force profile than air.

However, using the existing force algorithms for detecting EOB often leads to a large number of false positives since the medication type (e.g., frothy fluids), proximal/distal pressure change and other factors can cause variability in force sensor observations.

A system and method is needed to overcome one or more issues of one or more of the current infusion systems and methods in order to detect an EOB event or to determine whether air is in the infusion system.

SUMMARY

In one embodiment, an infusion system for being operatively connected to a fluid delivery line and to an infusion container containing an infusion fluid is disclosed. The infusion system includes a pump, at least one sensor, at least one processor, and a memory. The at least one sensor is connected to the pump or the fluid delivery line. The at least one sensor is configured to indicate whether air is in the fluid delivery line. The at least one processor is in electronic communication with the pump and the at least one sensor. The memory is in electronic communication with the at least one processor. The memory includes programming code for execution by the at least one processor. The programming code is configured to determine an air determination related to the air in the fluid delivery line. This determination is based on measurements taken by the at least one sensor. This determination is also based on: (1) medication information regarding the infusion fluid or infusion information regarding the infusion of the infusion fluid; or (2) multichannel filtering of the measurements from the at least one sensor or non-linear mapping of the measurements from the at least one sensor; and statistical process control charts applied to the multi-channel filtered measurements or applied to the non-linear mapped measurements.

In another embodiment, a method for infusing an infusion fluid is disclosed. In one step, infusion fluid is pumped through a fluid delivery line of an infusion system. In another step, measurements are taken with at least one sensor connected to the infusion system. In an additional step, an air determination is determined with at least one processor. The air determination is related to air in the fluid delivery line. The air determination is based on the measurements taken by the at least one sensor. The air determination is further based on: (1) medication information regarding the infusion fluid or infusion information regarding the infusion of the infusion fluid; or (2) multi-channel filtering of the measurements from the at least one sensor or nonlinear mapping of the measurements from the at least one sensor; and statistical process control charts applied to the multi-channel filtered measurements or applied to the non-linear mapped measurements.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
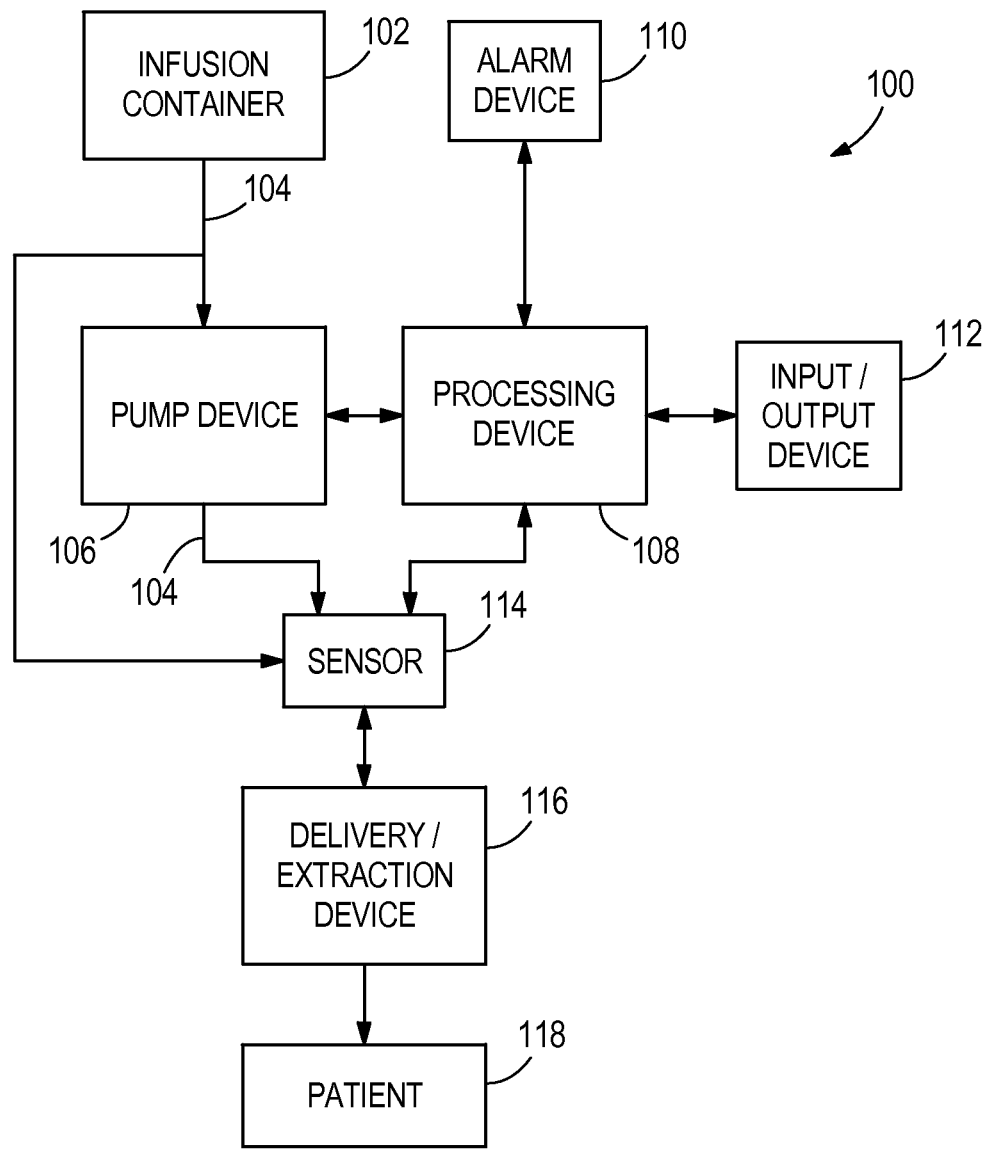
FIG. 1 illustrates a block diagram of an infusion system under one embodiment of the disclosure.

The instant disclosure discloses in part a system and method for detecting the end-of-infusion (i.e., depletion of fluid in the medication infusion reservoir such as an IV bag or infusion container) for IV medication infusion pumps (e.g., Symbig™, Gemstar™, or Plum™). Current air-in-line detection systems often are not robust and reliable enough to be used routinely as end-of-infusion detectors. Applicant has discovered that the combination of multiple sensors as well as a priori knowledge about the infusion and medication significantly improves the robustness of detecting an empty medication container via the presence of air in the line.

The disclosure integrates multiple sensors, drug information and VTBI (volume of the drug in the container to be infused) into the decision making process in order to improve the robustness, and the true negative and false positive performance of end-of-bag (EOB) detection systems (e.g., qualifies a decision only within VTBI±10%). Disclosed are methods of qualifying the signals from plunger force sensor and combining the VTBI to improve the reliability of end-of-bag detection systems. The disclosed system(s) are designed to function as a redundant safety layer in case of air-sensor based AIL (air-in-line) detection systems fail to detect the EOB. In an alternate embodiment, the disclosure can be used to detect and quantify the presence of air in the pumping chamber using multi-channel filtering, wavelet transforms, neural networks and SPC (Statistical Process Control) charts.

The following is a summary of some distinguishing elements of the disclosure. In one embodiment of the disclosure, an event detection and qualifier algorithm is disclosed that determines EOB during delivery on the basis of sensor observations (such as plunger force sensor observations, air sensor readings, pressure sensor readings) and on other information (such as infusion information or medication information). In another embodiment of the disclosure, an event detection algorithm is disclosed that determines confidence levels for presence of air in the infusion system. In an additional embodiment of the disclosure, an event detection algorithm is disclosed that determines the presence of air in the infusion system on the basis of multi-channel filtering of the force sensor observations and SPC (Statistical Process Control) charts. In still another embodiment of the disclosure, an event detection algorithm is disclosed that determines the presence of air in the infusion system on the basis of wavelet transform of the force sensor observations and SPC (Statistical Process Control) charts. In yet another embodiment of the disclosure, an event detection algorithm is disclosed that determines the presence of air in the infusion system on the basis of non-linear mapping (e.g., neural networks) of sensor observations. In still another embodiment of the disclosure, quantitative information is provided regarding the volume of air in a pumping chamber at any particular time.

One problem addressed in the disclosure is to develop a robust end-of infusion detection system that will indicate to clinicians when the infusion container is empty. Another problem addressed in this disclosure is to rely on additional information such as infusion information or medication information to function as a redundant safety layer in case sensor based air detection systems fail to detect the EOB. Systems and methods are discloses for qualifying the signals from one or more sensors and combining the additional information (such as infusion information or medication information) to improve the reliability of end-of bag detection systems.

Another problem addressed in this disclosure is to develop a novel algorithm (e.g., multi-channel, non-linear mapping such as wavelet transform and neural networks, SPC charts) for detecting air in the infusion system using sensor observations. In current practice, force algorithms are typically based on singe-channel and linear filters.

The disclosure satisfies a customer user need for an accurate and reliable system for detecting the end of an infusion. This is frequently observed at cancer treatment facilities in which nurses spend valuable time titrating 1-100 mL after the programmed VTBI is complete. The reason for the additional titration is that infusion bags are typically overfilled by up to 10%.

One embodiment of the disclosure improves the EOB detection capability of existing infusion pump systems that rely on sensors to make a real-time assessment. In doing so, the disclosed method does not require additional hardware modifications but instead leverages the acquired multi-sensor signals. Additionally, the disclosure does not necessarily replace existing software modules for air detection but adds an additional safety layer.

Another embodiment of the disclosure provides a method for improving the robustness of EOB detection systems by reducing the likelihood of a false positive air detection and by reducing the likelihood of a missed alarm. This reduces the chances of an interruption of therapy due to a false alarm and also reduces the chances that the system will miss a true alarm. Still another embodiment of the disclosure provides a means to improve the sensitivity and specificity of air-in-line detection.

FIG. 1 illustrates a block diagram of an infusion system 100 under one embodiment of the disclosure. The infusion system 100 comprises: an infusion container 102; a fluid delivery line 104; a pump device 106; a processing device 108; an alarm device 110 that generates an audio, visual, or other sensory signal or the like to a user; an input/output device 112; at least one sensor 114; and a delivery/extraction device 116. The infusion system 100 may comprise an infusion system such as the Plum™, Gemstar™ Symbig™, or other type of infusion system.

The infusion container 102 comprises a container for delivering an infusion fluid such as IV fluid or a drug to a patient 118. The fluid delivery line 104 comprises one or more tubes, connected between the infusion container 102, the pump device 106, at least one sensor 114, and the delivery/extraction device 116, for transporting infusion fluid from the infusion container 102, through the pump device 106, through the at least one sensor 114, through the delivery/extraction device 116 to the patient 118. The fluid delivery line 104 may also be used to transport blood, extracted from the patient 118 using the delivery/extraction device 116, through the at least one sensor 114 as a result of a pumping action of the pump device 106. The pump device 106 comprises a pump for pumping infusion fluid from the infusion container 102 or for pumping blood from the patient 118. The pump device 106 may comprise a plunger based pump, a peristaltic pump, or another type of pump.

The processing device 108 is in electronic communication with the pump device 106 and the at least one sensor 114. The processing device 108 comprises at least one processor for processing information received from the at least one sensor 114 and for executing one or more algorithms to determine an air determination related to the air in the fluid delivery line based on measurements taken by the at least one sensor 114 and on: (1) medication information regarding the infusion fluid or infusion information regarding the infusion of the infusion fluid; or (2) multi-channel filtering of the measurements from the at least one sensor 114 or non-linear mapping of the measurements from the at least one sensor 114; and statistical process control charts applied to the multi-channel filtered measurements or applied to the non-linear mapped measurements.

The air determination made by the processing device 108 using the programming code may be based on: mean values; variances; derivatives; principal component scores; frequencies; wavelet coefficients; shapes; distance metrics; threshold crossings; coherence between signals; correlation between signals; phase shifts; peak values; minimum values; pattern recognition; Bayesian networks; support vector machines; linear discriminant analysis; decision trees; K-nearest neighbor; template matching; thresholds/limits; normalization; digitization; factor decomposition; simple aggregation; or one or more other factors or information.

The medication information regarding the infusion fluid delivered from the infusion container 102 may comprise a formulation of the infusion fluid, a rate of the infusion fluid, a duration of the infusion fluid, a viscosity of the infusion fluid, a therapy of the infusion fluid, or a property of the infusion fluid. The infusion information regarding the infusion fluid delivered from the infusion container 102 may comprise a volume of the infusion fluid in the infusion container, a volume to be infused (VTBI), or another parameter regarding the infusion of the infusion fluid. The processing device 108 includes or is in electronic communication with a computer readable memory, containing programming code containing the one or more algorithms for execution by the processor, and a clock.

The air determination made by the processing device 108 using the programming code may comprise determining an end-of-container event when the infusion container 102 has been emptied of the infusion fluid, determining a confidence level (which may comprise a probability that the infusion system 100 contains the air) that the line 104 of the infusion system 100 contains the air, or determining whether the air is in the infusion system 100. The processing device 108 may determine the end-of-container event or the confidence level based on the medication information regarding the infusion fluid, based on the infusion information regarding the infusion of the infusion fluid, or based on a combination thereof. The processing device 108 may determine whether the air is in the infusion system 100 or to predict or forecast future measurements of the at least one sensor 114 based on the multi-channel filtering of the measurements from the at least one sensor 114. The processing device 108 may determine whether the air is in the infusion system 100 based on the non-linear mapping of the measurements from the at least one sensor 114. In other embodiments, the processing device 108 may make the air determination using another type of information based on any system, method, or other information disclosed herein, or based on another system, method, or information not disclosed herein.

The alarm device 110 comprises an alarm, triggered by the processing device 108, for notifying the clinician (also referred to as 'user' herein) of: (1) when there is an end-of-container event when the infusion container 102 has been emptied of the infusion fluid; or (2) when the infusion system 100 contains air. The alarm device 110 may be configured to stop the pump device 106 prior to a significant amount of air being delivered through the fluid delivery line 104 and the delivery/extraction device 116 to the patient 118.

The input/output device 112 comprises a device which allows a clinician to input or receive information. The input/output device 112 allows a clinician to input information such as: medication information regarding the infusion fluid being delivered from the infusion container 102; infusion information regarding the infusion of the infusion fluid being delivered from the infusion container 102; the selection of settings for the processing device 108 to apply in using the programming code containing the algorithm(s); or other information that is pertinent to the infusion. The input/output device 112 may allow a clinician to select and/or confirm a user-inputted medication infusion program to be applied by the processing device 108. The input/output device 112 may further output information to the clinician. In other embodiments, any of the information inputted into the input/output device 112 may be pre-installed into the programming code or the processing device 108. In another embodiment, the information may be remotely programmed into the processing device 108 from a remote computer or the input/output device 112 may be a remote and/or portable computer.

The one or more sensors 114 may comprise any number, combination, or configuration of one or more pressure sensors, one or more force sensors, one or more air sensors, one or more rate sensors, one or more temperature sensors, or one or more other type of sensors located and connected to anywhere within the infusion system including the fluid delivery line 104, the pump device 106, or elsewhere for determining whether air is disposed in the infusion system 100. As illustrated the sensor 114 can be located upstream (proximal), downstream (distal) or at the pump device 106.

If a pressure sensor is used, it may comprise one or more proximal or distal pressure sensors for detecting the amount of pressure in the fluid delivery line 104 proximal, distal or at the plunger or pumping member of the pump device 106. It can also comprise one or more chamber pressure sensors for detecting the amount of pressure in the chamber of the pumping device 106. The amount of pressure detected by the one or more pressure sensors is indicative of whether air, fluid, or some combination thereof is present in the fluid delivery line 104. For instance, U.S. Pat. No. 8,403,908 to Jacobson et al., which is commonly owned and hereby incorporated by reference, discloses the use of pressure sensors to determine whether air, fluid, or some combination thereof is present in the fluid delivery line 104.

If a force sensor is used, it may comprise one or more force sensors (such as a plunger force sensor or other type of sensor) for detecting the amount of force on the plunger of the pump device 106. The amount of force detected by the one or more force sensors is indicative of whether air, fluid, or some combination thereof is present in the fluid delivery line 104. For instance, U.S. Ser. No. 13/851,207 filed 27 Mar. 2013, which is commonly owned and hereby incorporated by reference, discloses the use of force sensors to determine whether air, fluid, or some combination thereof is present in the fluid delivery line 104.

If an air sensor is used, it may comprise one or more air sensors (such as a proximal air sensor, a distal air sensor, or another air sensor) for detecting whether air, fluid, or a combination thereof is present in the fluid delivery line 104. The strength of the signal that propagates from the one or more air sensors through the fluid delivery line 104 is indicative of whether air, fluid, or some combination thereof is present in the fluid delivery line 104. For instance, U.S. Pat. No. 7,981,082 to Wang et al., which is commonly owned and hereby incorporated by reference, discloses the use of air sensors to determine whether air, fluid, or some combination thereof is present in the fluid delivery line 104.

If a rate sensor is used, it may comprise one or more rate sensors for detecting a rate of the infusion fluid traveling through the fluid delivery line 104 to assist in making the air determination. If a temperature sensor is used, it may comprise one or more temperature sensors for detecting a temperature of the infusion fluid traveling through the fluid delivery line 104 to assist in making the air determination. In other embodiments, any number, type, combination, or configuration of sensors 114 may be used to determine whether air, fluid, or some combination thereof is present in the fluid delivery line 104. For instance, in one embodiment, a plurality of different types of sensors 114 may be used.

The delivery/extraction device 116 comprises a patient vascular access point device for delivering infusion fluid from the infusion container 102 to the patient 118, or for delivering blood to or extracting blood from the patient 118. The delivery/extraction device 116 may comprise a needle, a catheter, a cannula, or another type of delivery/extraction device. In other embodiments, the infusion system 100 of FIG. 1 may be altered to vary the components, to take away one or more components, or to add one or more components.

Figure 2:
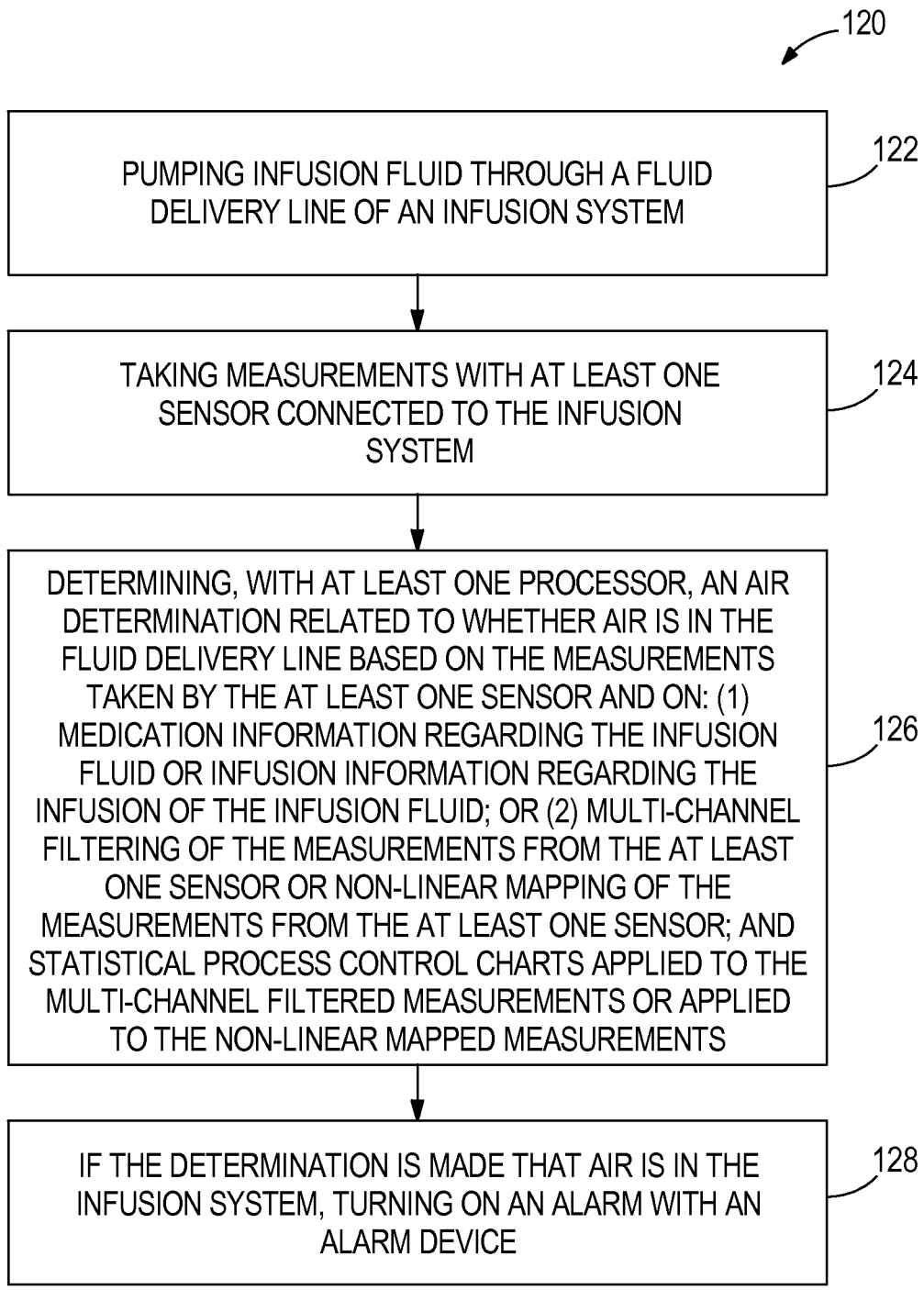
FIG. 2 illustrates a flowchart of one embodiment of a method for infusing an infusion fluid.

FIG. 2 illustrates a flowchart of one embodiment of a method 120 for infusing an infusion fluid. The method 120 may utilize the infusion system 100 of FIG. 1. In other embodiments, the method 120 may utilize varying systems. In step 122, the infusion fluid is pumped through a fluid delivery line of an infusion system. In step 124, measurements are taken with at least one sensor connected to the infusion system. In step 126, at least one processor determines an air determination related to whether air is in the fluid delivery line based on the measurements taken by the at least one sensor and on: (1) medication information regarding the infusion fluid or infusion information regarding the infusion of the infusion fluid; or (2) multi-channel filtering of the measurements from the at least one sensor or non-linear mapping of the measurements from the at least one sensor; and statistical process control charts applied to the multi-channel filtered measurements or applied to the non-linear mapped measurements.

The air determination may comprise determining an end of container event when the infusion container has been emptied of the infusion fluid, determining a confidence level (which may comprise a probability that the infusion system contains the air) that the infusion system contains the air, or determining whether the air is in the infusion system. The medication information regarding the infusion fluid delivered from the infusion container may comprise a formulation of the infusion fluid, a rate of the infusion fluid, a duration of the infusion fluid, a viscosity of the infusion fluid, a therapy of the infusion fluid, or a property of the infusion fluid. The infusion information regarding the infusion fluid delivered from the infusion container may comprise a volume of the infusion fluid in the infusion container, a volume to be infused (VTBI), or another parameter regarding the infusion of the infusion fluid.

In step 128, an alarm device generates or turns on an alarm if step 126 determines that air is in the infusion system. Step 128 may further comprise the alarm shutting down the infusion system. In other embodiments, the method 120 may be altered to vary the order or substance of any of the steps, to delete one or more steps, or to add one or more steps.

Figure 3:
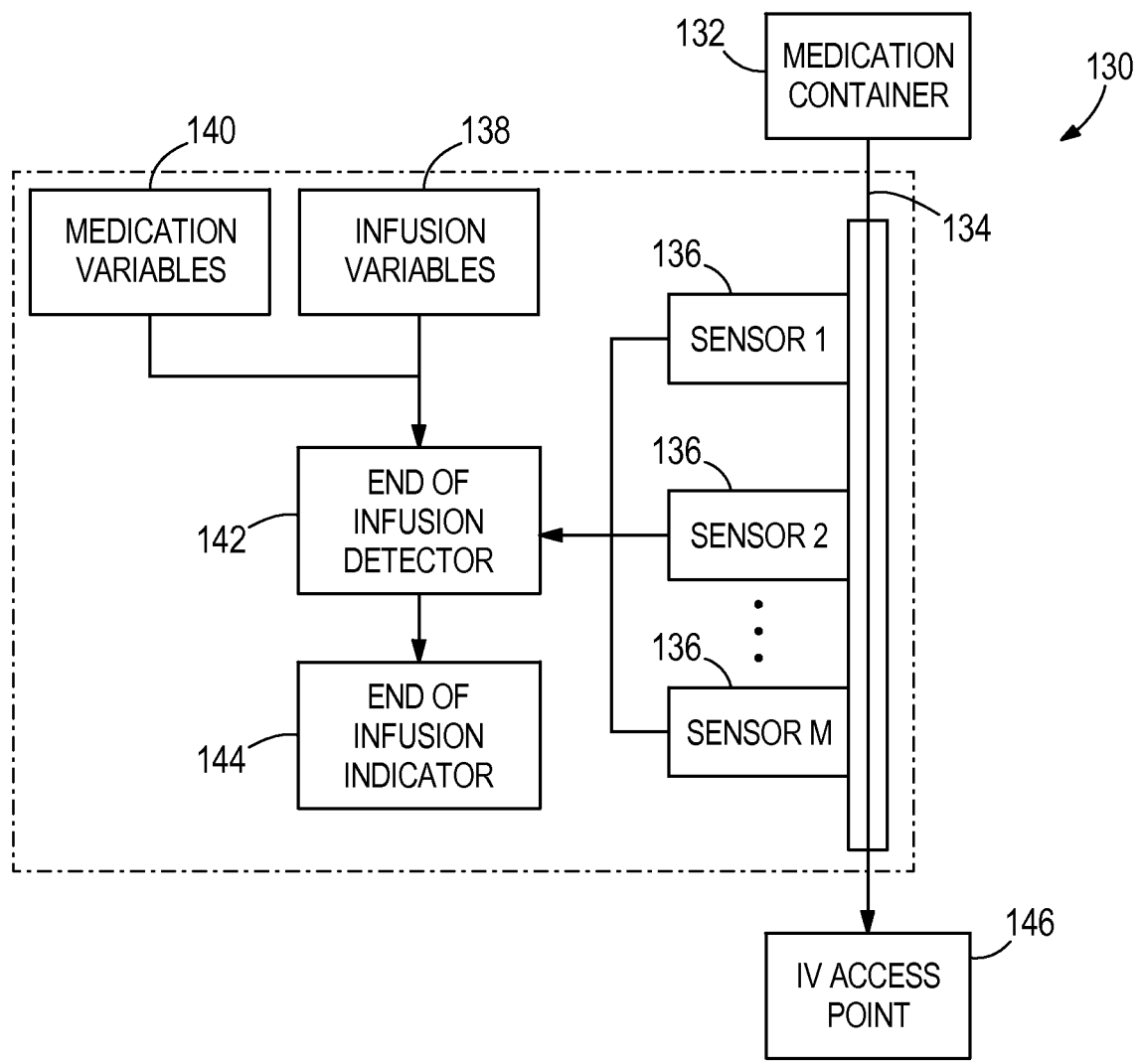
FIG. 3 illustrates a block diagram showing some portions of an infusion system under another embodiment of the disclosure.

FIG. 3 illustrates a block diagram showing some portions of an infusion system 130 under another embodiment of the disclosure. The infusion system 130 comprises: an infusion container 132; a fluid delivery line 134; a plurality of sensors 136; infusion information 138; medication information 140; an end of infusion detector 142; an end of infusion indicator 144; and a delivery/extraction device 146. For ease of illustration the pumping device, the processing device/memory, the input/output device, and the alarm device are not shown in FIG. 3. The infusion system 130 may comprise an infusion system such as the Plum™, Gemstar™, Symbig™, or other type of infusion system.

Infusion fluid is delivered from the infusion container 132 through the fluid delivery line 134 through the delivery/extraction device 146 to a patient. The plurality of sensors 136 take measurements during the infusion. The plurality of sensors 136 may comprise any combination, number, or configuration of one or more plunger force sensor, one or more proximal air sensor, one or more distal air sensor, one or more proximal pressure sensor, one or more chamber pressure sensor, one or more distal pressure sensor, or one or more varying other types of sensor. The infusion information 138 may comprise a volume of the infusion fluid in the infusion container 132 or another parameter regarding the infusion of the infusion fluid. The medication information 140 may comprise a formulation of the infusion fluid, a rate of the infusion fluid, a duration of the infusion fluid, a viscosity of the infusion fluid, a therapy of the infusion fluid, or a property of the infusion fluid. The infusion information 138 and the medication information 140 may be scanned in, entered by the clinician, auto-programmed, or inputted through varying means.

The end of infusion detector 142 may comprise one or more algorithms to be applied by programming code of a processing device to determine that the infusion container 132 is empty (i.e. the end of the infusion) or to determine whether or not air, fluid, or some combination thereof is present in the infusion system 130. In order to make this determination, the end of infusion detector 142 may rely on the infusion information 138, the medication information 140, and on varying features of the signals of the plurality of sensors 136 such as: mean values; variances; derivatives; principal component scores; frequencies; wavelet coefficients; shapes; distance metrics; threshold crossings; coherence between signals; correlation between signals; phase shifts; peak values; minimum values; or one or more other types of features. The end of infusion detector 142 may utilize varying methods to combine and classify the signals of the plurality of sensors 136 such as: pattern recognition; Bayesian networks; support vector machines; linear discriminant analysis; decision trees; K nearest neighbor; template matching; thresholds/limits; normalization; digitization; factor decomposition; simple aggregation; or one or more other factors or information.

By using the varying type of information such as the information from the plurality of sensors 136, the infusion information 138, and the medication information 140, the end of infusion detector 142 determination as to whether or not the infusion container 132 is empty (i.e. the end of the bag, the end of the infusion, etc.) or whether or not air, fluid, or some combination thereof is contained in the infusion system 130 is more accurate and reliable and will lead to less nuisance alarms (when the alarm went off but shouldn't have) or missed alarms (when the alarm should have gone off but didn't). For instance, without the infusion information 138 or the medication information 140, the end of infusion detector 142 may merely rely on the information from the sensors 136 and incorrectly determine that the infusion container 132 is empty because an air slug during delivery has been detected by the sensors 136. However, this may be a temporary situation and the infusion container 132 may not in fact be empty. By relying on this varying information (such as the infusion information revealing that the infusion container is within 10% or less of being empty when the air slug is detected), the accuracy and reliability of the determination is substantially increased.

The end of infusion indicator 144 indicates, based on the determination of the end of infusion detector 142, whether or not the infusion container 132 is empty (i.e. the end of the infusion) or whether or not air, fluid, or some combination thereof is contained in the infusion system 130. The end of infusion indicator 144 may turn on an alarm indicating that the infusion container 132 is empty or that air is in the infusion system 130. The end of infusion indicator 144 may also turn off the infusion system 130 if the infusion container 132 is empty or if air is contained in the infusion system 130. In other embodiments, the infusion system 130 of FIG. 3 may be altered to vary the components, to take away one or more components, or to add one or more components.

Figure 4:
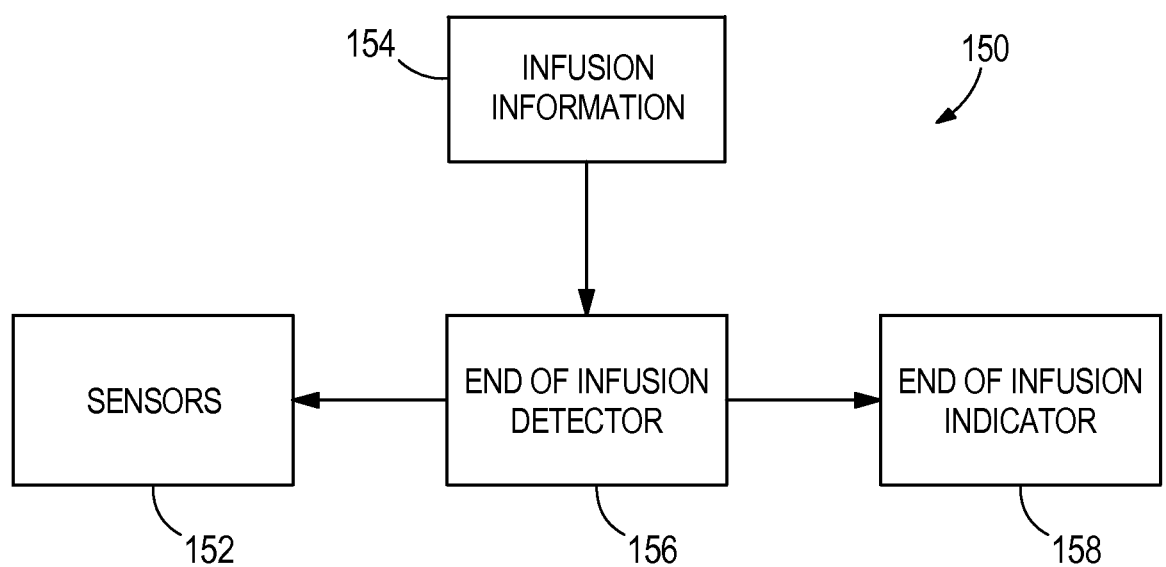
FIG. 4 illustrates a block diagram showing some portions of an infusion system under another embodiment of the disclosure.

FIG. 4 illustrates a block diagram showing some portions of an infusion system 150 under another embodiment of the disclosure. The infusion system 150 comprises: one or more sensors 152; infusion information 154; an end of infusion detector 156; and an end of infusion indicator 158. For ease of illustration the infusion container, the fluid delivery line, the pumping device, the processing device/memory, the input/output device, the delivery/extraction device, and the alarm device are not shown in FIG. 4. The infusion system 150 may comprise an infusion system such as the Plum™, Gemstar™, Symbig™, or other type of infusion system.

The one or more sensors 152 take measurements during the infusion. The one or more sensors 152 may comprise any combination, number, or configuration of one or more plunger force sensor, one or more proximal air sensor, one or more distal air sensor, one or more proximal pressure sensor, one or more chamber pressure sensor, one or more distal pressure sensor, or one or more varying other types of sensor. The infusion information 154 may comprise a volume of the infusion fluid in the infusion container, volume to be infused (VTBI), or another parameter regarding the infusion of the infusion fluid. The infusion information 154 may be scanned in, entered by the clinician, auto-programmed, or inputted through varying means.

The end of infusion detector 156 may comprise one or more algorithms to be applied by programming code of a processing device to determine that the infusion container is empty (i.e. the end of the infusion) or to determine whether or not air, fluid, or some combination thereof is contained in the infusion system 150. In order to make this determination, the end of infusion detector 156 may rely on the measurements taken by the one or more sensors 152 and on the infusion information 154.

By using the varying type of information such as the information from the one or more sensors 152 and the infusion information 154, the end of infusion detector 156 makes a determination as to whether or not the infusion container is empty (i.e. the end of the bag, the end of the infusion, etc.) or whether or not air, fluid, or some combination thereof is contained in the infusion system 150. This determination is more accurate and reliable and will lead to less nuisance alarms (when the alarm went off but shouldn't have) or missed alarms (when the alarm should have gone off but didn't) due to the use of the varying information.

The end of infusion indicator 158 indicates, based on the determination of the end of infusion detector 156, whether or not the infusion container is empty (i.e. the end of the infusion) or whether or not air, fluid, or some combination thereof is contained in the infusion system 150. The end of infusion indicator 158 may turn on an alarm indicating that the infusion container is empty or that air is in the infusion system 150. The end of infusion indicator 158 may also turn off the infusion system 150 if the infusion container is empty or if air is contained in the infusion system 150. In other embodiments, the infusion system 150 of FIG. 4 may be altered to vary the components, to take away one or more components, or to add one or more components. For instance, in another embodiment instead of relying on the measurements of one or more sensor and on the infusion information, the end of infusion detector may rely on the measurements of one or more sensor and on the medication information. In other embodiments, the end of infusion detector may rely on varying combinations of information.

Figure 5:
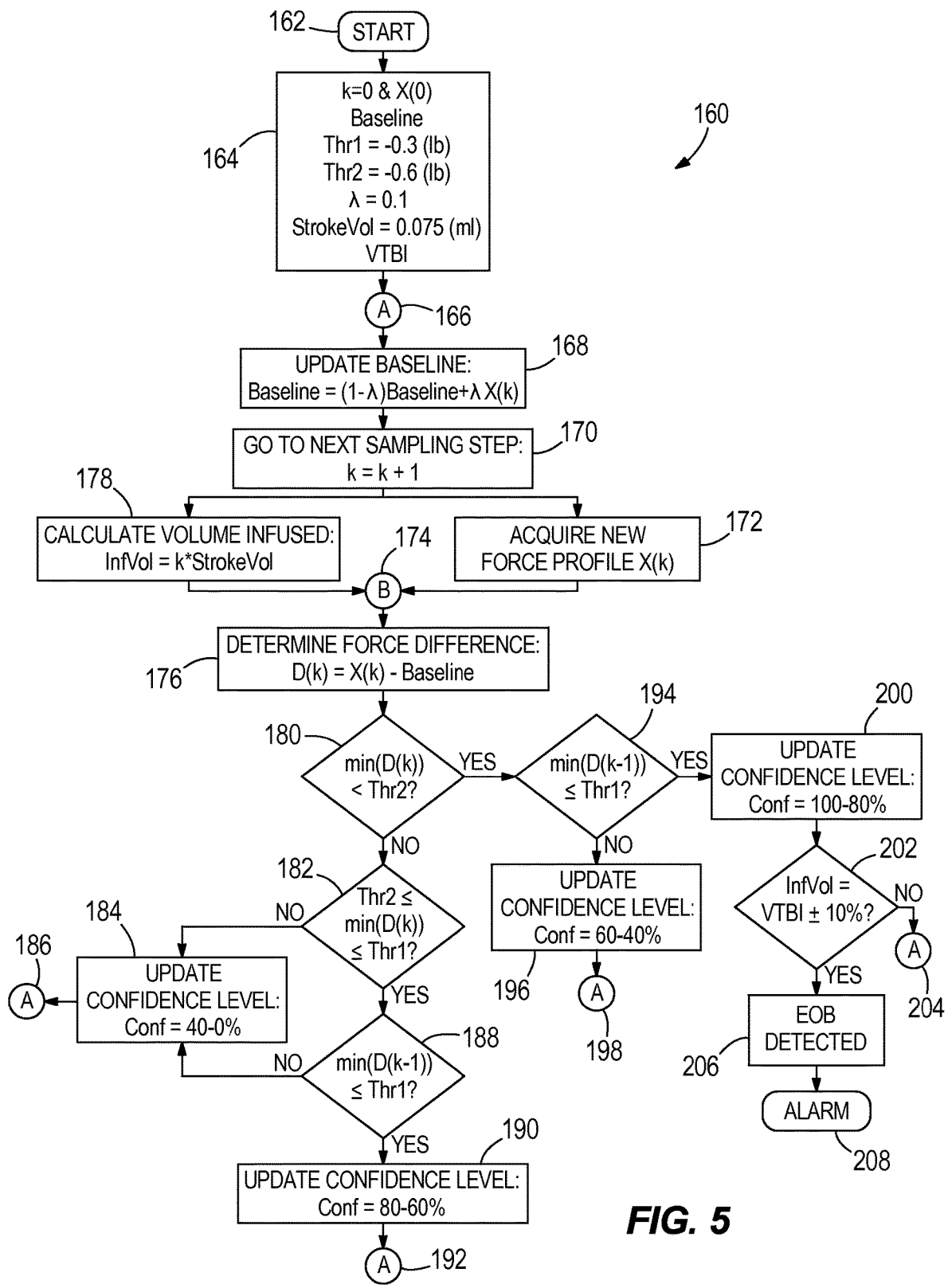
FIG. 5 illustrates a flowchart of one embodiment of a method for determining confidence levels of air being disposed in an infusion system and for determining whether an infusion container has been emptied of infusion fluid.

FIG. 5 illustrates a flowchart of one embodiment of a method 160 for determining confidence levels of air being disposed in an infusion system and for determining whether an infusion container has been emptied of infusion fluid. It can be applied to any air-in-line algorithm as long as it outputs a force profile at each sampling step (throughout this disclosure the term 'sampling step' corresponds to the current pumping cycle and the term 'previous sampling step' corresponds to the previous pumping cycle) and as long as it keeps track of how many strokes the pumping cycle has undergone. The method 160 determines at each sampling step a force difference between the force profile and a baseline, and also determines the total volume of infusion fluid infused to present. The method 160 compares the force difference at each sampling step to multiple thresholds for air detection and based on where the force difference falls relative to the multiple thresholds determines a confidence level of air being contained in the infusion system. If the confidence level is between 80 to 100 percent that air is contained in the infusion system then the method 160 determines whether the total volume of infusion fluid which has been infused is within 10% of the total volume of infusion fluid contained within the infusion container. If it is, then the method 160 determines that the container has been emptied of the infusion fluid (i.e. the end of bag has been reached) and turns on an alarm to notify the user and/or to shut down the infusion system. By using varying types of information (i.e. infusion information such as the total volume of infusion fluid to be infused, and the sensor measurement information) the accuracy and reliability of the end of bag detection is increased. The method 160 may utilize the system of FIG. 1. In other embodiments, the method 160 may utilize varying systems.

In step 162, the method starts. The method proceeds from step 162 to step 164. In step 164, the variables are set including setting sampling step k=0, setting the initial force profile X(0) associated with fluid, setting a Baseline force profile for fluid, setting a first threshold Thr1 for air detection (for instance by setting Thr1=−0.3 pounds in one embodiment), setting a second threshold Thr2 for air detection (for instance by setting Thr2=−0.6 pounds in one embodiment), setting a forgetting factor A (for instance by setting A=0.1), setting a stroke volume Stroke Vol delivered by one stroke (for instance by setting Stroke Vol=0.075 ml), and by setting a volume to be infused VTBI (for instance a user-specified volume such as 500 ml). It is noted that the Baseline force profile for fluid represents a Baseline plurality of force readings representing the Baseline force profile at each stroke k of the pump. For instance, in one embodiment the Baseline force profile may comprise six representative force readings representing fluid at six points of a stroke k of the pump. In other embodiments, the Baseline force profile may comprise any number of representative force readings representing fluid at various points of the stroke k of the pump. The first threshold Thr1, the second threshold Thr2, and the Baseline can be set to universal values or set for the particular type of medication to be infused.

The method proceeds from step 164 through location step 166 to step 168. In step 168, the baseline is updated using the equation Baseline=(1−A)*Baseline+A*X(k). By updating the Baseline at each cycle with an exponentially weighted forgetting factor, variability in the force profiles due to medication type, tubing type, pump motor control, ambient temperature, etc. may be accounted for. The method proceeds from step 168 to step 170. In step 170, the sampling step k is incremented using the equation k=k+1. The method proceeds from step 170 to step 172. In step 172, a force profile X(k) for the current sampling step k is acquired. It is noted that the force profile X(k) represents a plurality of force readings which are taken during each stroke k of the pump. For instance, in one embodiment six force readings may be taken at various points of each stroke k of the pump. In other embodiments, any number of force readings may be taken throughout each stroke k of the pump. The method proceeds from step 172 through location step 174 to step 176.

While the method proceeds from step 170 to step 172, the method also simultaneously proceeds from step 170 to step 178. In step 178, the total volume infused as of the present sampling step k is calculated using the equation InfVol=k*Stroke Vol. The method proceeds from step 178 through location step 174 to step 176.

In step 176, the force difference D(k) at the current sampling step k is determined using the equation D(k)=X(k)−Baseline. Since the force profile X(k) and the Baseline each comprise a plurality of force readings this force difference will be a vector. The method proceeds from step 176 to step 180. In step 180, a determination is made as to whether the minimum value of the force difference min(D(k)) (i.e. the minimum value in the force difference vector) at the current sampling step k is less than the second threshold Thr2 using the equation min(D(k))<Thr2. If a determination is made in step 180 that the minimum value of the force difference min(D(k)) is not less than Thr2 (i.e. if min(D(k))≥Thr2) then the method proceeds from step 180 to step 182. In step 182, a determination is made as to whether the minimum value of the force difference min(D(k)) (i.e. the minimum value in the force difference vector) at the current sampling step k is greater than or equal to the second threshold Thr2 and less than or equal to the first threshold Thr1 using the equation Thr2≤min(D(k))≤Thr1. If a determination is made in step 182 that the minimum value of the force difference min(D(k)) at the current sampling step k is not greater than or equal to the second threshold Thr2 and less than or equal to the first threshold Thr1 (i.e. if either min(D(k))<Thr2 or if min(D(k))>Thr1) then the method proceeds from step 182 to step 184. In step 184, the confidence level Conf that there is air in the infusion system is set in the range of 0% to 40%. The method proceeds from step 184 through location step 186 through location step 166 to step 168 and repeats the process steps.

If a determination is made in step 182 that the minimum value of the force difference min(D(k)) at the current sampling step k is greater than or equal to the second threshold Thr2 and less than or equal to the first threshold Thr1 (i.e. if min(D(k))≥Thr2 and if min(D(k))≥Thr1) then the method proceeds from step 182 to step 188. In step 188, a determination is made as to whether the minimum force difference min(D(k−1)) at the preceding sampling step k−1 (i.e. the minimum value in the force difference vector at sampling step k−1) is less than or equal to the first threshold Thr1 using the equation min(D(k−1))≤Thr1. If the determination is made in step 188 that the minimum force difference min(D(k−1)) at the preceding sampling step k−1 is not less than or equal to the first threshold Thr1 (i.e. min(D(k−1))>Thr1) then the method proceeds from step 188 to step 184. In step 184, the confidence level Conf that there is air in the infusion system is set in the range of 0% to 40%. The method proceeds from step 184 through location step 186 through location step 166 to step 168 and repeats the process steps.

If a determination is made in step 188 that the minimum force difference min(D(k−1)) at the preceding sampling step k−1 is less than or equal to the first threshold Thr1 (i.e. min(D(k−1))≤Thr1) then the method proceeds from step 188 to step 190. In step 190, the confidence level Conf that there is air in the infusion system is set in the range of 60% to 80%. The method proceeds from step 190 through location step 192 through location step 166 to step 168 and repeats the process steps.

If a determination is made in step 180 that min(D(k)) is less than Thr2 (i.e. if min(D(k))<Thr2) then the method proceeds from step 180 to step 194. In step 194, a determination is made as to whether the minimum force difference min(D(k−1)) at the preceding sampling step k−1 (i.e. the minimum value in the force difference vector at sampling step k−1) is less than or equal to the first threshold Thr1 using the equation min(D(k−1))<Thr1. If a determination is made in step 194 that the minimum force difference min(D(k−1)) at the preceding sampling step k−1 is not less than or equal to the first threshold Thr1 (i.e. if min(D(k−1))>Thr1) then the method proceeds from step 194 to step 196. In step 196, the confidence level Conf that there is air in the infusion system is set in the range of 40% to 60%. The method proceeds from step 196 through location step 198 through location step 166 to step 168 and repeats the process steps.

If a determination is made in step 194 that the minimum force difference min(D(k−1)) at the preceding sampling step k−1 is less than or equal to the first threshold Thr1 (i.e. if min(D(k−1))≤Thr1) then the method proceeds from step 194 to step 200. In step 200, the confidence level Conf that there is air in the infusion system is set in the range of 80% to 100%. The method proceeds from step 200 to step 202. In step 202, a determination is made as to whether the total volume infused to present InfVol is within 10% of the total volume of the infusion fluid to be infused VTBI using the equation InfVol=VTBI±10%. If the determination is made in step 202 that the total volume infused to present InfVol is not within 10% of the total volume of the infusion fluid to be infused VTBI (i.e. InfVol:it VTBI±10%) then the method proceeds from step 202 through location step 204 through location step 166 to step 168 and repeats the process steps. It is noted that even though there is a high confidence level in a range of 80% to 100% that air is contained in the infusion system, that since the volume of infusion fluid infused to present is not within 10% of the total volume to be infused that the air in the system must be due to one or more slugs of air and is not due to an end of container (end of bag) event.

If the determination is made in step 202 that the total volume infused to present InfVol is within 10% of the total volume of the infusion fluid to be infused VTBI (i.e. InfVol=VTBI±10%) then the method proceeds from step 202 to step 206. In step 206, an end of container event (i.e. end of bag event) is detected in which the infusion container has been emptied of the infusion fluid. It is important to note that since the minimum of the force difference min(D(k)) for the current sampling step k is less than the second threshold Thr2, the minimum of the force difference min(D(k−1)) for the preceding sampling step k−1 is less than or equal to the first threshold Thr1, and the total volume infused to present InfVol is within 10% of the total volume of the infusion fluid to be infused InfVol that the determination that the end of the container has been reached is highly accurate and reliable. The method proceeds from step 206 to step 208. In step 208, the alarm is turned on indicating that the infusion container has been emptied of the infusion fluid. When the alarm is generated or turned on in step 208, the infusion system may be turned off automatically or manually by the user to stop the infusion of the infusion fluid.

In other embodiments, the method 160 may be altered to vary the order or substance of any of the steps, to delete one or more of the steps, or to add one or more steps. For instance, instead of using force sensor measurements, one or more other types of sensors may be used (i.e. pressure, air, rate, temperature, etc.) and instead of using the infusion information comprising the volume to be infused (VTBI) one or more other types of information may be used (i.e. other types of infusion information as disclosed herein, medication information as disclosed herein, etc.). In still other embodiments, any number, type, and configuration of sensor information, infusion information, medication information, or other types of information may be used.

Figure 6:
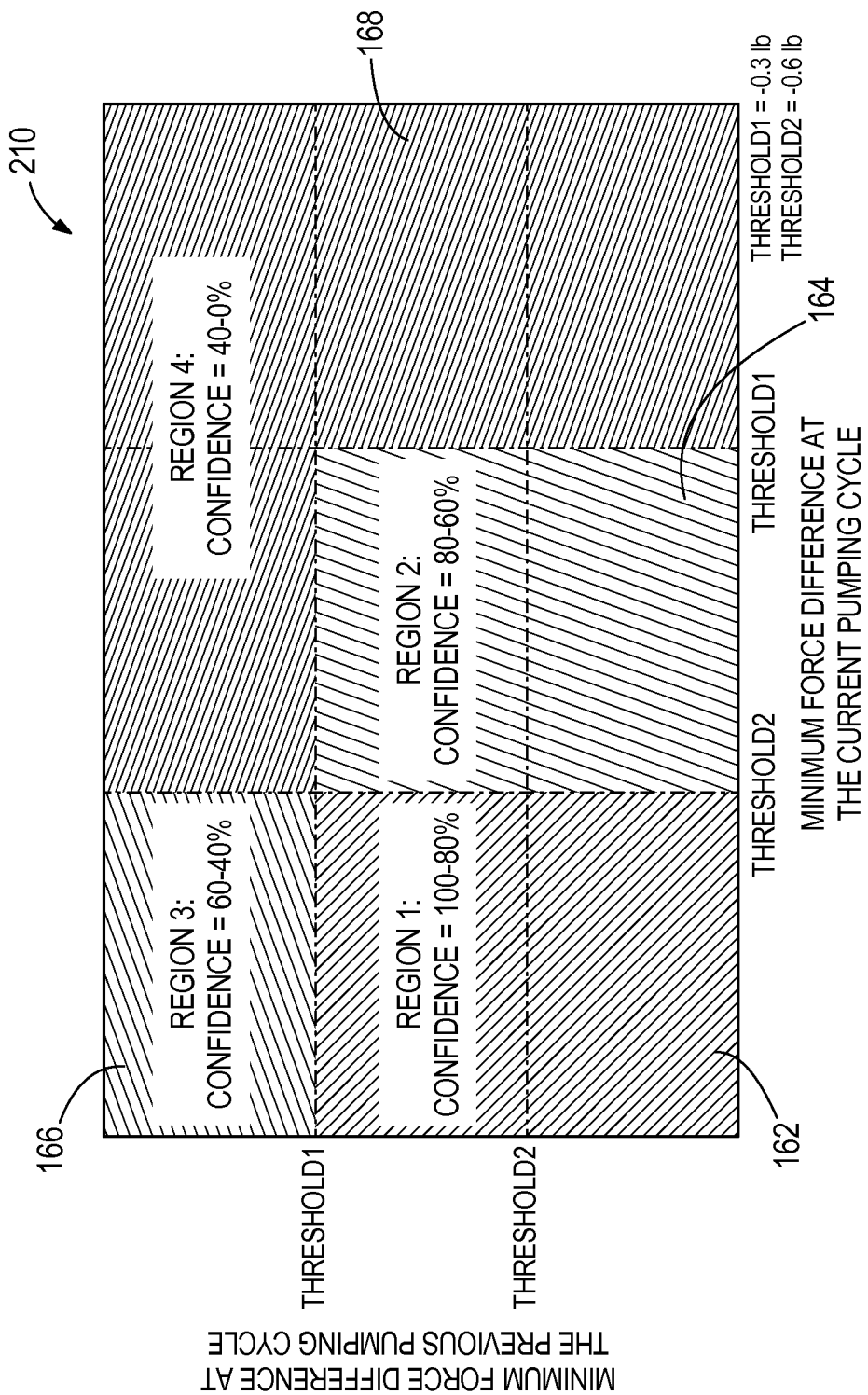
FIG. 6 illustrates a graph plotting various confidence regions corresponding to the confidence regions that air is present in the infusion system determined using the method of FIG. 5.

FIG. 6 illustrates a graph 210 plotting various confidence regions corresponding to the confidence regions that air is in the infusion system determined using the method 160 of FIG. 5. Plotted on the X-axis is the minimum force difference D(k) at the current sampling step k with D(k)=X(k)−Baseline as discussed in FIG. 5. Plotted on the Y-axis is the minimum force difference D(k−1) at the previous sampling step k−1 with D(k−1)=X(k−1)−Baseline as discussed in FIG. 5. The first threshold Thr1 is −0.3 pounds. The second threshold Thr2 is −0.6 pounds.

As shown, confidence region 162 represents having a confidence level in a range of 80% to 100% that air is in the infusion system. In confidence region 162 one of the following is true: (i) in two consecutive sampling steps (cycles) k−1 and k the minimum force difference D(k−1) and D(k) was less than the second threshold Thr2 (e.g. the last two drops in the force reading were very large in magnitude); or (ii) in the current sampling step k the minimum force difference D(k) is less than the second threshold Thr2 and the minimum force difference D(k−1) for the preceding sampling step k−1 was between the second threshold Thr2 and the first threshold Thr1 (e.g. the current drop in force reading is very large and the previous drop was large in magnitude). It is noted that fluid is less compressible than air so when transitioning from fluid to air a drop in the force profile X(k) and correspondingly a drop in the force difference D(k) is expected.

Confidence region 164 represents having a confidence level in a range of 60% to 80% that air is in the infusion system. In confidence region 164 one of the following is true: (i) in two consecutive sampling steps (cycles) k−1 and k the minimum force difference D(k−1) and D(k) is between the second threshold Thr2 and the first threshold Thr1 (e.g. the last two drops in force readings were large); or (ii) the current minimum force difference D(k) is between the second threshold Thr2 and the first threshold Thr1 and the previous minimum force difference D(k−1) was lower than the second threshold Thr2 (e.g. the current drop in force reading is large and the previous drop in force reading was very large).

Confidence region 166 represents having a confidence level in a range of 40% to 60% that air is in the infusion system. In confidence region 166 the current minimum force difference D(k) is lower than the second threshold Thr2 and the previous minimum force difference D(k−1) was higher than the first threshold Thr1 (e.g. the current drop in force reading is very large and the previous drop in force reading was small or non-existent).

Confidence region 168 represents having a confidence level in a range of 0% to 40% that air is in the infusion system. In confidence region 168 one of the following is true: (i) the current minimum force difference D(k) is higher than the first threshold Thr1 (e.g. the current drop in force reading is very small or non-existent); or (ii) the current minimum force difference D(k) is between the second threshold Thr2 and the first threshold Thr1 and the previous minimum force difference D(k−1) was higher than the first threshold Thr1 (e.g. the current drop in force reading is large and the previous drop in force reading was small or non-existent). In other embodiments, the algorithms used by the method 160 of FIG. 5 can be changed so that the number of thresholds and confidence regions can be varied depending on whether more or less sensitivity is desired.

Figure 7:
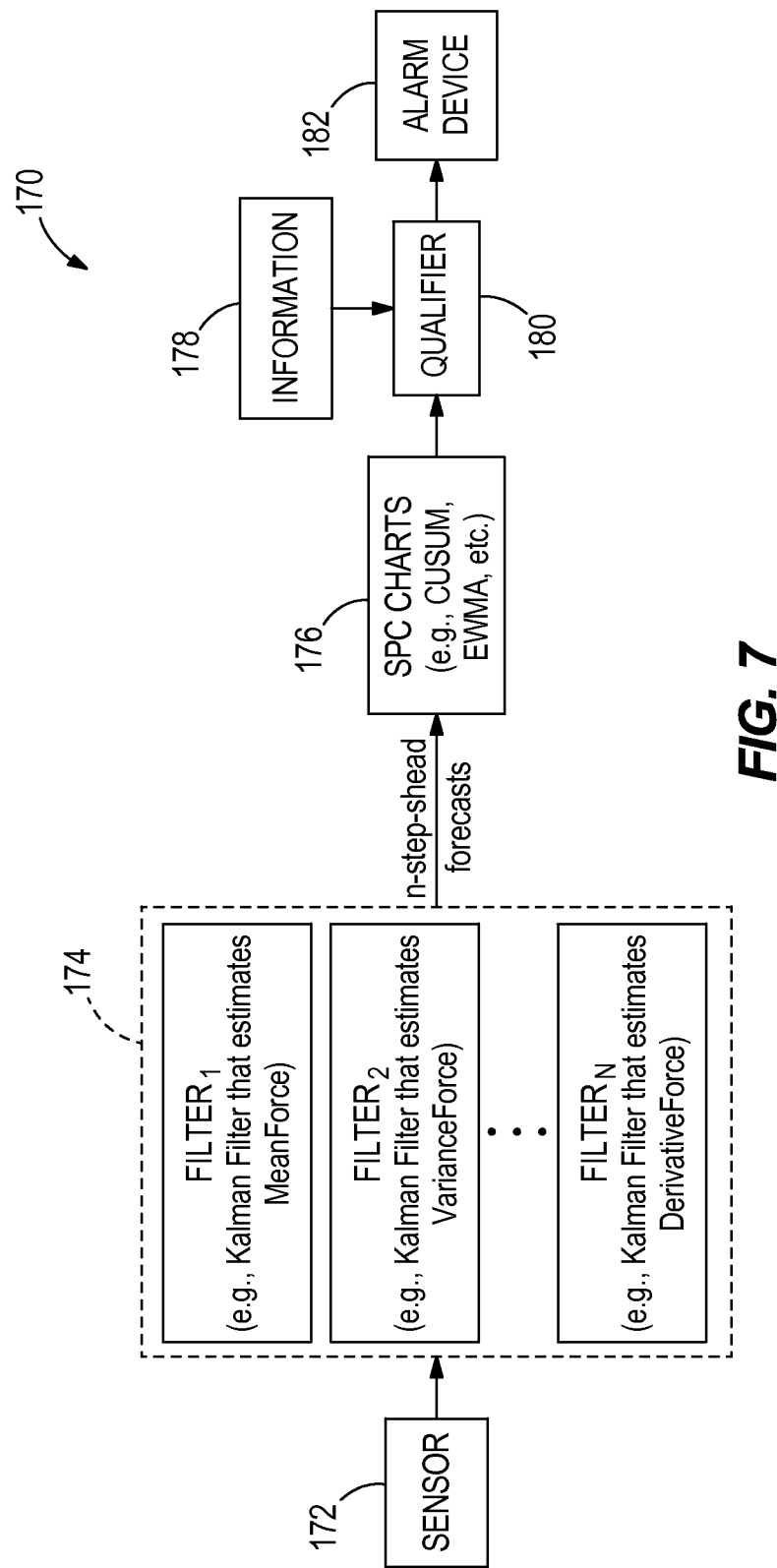
FIG. 7 illustrates a block diagram showing some portions of an infusion system under another embodiment of the disclosure.

FIG. 7 illustrates a block diagram showing some portions of an infusion system 170 under another embodiment of the disclosure. The infusion system 170 comprises: a sensor 172; a plurality of filters 174; one or more statistical process control (SPC) charts 176; information 178; one or more qualifiers 180; and an alarm device 182. For ease of illustration the infusion container, the fluid delivery line, the pumping device, the processing device/memory, the input/output device, and the delivery/extraction device are not shown in FIG. 7. The infusion system 170 may comprise an infusion system such as the Plum™ Gemstar™, Symbig™, or other type of infusion system.

The sensor 172 comprises a plunger force sensor which takes measurements during the infusion. In other embodiments, the sensor 172 may comprise any combination, number, or configuration of one or more plunger force sensors, one or more proximal air sensors, one or more distal air sensors, one or more proximal pressure sensors, one or more chamber pressure sensors, one or more distal pressure sensors, or one or more varying other type of sensors.

The plurality of filters 174 comprises a Kalman filter for estimating mean force based on the measurements of the sensor 172, a second Kalman filter for estimating variance force based on the measurements of the sensor 172, and a third Kalman filter for estimating derivative force based on the measurements of the sensor 172. In other embodiments, any number, type, and configuration of filters may be used to filter the measurements of the sensor 172 to determine varying information regarding the measurements of the sensor 172.

The one or more SPC charts 176 may comprise any number and type of SPC chart which are constructed based on the forecasted n-steps ahead filtered measurements of the sensor 172. For instance, a cumulative sum control chart (CUSUM chart), an exponentially weighted moving average control chart (EWMA chart), or other types of charts may be constructed based on the forecasted n-steps ahead filtered measurements of the sensor 172.

The information 178 comprises infusion information comprising the volume of the infusion fluid in the infusion container. In other embodiments, the information may comprise varying types of infusion information, may comprise medication information, or may comprise one or more other types of information. The medication information may comprise a formulation of the infusion fluid, a rate of the infusion fluid, a duration of the infusion fluid, a viscosity of the infusion fluid, a therapy of the infusion fluid, or a property of the infusion fluid. In other embodiments, one or more other type of information may be used.

The qualifier 180 may comprise one or more algorithms to be applied by programming code of a processing device to determine that the infusion container is empty (i.e. the end of the infusion) or to determine whether or not air, fluid, or some combination thereof is contained in the infusion system 170. In order to make this determination, the qualifier 180 may rely on the constructed SPC charts 176 and on the information 178. This determination is more accurate and reliable and will lead to less nuisance alarms (when the alarm went off but shouldn't have) or missed alarms (when the alarm should have gone off but didn't) due to the use of the varying types of information used. In other embodiments, the qualifier 180 may rely on varying information to make the determination.

The alarm device 182 may generate or turn on an alarm to indicate that the infusion container is empty if the qualifier 180 determines that the infusion container is empty or if it determines that air is contained in the infusion system. In this event, the alarm device 182 may further automatically or manually turn off the infusion system to stop the infusion. In other embodiments, the infusion system 170 of FIG. 7 may be altered to vary the components, to take away one or more components, or to add one or more components.

Figure 8:
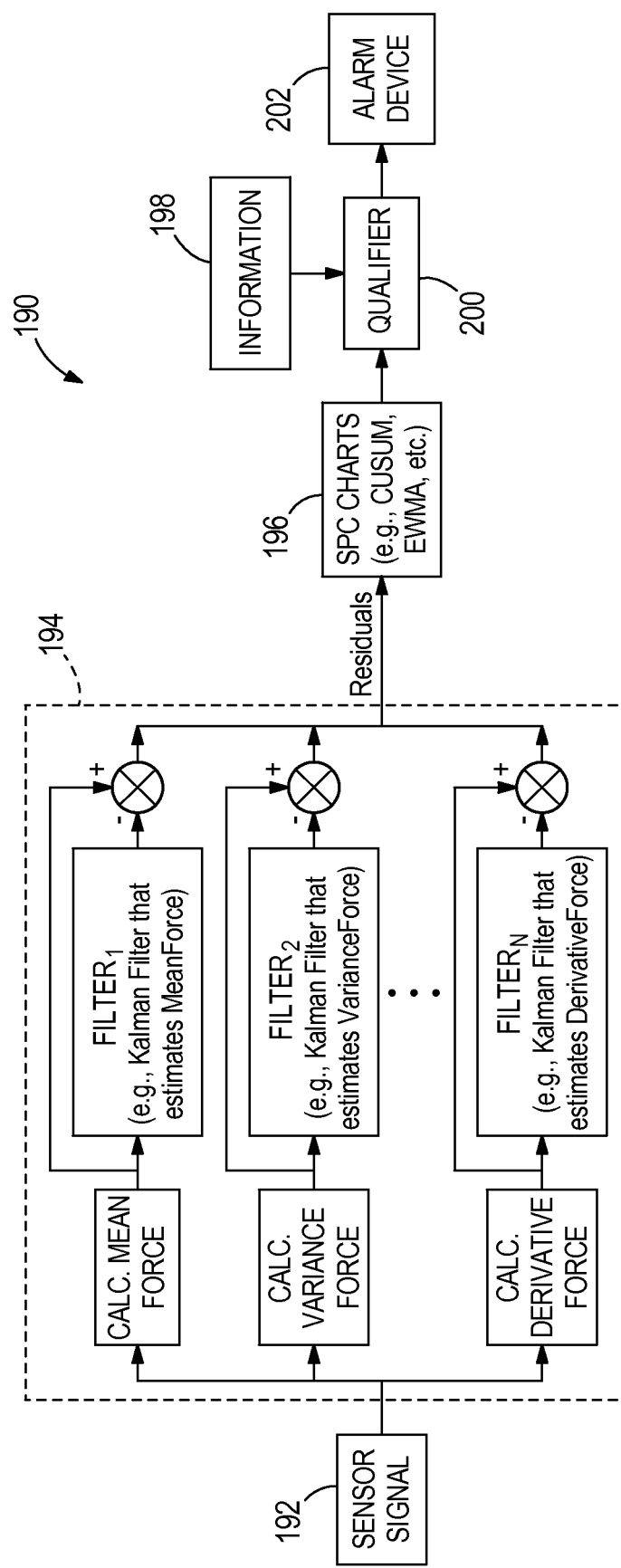
FIG. 8 illustrates a block diagram showing some portions of an infusion system under another embodiment of the disclosure.

FIG. 8 illustrates a block diagram showing some portions of an infusion system 190 under another embodiment of the disclosure. The infusion system 190 comprises: a sensor 192; a plurality of filters 194; one or more statistical process control (SPC) charts 196; information 198; one or more qualifiers 200; and an alarm device 202. For ease of illustration the infusion container, the fluid delivery line, the pumping device, the processing device/memory, the input/output device, and the delivery/extraction device are not shown in FIG. 8. The infusion system 190 may comprise an infusion system such as the Plum™ Gemstar™, Symbig™, or other type of infusion system.

The sensor 192 comprises a plunger force sensor which takes measurements during the infusion. In other embodiments, the sensor 192 may comprise any combination, number, or configuration of one or more plunger force sensors, one or more proximal air sensors, one or more distal air sensors, one or more proximal pressure sensors, one or more chamber pressure sensors, one or more distal pressure sensors, or one or more varying other type of sensors.

The plurality of filters 194 comprises a Kalman filter for estimating mean force based on the measurements of the sensor 192, a second Kalman filter for estimating variance force based on the measurements of the sensor 192, and a third Kalman filter for estimating derivative force based on the measurements of the sensor 192. In other embodiments, any number, type, and configuration of filters may be used to filter the measurements of the sensor 192 to determine varying information regarding the measurements of the sensor 192.

The one or more SPC charts 196 may comprise any number and type of SPC chart which are constructed based on the residuals of the filtered measurements of the sensor 192. The residual is defined as the difference between the actual signal characteristic as measured (for instance the actual plunger force measurement) and the estimated/expected/anticipated signal characteristic via the filtering (for instance the estimated/expected/anticipated plunger force measurement as a result of the filtering). A cumulative sum control chart (CUSUM chart), an exponentially weighted moving average control chart (EWMA chart), or other types of charts may be constructed based on the residuals of the filtered measurements of the sensor 192.

The information 198 comprises infusion information comprising the volume of the infusion fluid in the infusion container. In other embodiments, the information may comprise varying types of infusion information, may comprise medication information, or may comprise one or more other types of information. The medication information may comprise a formulation of the infusion fluid, a rate of the infusion fluid, a duration of the infusion fluid, a viscosity of the infusion fluid, a therapy of the infusion fluid, or a property of the infusion fluid. In other embodiments, one or more other type of information may be used.

The qualifier 200 may comprise one or more algorithms to be applied by programming code of a processing device to determine that the infusion container is empty (i.e. the end of the infusion) or to determine whether or not air, fluid, or some combination thereof is contained in the infusion system 190. In order to make this determination, the qualifier 200 may rely on the constructed SPC charts 196 and on the information 198. This determination is more accurate and reliable and will lead to less nuisance alarms (when the alarm went off but shouldn't have) or missed alarms (when the alarm should have gone off but didn't) due to the use of the varying types of information used. In other embodiments, the qualifier 200 may rely on varying information to make the determination.

The alarm device 202 may generate or turn on an alarm to indicate that the infusion container is empty if the qualifier 200 determines that the infusion container is empty or if it determines that air is contained in the infusion system. In this event, the alarm device 202 may further automatically or manually turn off the infusion system to stop the infusion. In other embodiments, the infusion system 190 of FIG. 8 may be altered to vary the components, to take away one or more components, or to add one or more components.

Figure 9:
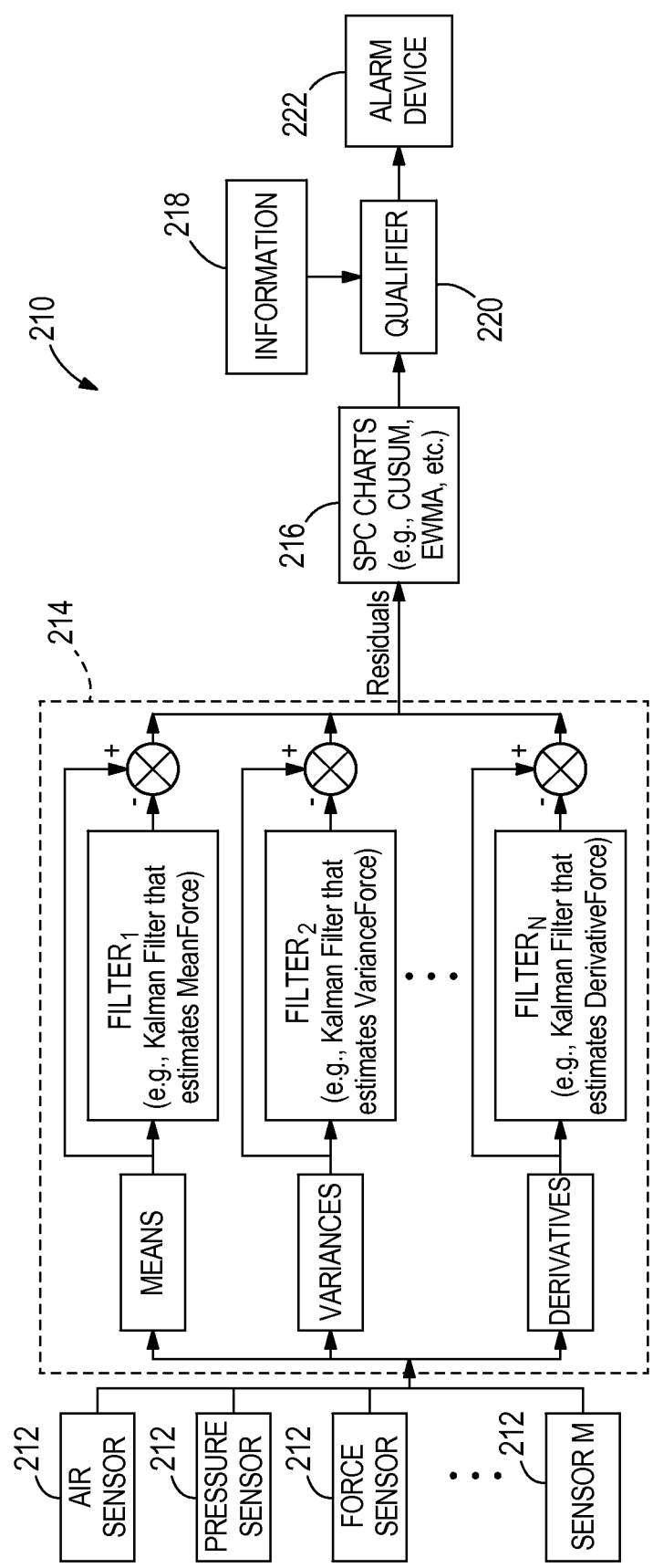
FIG. 9 illustrates a block diagram showing some portions of an infusion system under another embodiment of the disclosure.

FIG. 9 illustrates a block diagram showing some portions of an infusion system 210 under another embodiment of the disclosure. The infusion system 210 comprises: a plurality of sensors 212; a plurality of filters 214; one or more statistical process control (SPC) charts 216; information 218; one or more qualifiers 220; and an alarm device 222. For ease of illustration the infusion container, the fluid delivery line, the pumping device, the processing device/memory, the input/output device, and the delivery/extraction device are not shown in FIG. 9. The infusion system 210 may comprise an infusion system such as the Plum™, Gemstar™, Symbig™, or other type of infusion system.

The plurality of sensors 212 comprise an air sensor, a pressure sensor, a force sensor, and any number and type of other sensors that are desired to take measurements during the infusion. In other embodiments, any number, type, and configuration of sensors may be used to take measurements during the infusion.

The plurality of filters 214 comprises a Kalman filter for estimating mean force based on the measurements of the sensors 212, a second Kalman filter for estimating variance force based on the measurements of the sensors 212, and a third Kalman filter for estimating derivative force based on the measurements of the sensors 212. In other embodiments, any number, type, and configuration of filters may be used to filter the measurements of the sensors 212 to determine varying information regarding the measurements of the sensors 212.

The one or more SPC charts 216 may comprise any number and type of SPC chart which are constructed based on the residuals of the filtered measurements of the plurality of sensors 212. The residual is defined as the difference between the actual signal characteristic as measured (for instance the actual plunger force measurement) and the estimated/expected/anticipated signal characteristic via the filtering (for instance the estimated/expected/anticipated plunger force measurement as a result of the filtering). A cumulative sum control chart (CUSUM chart), an exponentially weighted moving average control chart (EWMA chart), or other types of charts may be constructed based on the residuals of the filtered measurements of the plurality of sensors 212.

The information 218 comprises infusion information comprising the volume of the infusion fluid in the infusion container or the volume to be infused (VBTI). In other embodiments, the information may comprise varying types of infusion information, may comprise medication information, or may comprise one or more other types of information. The medication information may comprise a formulation of the infusion fluid, a rate of the infusion fluid, a duration of the infusion fluid, a viscosity of the infusion fluid, a therapy of the infusion fluid, or a property of the infusion fluid. In other embodiments, one or more other type of information may be used.

The qualifier 220 may comprise one or more algorithms to be applied by programming code of a processing device to determine that the infusion container is empty (i.e. the end of the infusion) or to determine whether or not air, fluid, or some combination thereof is contained in the infusion system 210. In order to make this determination, the qualifier 220 may rely on the constructed SPC charts 216 and on the information 218. This determination is more accurate and reliable and will lead to less nuisance alarms (when the alarm went off but shouldn't have) or missed alarms (when the alarm should have gone off but didn't) due to the use of the varying types of information used. In other embodiments, the qualifier 220 may rely on varying information to make the determination.

The alarm device 222 may turn on an alarm to indicate that the infusion container is empty if the qualifier 220 determines that the infusion container is empty or if it determines that air is contained in the infusion system. In this event, the alarm device 222 may further automatically or manually turn off the infusion system to stop the infusion. In other embodiments, the infusion system 210 of FIG. 9 may be altered to vary the components, to take away one or more components, or to add one or more components.

Figure 10:
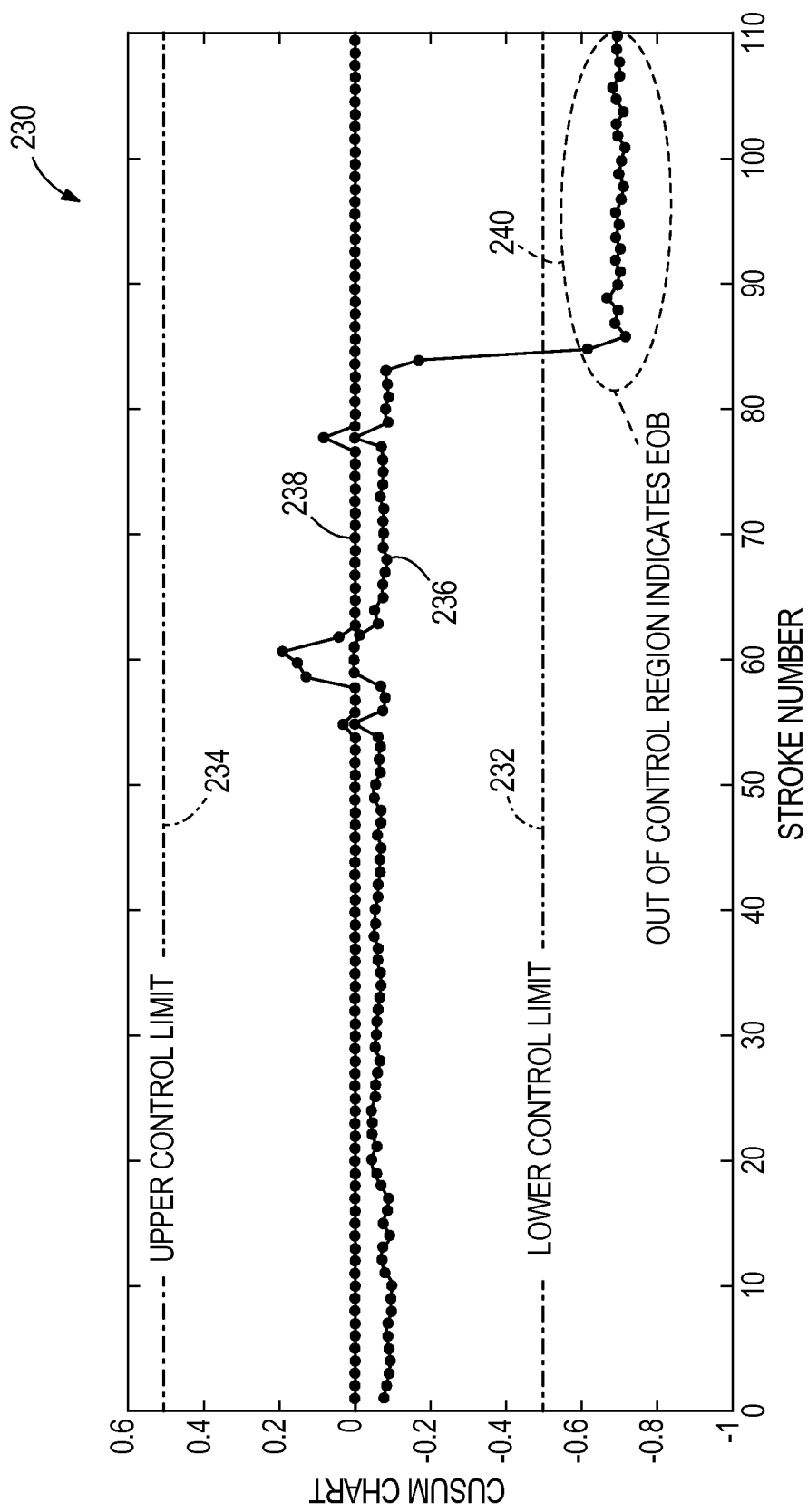
FIG. 10 illustrates a graph plotting SPC chart results for one embodiment of the disclosure using the system of FIG. 8 for end of bag detection.

FIG. 10 illustrates a graph 230 plotting SPC chart results for one embodiment of the disclosure using the system of FIG. 8 for end of bag detection (i.e. end of the infusion fluid in the infusion container). Plotted on the X-axis is the stroke number (also referred to as the sampling step herein) for the pump. Plotted on the Y-axis is a CUSUM SPC chart. The graph 230 was plotted based on the residuals (i.e. the difference) between the actual mean force of the signals measured by the sensors of FIG. 8 and the Kalman filter estimated mean force per pumping stroke during a test run on a Symbig™ pump using the system of FIG. 8.

Line 232 represents the lower control limit. Line 234 represents the upper control limit. Curve 236 represents the lower CUSUM that is the cumulative sum in the negative direction. Curve 238 represents the upper CUSUM that is the cumulative sum in the positive direction. Out of control area 240 represents an area where curve 236 drops below the lower control limit 232 and substantially deviates from curve 238 which clearly indicates that the infusion container has run out of infusion fluid (i.e. the end of the bag). This determination is buttressed because not only were the SPC charts constructed based on the sensor measurements but also infusion information was utilized ensuring that out of control area 240 is within 10% of the total volume of the infusion fluid in the infusion container. This provides increased accuracy to the determination, and reduces the risk of a nuisance alarm or a missed alarm.

Figure 11:
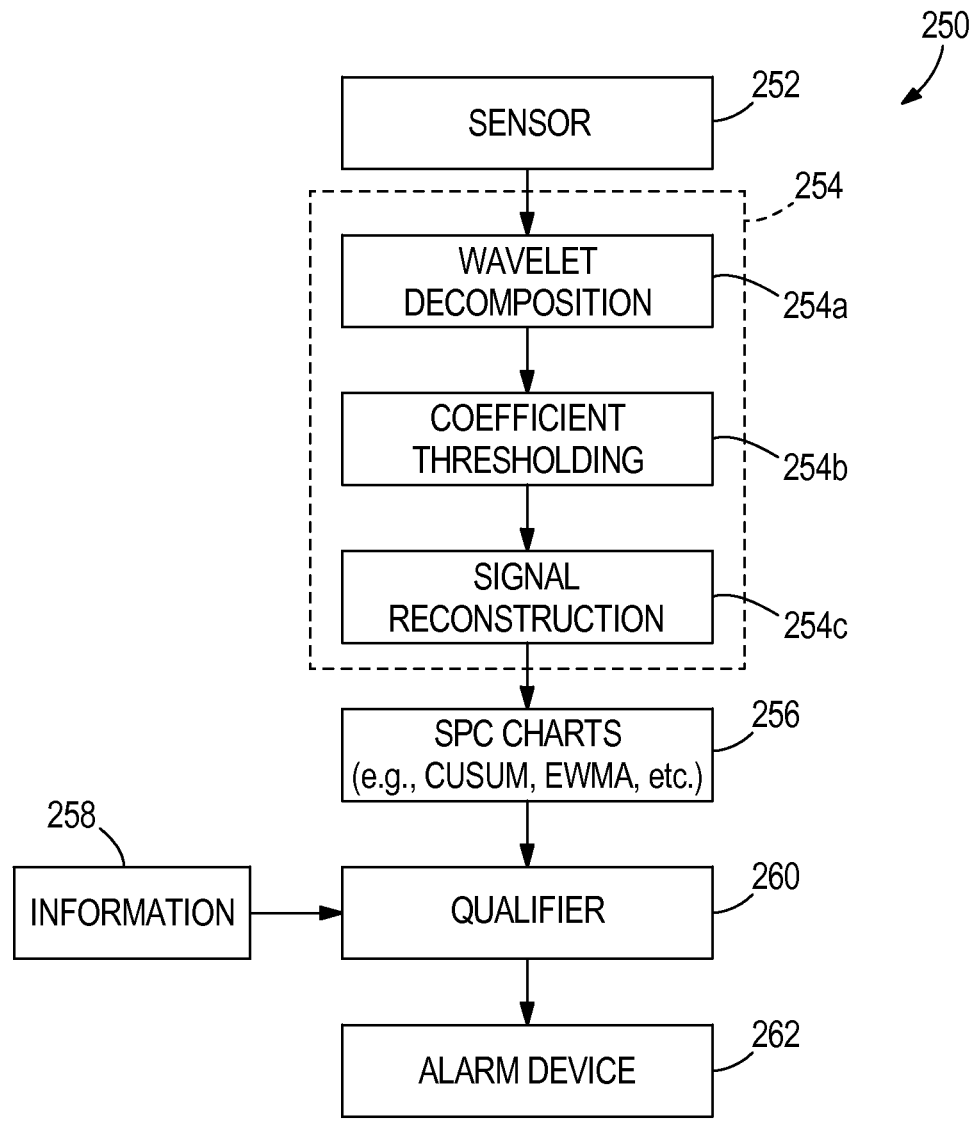
FIG. 11 illustrates a block diagram showing some portions of an infusion system under another embodiment of the disclosure.

FIG. 11 illustrates a block diagram showing some portions of an infusion system 250 under another embodiment of the disclosure. The infusion system 250 comprises: a sensor 252; a wavelet transform block 254; one or more statistical process control (SPC) charts 256; information 258; one or more qualifiers 260; and an alarm device 262. For ease of illustration the infusion container, the fluid delivery line, the pumping device, the processing device/memory, the input/output device, and the delivery/extraction device are not shown in FIG. 11. The infusion system 250 may comprise an infusion system such as the Plum™, Gemstar™, Symbig™, or other type of infusion system.

The sensor 252 comprises a plunger force sensor which takes measurements during the infusion. In other embodiments, the sensor 252 may comprise any combination, number, or configuration of one or more plunger force sensors, one or more proximal air sensors, one or more distal air sensors, one or more proximal pressure sensors, one or more chamber pressure sensors, one or more distal pressure sensors, or one or more varying other type of sensors.

The wavelet transform block 254 comprises a wavelet decomposition block 254a, a coefficient threshold block 254b, and a signal reconstruction block 254c. The wavelet decomposition block 254a decomposes the wavelet based on the plunger force sensor signal to obtain the wavelet coefficients. The coefficient threshold block 254b applies one or more thresholds to the obtained wavelet coefficients to remove the noise. The signal reconstruction block 254c applies an inverse wavelet transform to the threshold coefficients to obtain a de-noised signal. In other embodiments, any number, type, and configuration of wavelet transform blocks may be applied to the measurements of the sensor 252 to determine varying information regarding the measurements of the sensor 252.

The one or more SPC charts 256 may comprise any number and type of SPC chart which are constructed based on the de-noised signal obtained using the wavelet transform block 254. A cumulative sum control chart (CUSUM chart), an exponentially weighted moving average control chart (EWMA), or other types of charts may be constructed based on the de-noised signal obtained using the wavelet transform block 254.

The information 258 comprises infusion information comprising the volume of the infusion fluid in the infusion container. In other embodiments, the information may comprise varying types of infusion information, may comprise medication information, or may comprise one or more other types of information. The medication information may comprise a formulation of the infusion fluid, a rate of the infusion fluid, a duration of the infusion fluid, a viscosity of the infusion fluid, a therapy of the infusion fluid, or a property of the infusion fluid. In other embodiments, one or more other type of information may be used.

The qualifier 260 may comprise one or more algorithms to be applied by programming code of a processing device to determine that the infusion container is empty (i.e. the end of the infusion) or to determine whether or not air, fluid, or some combination thereof is contained in the infusion system 250. In order to make this determination, the qualifier 260 may rely on the constructed SPC charts 256 and on the information 258. This determination is buttressed because not only were the wavelet transform block used to construct SPC charts based on the plunger force sensor signal measurements but also infusion information was utilized ensuring that the out of control area was within a preset percentage of the total volume of the infusion fluid in the infusion container (e.g. 10% of the total volume of the infusion fluid in the infusion container). This determination is more accurate and reliable and will lead to less nuisance alarms (when the alarm went off but shouldn't have) or missed alarms (when the alarm should have gone off but didn't) due to the use of the varying types of information used. In other embodiments, the qualifier 260 may rely on varying information to make the determination.

The alarm device 262 may generate or turn on an alarm to indicate that the infusion container is empty if the qualifier 260 determines that the infusion container is empty or if it determines that air is contained in the infusion system. In this event, the alarm device 262 may further automatically or manually turn off the infusion system to stop the infusion. In other embodiments, the infusion system 250 of FIG. 11 may be altered to vary the components, to take away one or more components, or to add one or more components. For instance, in another embodiment the wavelet transform block 254 can be replaced by a neural network block.

Figure 12:
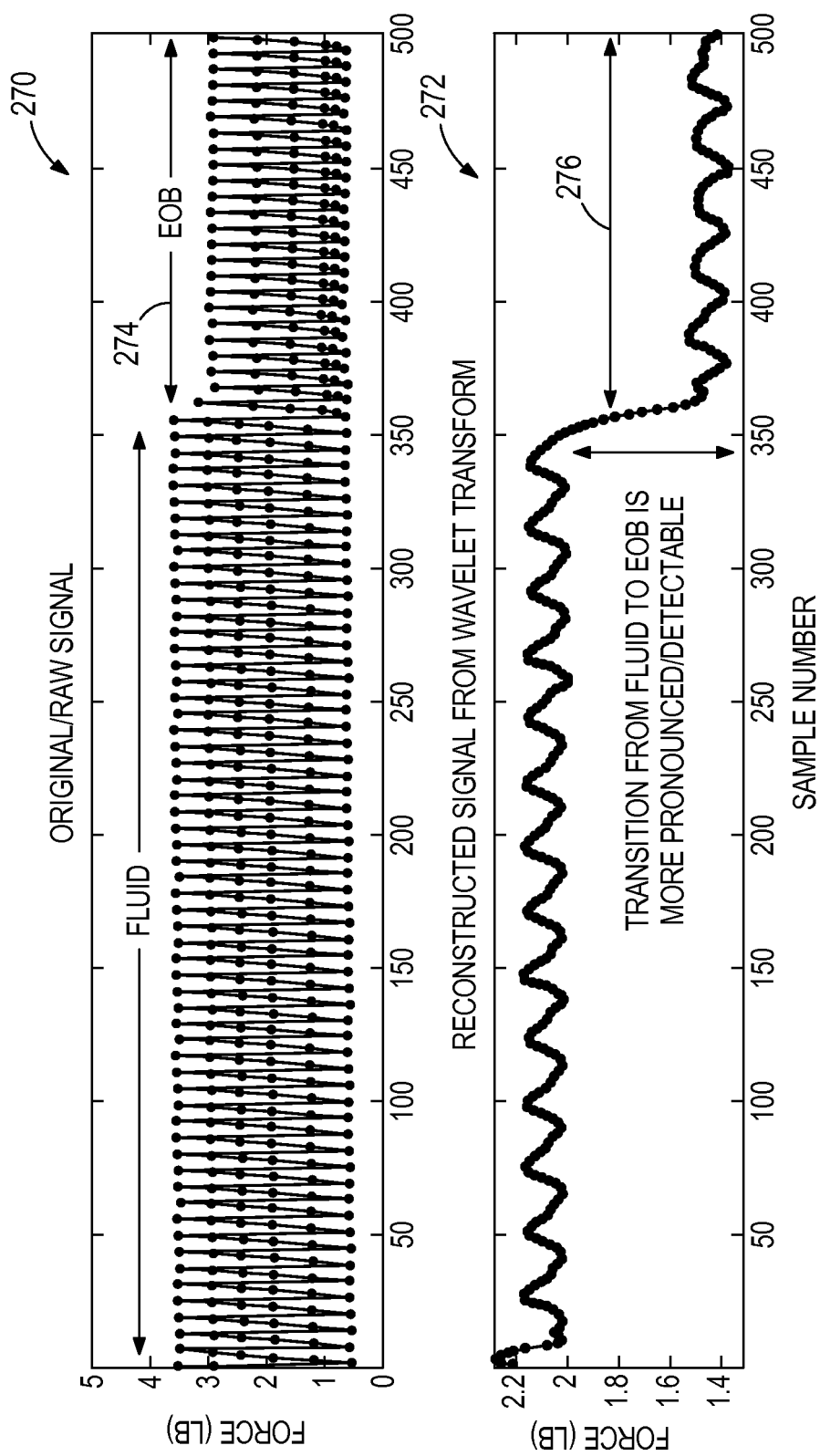
FIG. 12 illustrates two related graphs illustrating how the use of the infusion system of FIG. 11 to reconstruct a signal from a wavelet transform effectively determines when the infusion container has run out of infusion fluid.

FIG. 12 illustrates two related graphs 270 and 272 illustrating how the use of the infusion system of FIG. 11 to reconstruct a signal from a wavelet transform effectively determines when the infusion container has run out of infusion fluid. Graph 270 plots the original raw signal obtained using the sensor of FIG. 11 in a Symbig™ pump. The X-axis of graph 270 represents sample number of the pump cycles of the infusion system. The Y-axis of graph 270 represents the plunger force in pounds exerted on the plunger during the pumping of the infusion cycles. At area 274 there is an end of bag event in which the infusion container has been emptied of the infusion fluid. At area 274, the plunger force decreases slightly due to the decreased level of force applied to the plunger by air relative to fluid.

Graph 272 plots the reconstructed signal from the wavelet transform using the infusion system of FIG. 11. The X-axis of graph 272 represents sample number of the pump cycles of the infusion system. The Y-axis of graph 272 represents the plunger force in pounds exerted on the plunger during the pumping of the infusion cycles. At area 276 of graph 272, which corresponds to area 274 of graph 270, there is the same end of bag event in which the infusion container has been emptied of the infusion fluid. At area 276, the plunger force decreases greatly and is much more detectable then area 274 of graph 270 as a result of the application of the reconstructed signal from the wavelet transform using the infusion system of FIG. 11. This illustrates how applying the wavelet transform block to the measured signals of the sensor makes it much easier to detect an end of bag event, in addition to being much more reliable and accurate due to the varying types of information relied upon as detailed above.

All of the embodiments of the disclosure can be used to determine the presence of air in the pumping chamber and provide AIL (air-in-line) alarms. This can easily be achieved by excluding the information such as volume to the end of bag (VTBI) or other infusion information or medication information from the qualifier block(s). In current practice, the force algorithms developed to detect the presence of air in the chamber are typically based on singe-channel and linear filters/methods. However, the instant disclosure discloses systems and methods that utilize multi-channel filtering, non-linear mapping such as wavelet transform and neural networks, and SPC charts.

Alternate methodologies can be used to combine the diverse information provided by the varying sensors (such as force sensors, air sensors, and pressure sensors) and the additional information supplied such as the infusion information, the medication information, or other types of information. One such methodology comprises the application of a rule-based system that encompasses expert knowledge concerning the combination of events leading to the probability of an end-of-infusion event.

In another embodiment, a machine learning methodology may be used in which one or more pattern recognition systems are used to detect an end of infusion event on the basis of features extracted from the data elements. For this purpose, both parametric (linear discriminant analysis, support vector machines, artificial neural networks, logistic regression, Bayesian networks, dynamic Bayesian networks, etc.) and nonparametric (k-nearest-neighbor, decision trees, etc.) methods provide potential alternatives. This approach provides the option to uncover and learn complex patterns which occur through time to detect the likelihood of an end of infusion event.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. Furthermore, it is to be understood that the disclosure is defined by the appended claims. Accordingly, the disclosure is not to be restricted except in light of the appended claims and their equivalents.

The invention claimed is:

1. An infusion system configured to be connected to a fluid delivery line and to an infusion container containing an infusion fluid, the infusion system comprising:
 a pump;
 at least one sensor connected to the pump or the fluid delivery line, the at least one sensor configured to output a force profile at each sampling step;
 at least one processor in electronic communication with the pump and the at least one sensor; and
 a memory in electronic communication with the at least one processor, the memory comprising programming code for execution by the at least one processor;
 wherein the programming code is configured to cause the at least one processor to determine a total volume of infusion fluid infused at each sampling step and determine an air determination related to the air in the fluid delivery line based on statistical process control charts applied to multi-channel filtered measurements including the determined total volume of infusion fluid infused and the force profile from the at least one sensor.

2. The infusion system of claim 1, wherein the at least one sensor comprises a plunger force sensor, the plunger force sensor positioned on the pump.

3. The infusion system of claim 1, wherein the multi-channel filtered measurements comprise measurements filtered by a plurality of Kalman filters.

4. The infusion system of claim 3, wherein the plurality of Kalman filters comprise: a first Kalman filter configured to estimate mean force, a second Kalman filter configured to estimate variance force, and a third Kalman filter configured to estimate derivative force.

5. The infusion system of claim 1, wherein the statistical process control charts comprise a calculation of a residual value, the residual value comprising the difference between an actual signal characteristic measured by the at least one sensor and a predicted signal characteristic of the signal measured by the at least one sensor.

6. The infusion system of claim 5, wherein the statistical process control charts comprise a cumulative sum control chart.

7. The infusion system of claim 6, wherein the cumulative sum control chart comprises a cumulative sum of the residual values in a positive direction and a cumulative sum of the residual values in a negative direction.

8. The infusion system of claim 1, wherein the statistical process control charts comprise an exponentially moving average control chart.

9. An infusion system configured to be connected to a fluid delivery line and to an infusion container containing an infusion fluid, the infusion system comprising:
 a pump;
 at least one sensor connected to the pump or the fluid delivery line, the at least one sensor configured to output a force profile at each sampling step;
 at least one processor in electronic communication with the pump and the at least one sensor; and
 a memory in electronic communication with the at least one processor, wherein the memory comprises programming code for execution by the each at least one processor, and the programming code is configured to cause the at least one processor to determine an air determination related to the air in the fluid delivery line based on:
 (a) the force profile taken by the at least one sensor,
 (b) medication information regarding the infusion fluid, and
 (c) total volume of infusion fluid infused at each sampling step.

10. The infusion system of claim 9, wherein the medication information comprises a duration of the infusion fluid and the infusion information comprises a volume of the infused fluid in the infusion container.

11. The infusion system of claim 9, wherein the air determination is further determined by statistical process control charts applied to the measurements taken by the at least one sensor.

12. The infusion system of claim 9, wherein the air determination comprises determining an end-of-container event when the infusion container has been emptied of the infusion fluid.

13. An infusion system configured to be connected to a fluid delivery line and to an infusion container containing an infusion fluid, the infusion system comprising:
 a pump;
 at least one sensor connected to the pump or the fluid delivery line, the at least one sensor configured to output a force profile;
 at least one processor in electronic communication with the pump and the at least one sensor; and
 a memory in electronic communication with the at least one processor, the memory comprising programming code for execution by the at least one processor;
 wherein the programming code is configured to cause the at least one processor to determine an air determination related to the air in the fluid delivery line based on:
 (a) a total volume of infusion fluid infused; and
 (b) statistical process control charts applied to multi-channel filtered measurements including the determined total volume of infusion fluid infused and the force profile, wherein the multi-channel filtered measurements comprise measurements filtered by a plurality of Kalman filters.

* * * * *

UNITED STATES PATENT AND TRADEMARK OFFICE
CERTIFICATE OF CORRECTION

PATENT NO. : 11,433,177 B2  
APPLICATION NO. : 16/233740  
DATED : September 6, 2022  
INVENTOR(S) : Meriyan Oruklu et al.

It is certified that error appears in the above-identified patent and that said Letters Patent is hereby corrected as shown below:

On the Title Page

Page 13, Column 1 (item (56) Other Publications), Line 11, delete "release/" and insert -- releases/ --.

Page 13, Column 1 (item (56) Other Publications), Line 25, delete "Duhrdorf" and insert -- Buhrdorf --.

Page 14, Column 1 (item (56) Other Publications), Line 3, delete "Tang/SuganYaoQin" and insert -- TangSuganYaoQin --.

In the Specification

Column 2, Line 30, delete "multichannel" and insert -- multi-channel --.

Column 2, Line 49, delete "nonlinear" and insert -- non-linear --.

Column 3, Line 41, delete "Symbig™," and insert -- Symbiq™, --.

Column 5, Line 6, delete "Gemstar™ Symbig™," and insert -- Gemstar™, Symbiq™, --.

Column 8, Line 37-38, delete "Symbig™," and insert -- Symbiq™, --.

Column 9, Line 10, delete "Knearest" and insert -- K-nearest --.

Column 9, Line 59, delete "Symbig™," and insert -- Symbiq™, --.

Column 12, Line 59, delete "<" and insert -- $\leq$ --.

Column 13, Line 14, delete "InfVol:it" and insert -- InfVol:$\neq$ --.

Signed and Sealed this  
Twenty-seventh Day of December, 2022

Katherine Kelly Vidal  
*Director of the United States Patent and Trademark Office*

CERTIFICATE OF CORRECTION (continued)
U.S. Pat. No. 11,433,177 B2

Column 14, Line 64, delete "Plum™" and insert -- Plum™, --.

Column 14, Line 64, delete "Symbig™," and insert -- Symbiq™, --.

Column 16, Line 2, delete "Plum™" and insert -- Plum™, --.

Column 16, Line 2, delete "Symbig™," and insert -- Symbiq™, --.

Column 17, Line 13, delete "Symbig™," and insert -- Symbiq™, --.

Column 18, Line 23, delete "Symbig™," and insert -- Symbiq™, --.

Column 18, Line 51, delete "Symbig™," and insert -- Symbiq™, --.

Column 19, Line 12, delete "(EWMA)," and insert -- (EWMA chart), --.

Column 19, Line 63, delete "Symbig™," and insert -- Symbiq™, --.

Column 20, Line 2-3, delete "27 4," and insert -- 274, --.